(12) United States Patent
Klin et al.

(10) Patent No.: US 12,156,696 B2
(45) Date of Patent: Dec. 3, 2024

(54) SYSTEMS AND METHODS FOR ASSESSING INFANT AND CHILD DEVELOPMENT VIA EYE TRACKING

(71) Applicant: Children's Healthcare of Atlanta, Inc., Atlanta, GA (US)

(72) Inventors: Ami Klin, Atlanta, GA (US); Warren Jones, Decatur, GA (US)

(73) Assignee: Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 18/545,362

(22) Filed: Dec. 19, 2023

(65) Prior Publication Data

US 2024/0115130 A1 Apr. 11, 2024

Related U.S. Application Data

(60) Continuation of application No. 17/943,719, filed on Sep. 13, 2022, now Pat. No. 11,864,832, which is a continuation of application No. 16/810,995, filed on Mar. 6, 2020, now Pat. No. 11,471,047, which is a division of application No. 15/029,808, filed as application No. PCT/US2014/055008 on Sep. 10, 2014, now Pat. No. 10,617,295.

(60) Provisional application No. 61/892,301, filed on Oct. 17, 2013, provisional application No. 61/892,300, filed on Oct. 17, 2013.

(51) Int. Cl.
*A61B 3/113* (2006.01)
*A61B 3/00* (2006.01)
*A61B 5/16* (2006.01)

(52) U.S. Cl.
CPC ............ *A61B 3/113* (2013.01); *A61B 3/0025* (2013.01); *A61B 5/163* (2017.08); *A61B 5/167* (2013.01); *A61B 5/168* (2013.01); *A61B 2503/04* (2013.01); *A61B 2503/06* (2013.01)

(58) Field of Classification Search
CPC ....... A61B 3/113; A61B 3/0025; A61B 5/163; A61B 5/167; A61B 5/168; A61B 2503/04; A61B 2503/06; G16H 15/00; G16H 40/40; G16H 40/63; G16H 50/30; G16H 50/70
USPC ....................................................... 600/558
See application file for complete search history.

(56) References Cited

U.S. PATENT DOCUMENTS

| | | | | |
|---|---|---|---|---|
| 11,666,259 B1 * | 6/2023 | Narayanan | ............. | G16H 15/00 |
| | | | | 600/558 |
| 2014/0253876 A1 * | 9/2014 | Klin | ...................... | G16H 20/70 |
| | | | | 351/210 |
| 2023/0148944 A1 * | 5/2023 | Lacy | ...................... | A61B 5/742 |
| | | | | 600/301 |

* cited by examiner

*Primary Examiner* — Mohammed A Hasan
(74) *Attorney, Agent, or Firm* — Morris, Manning & Martin, LLP; Daniel E. Sineway, Esq.

(57) ABSTRACT

Systems, devices, and methods are described for assessing the risk of developmental, cognitive, social, or mental abilities or disabilities in very young patients (e.g., in the first 2-6 months of life). Generally, the decline in visual fixation of a subject over time with respect to certain dynamic stimuli provides a marker of possible abilities or disabilities (such as ASD). The visual fixation of the subject is identified, monitored, and tracked over time through repeated eye tracking sessions, and data relating to the visual fixation is then analyzed to determine a possible increased risk certain conditions in the subject. A change in visual fixation as compared to similar visual fixation data of typically-developing subjects or to a subject's own, prior visual fixation data provides an indication of a developmental, cognitive, or mental ability or disability.

14 Claims, 65 Drawing Sheets

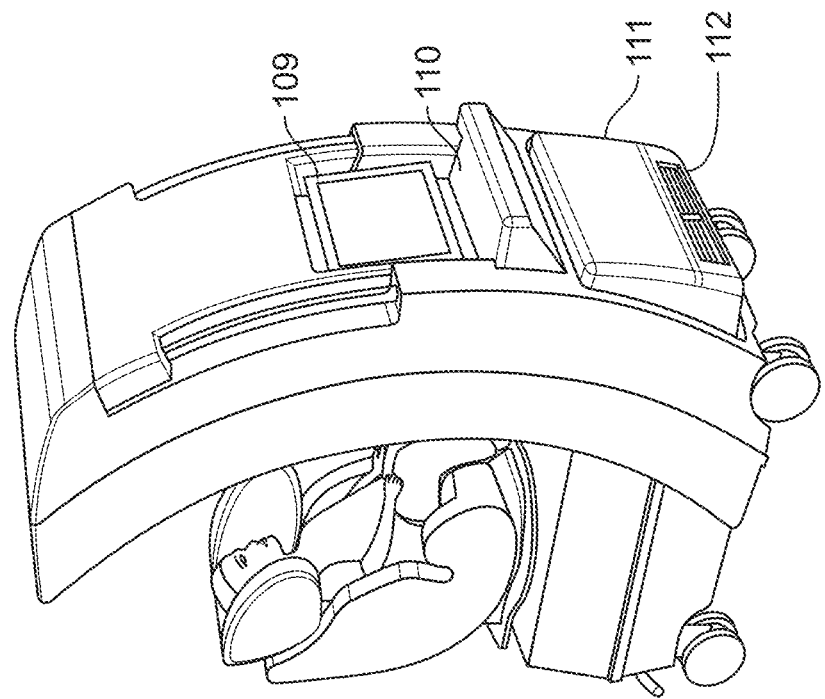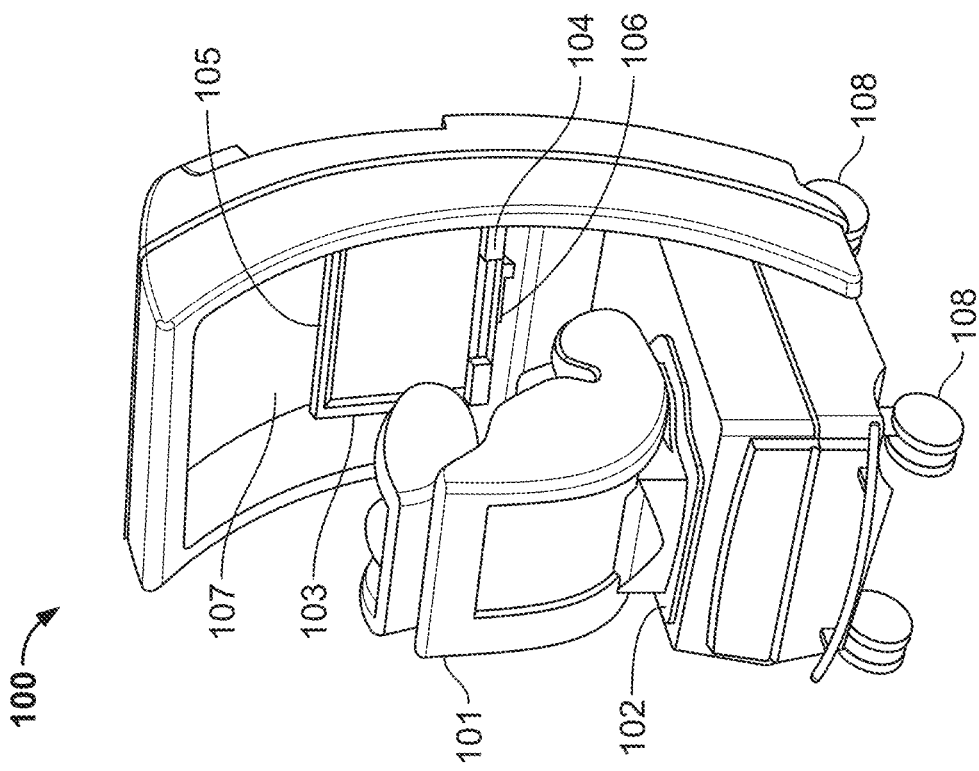
FIG. 2

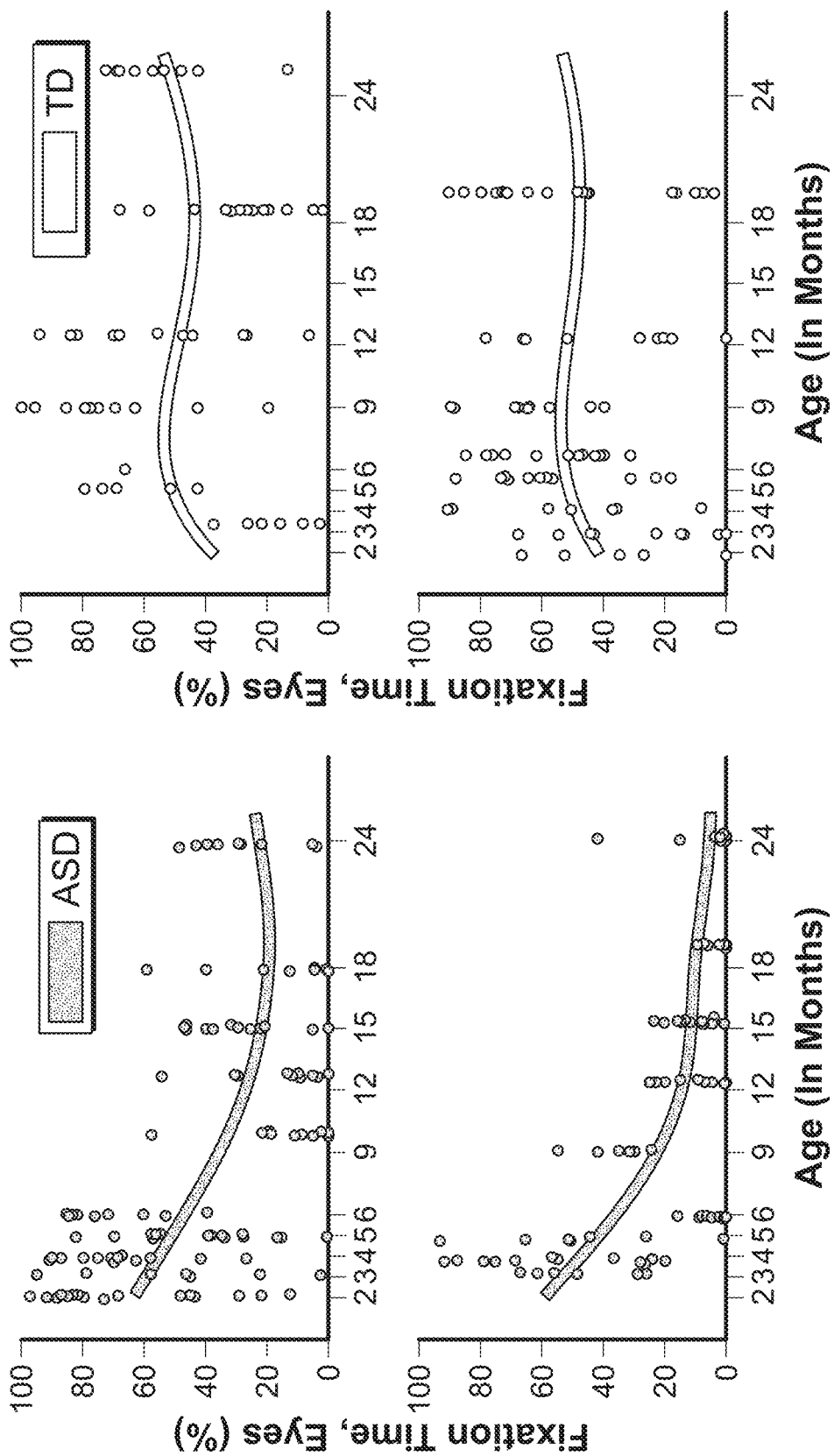

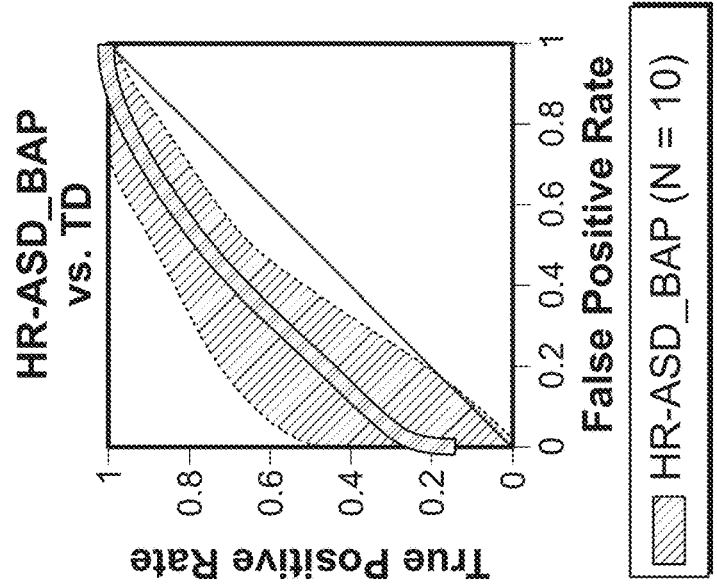
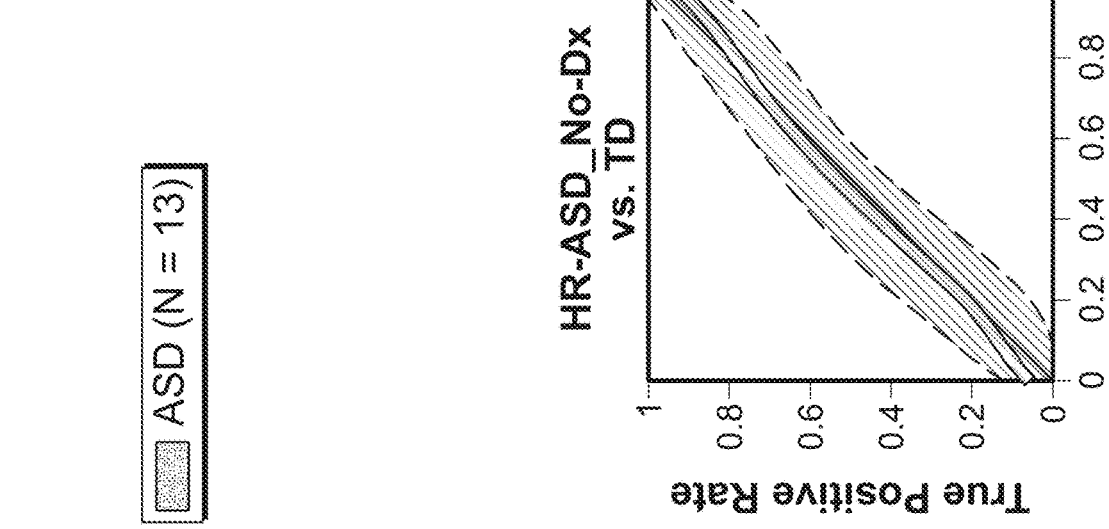
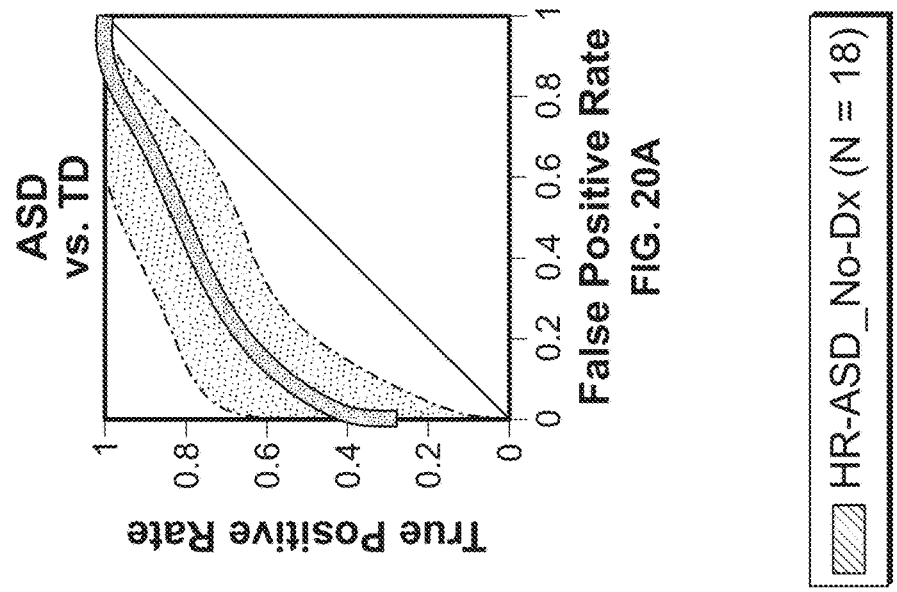
FIG. 20A
FIG. 20B
FIG. 20C

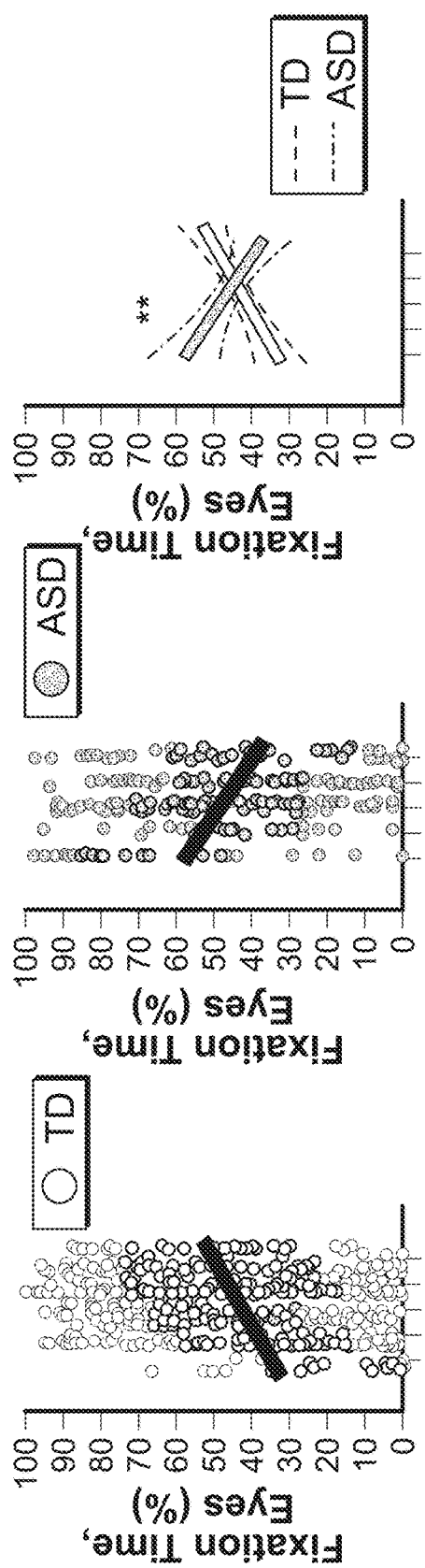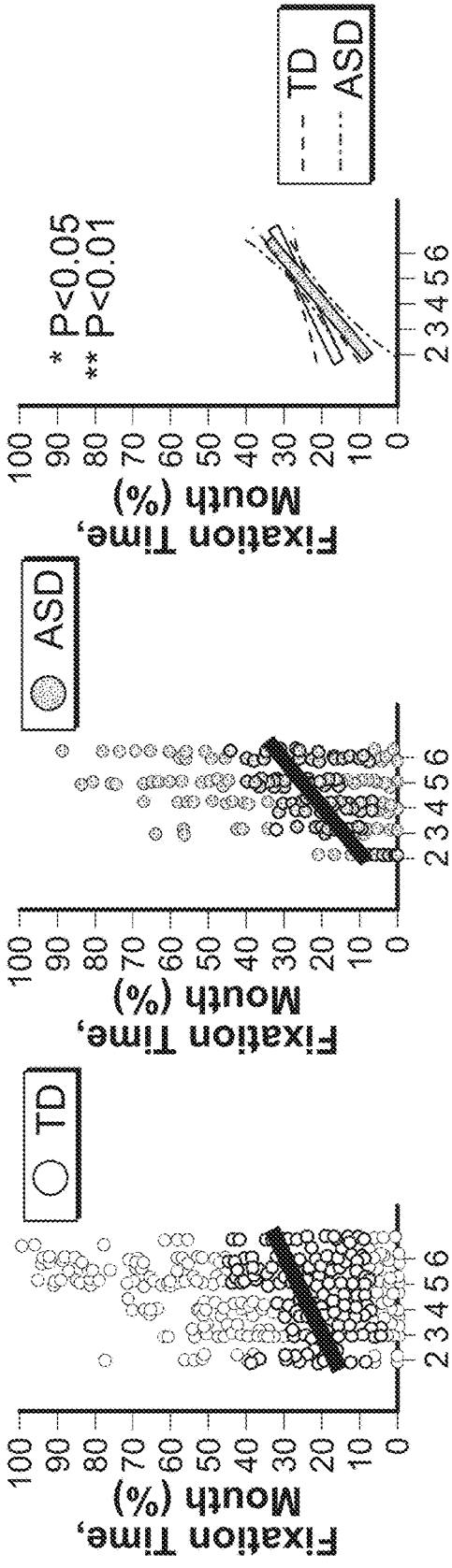

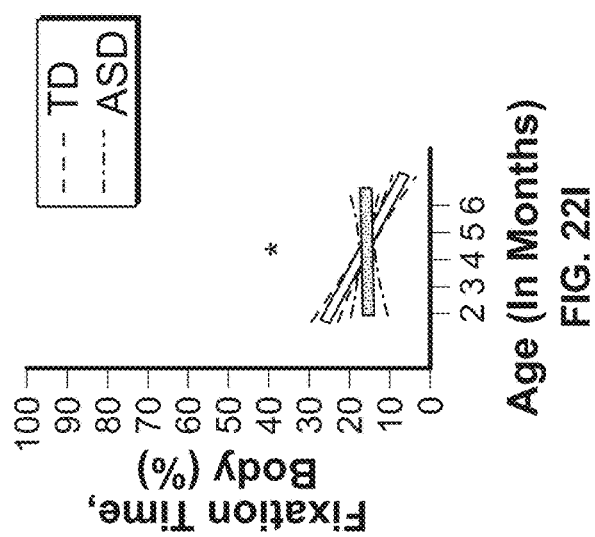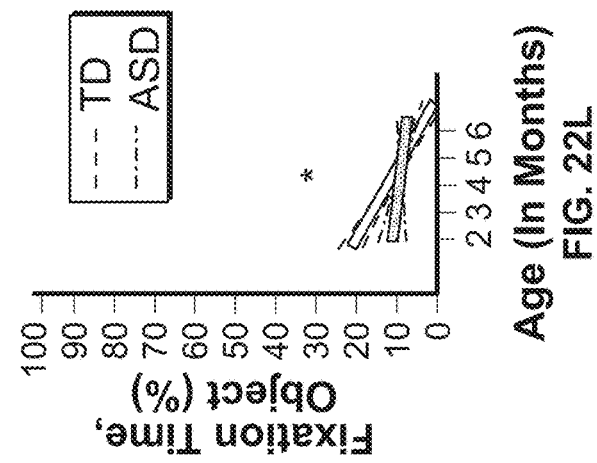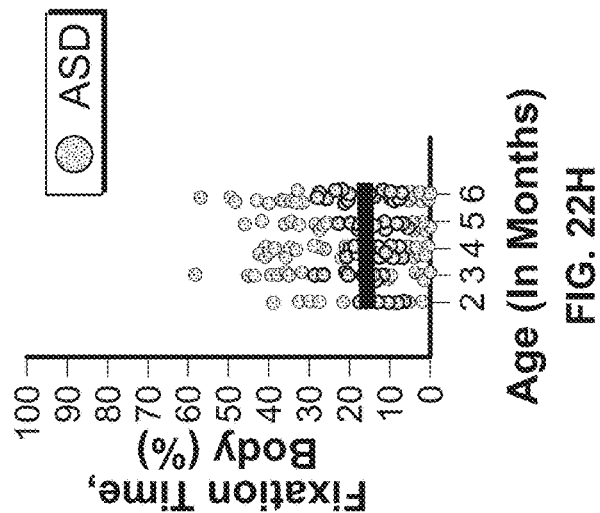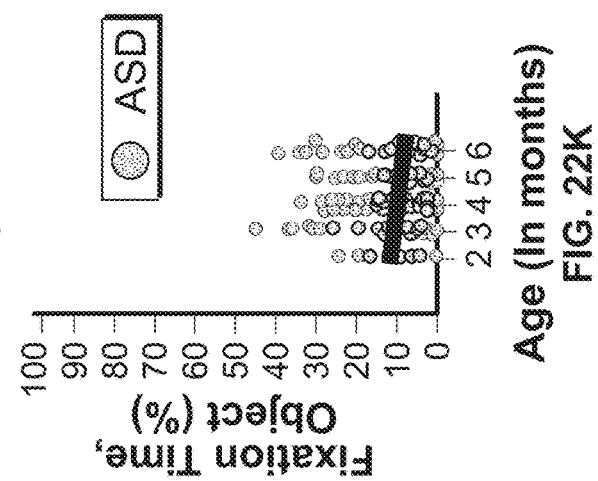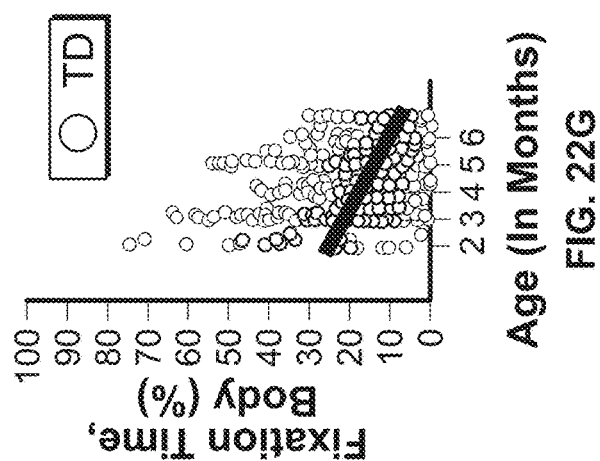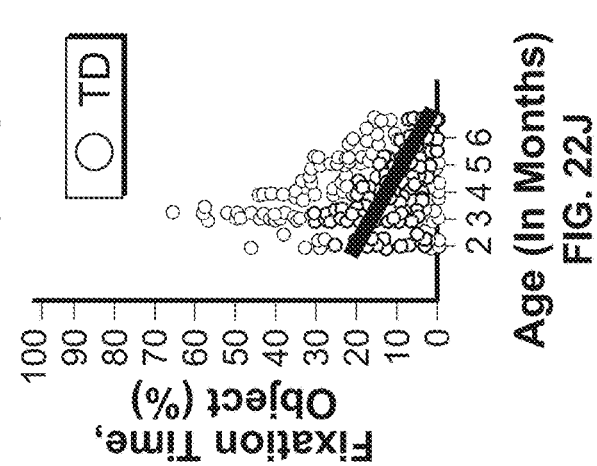

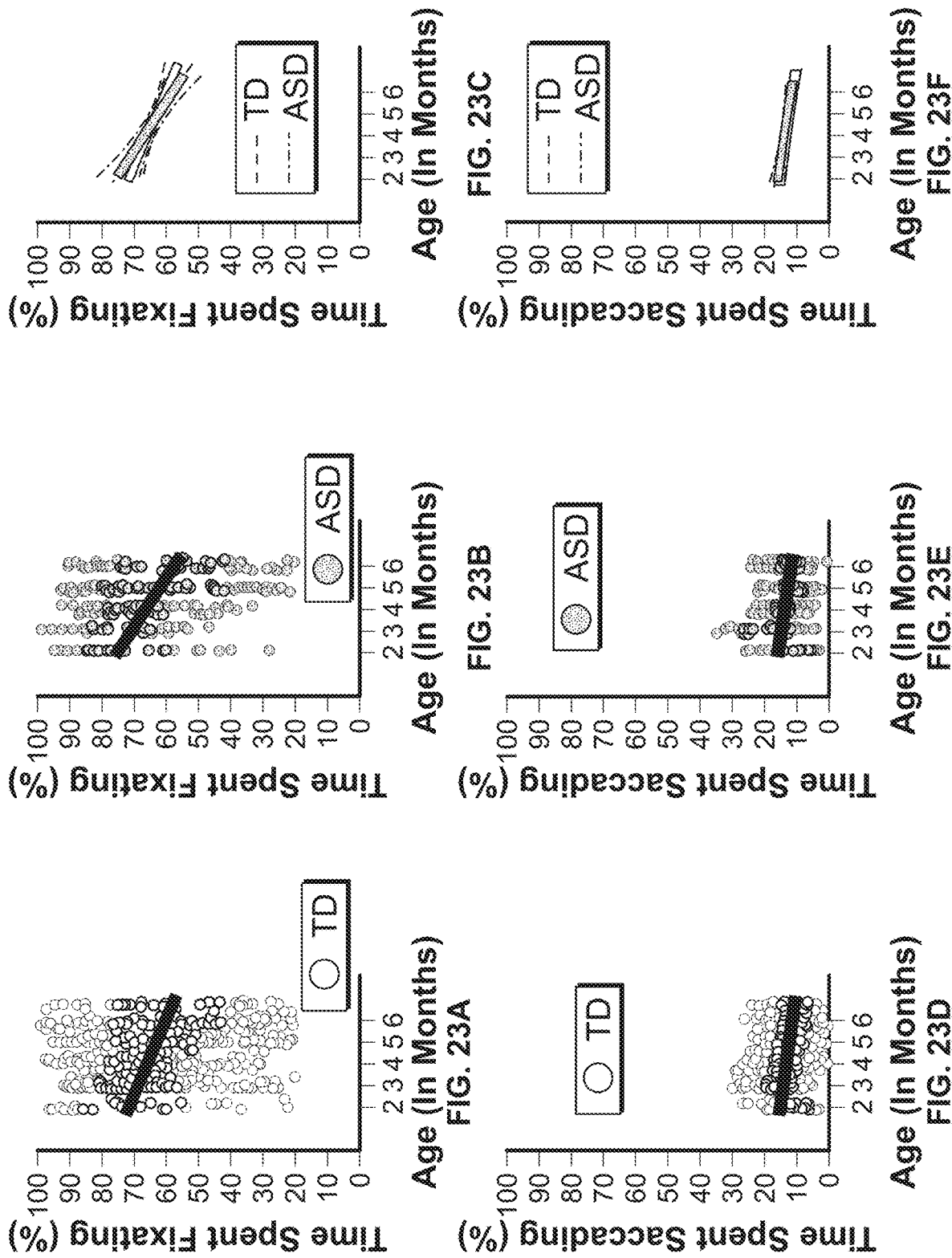

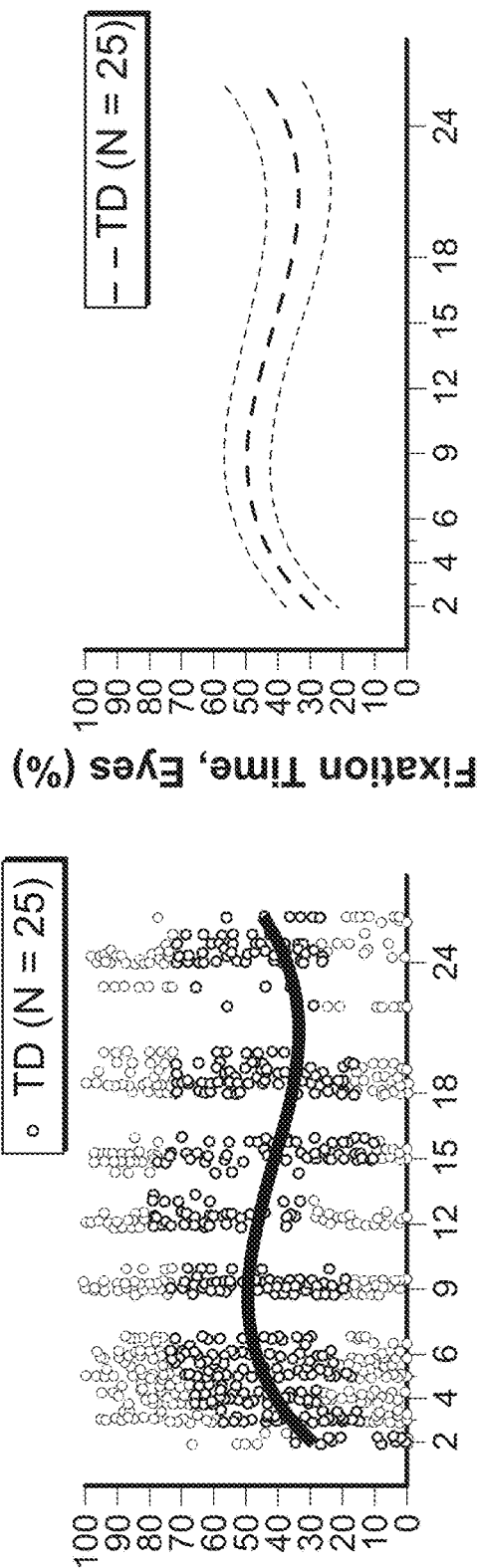
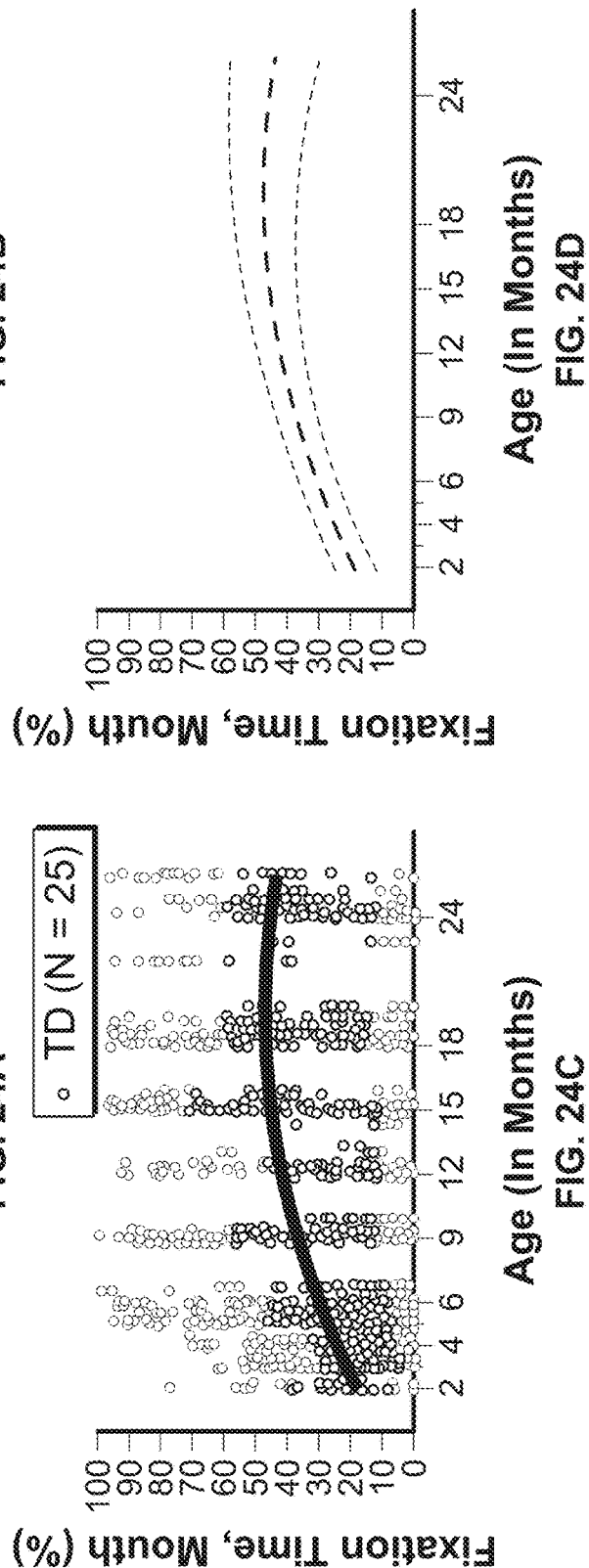
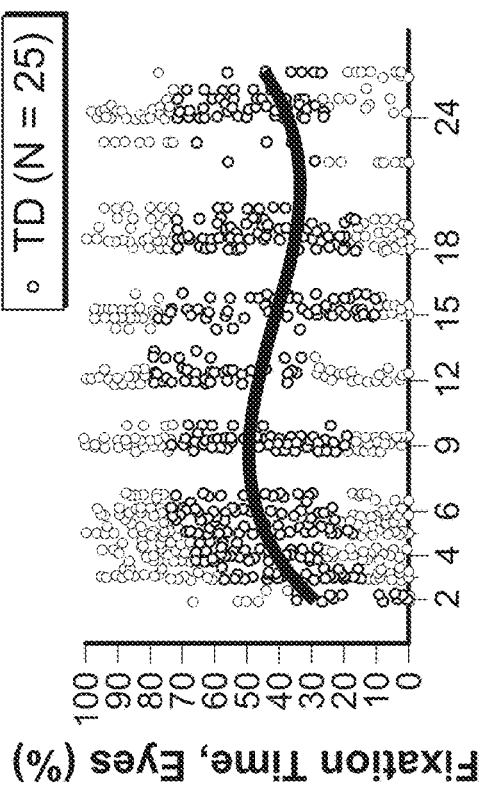
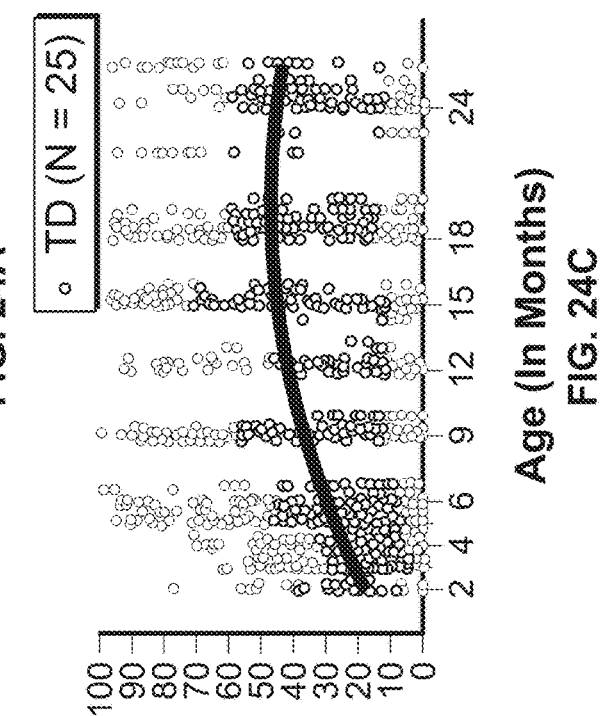
FIG. 24A
FIG. 24B
FIG. 24C
FIG. 24D

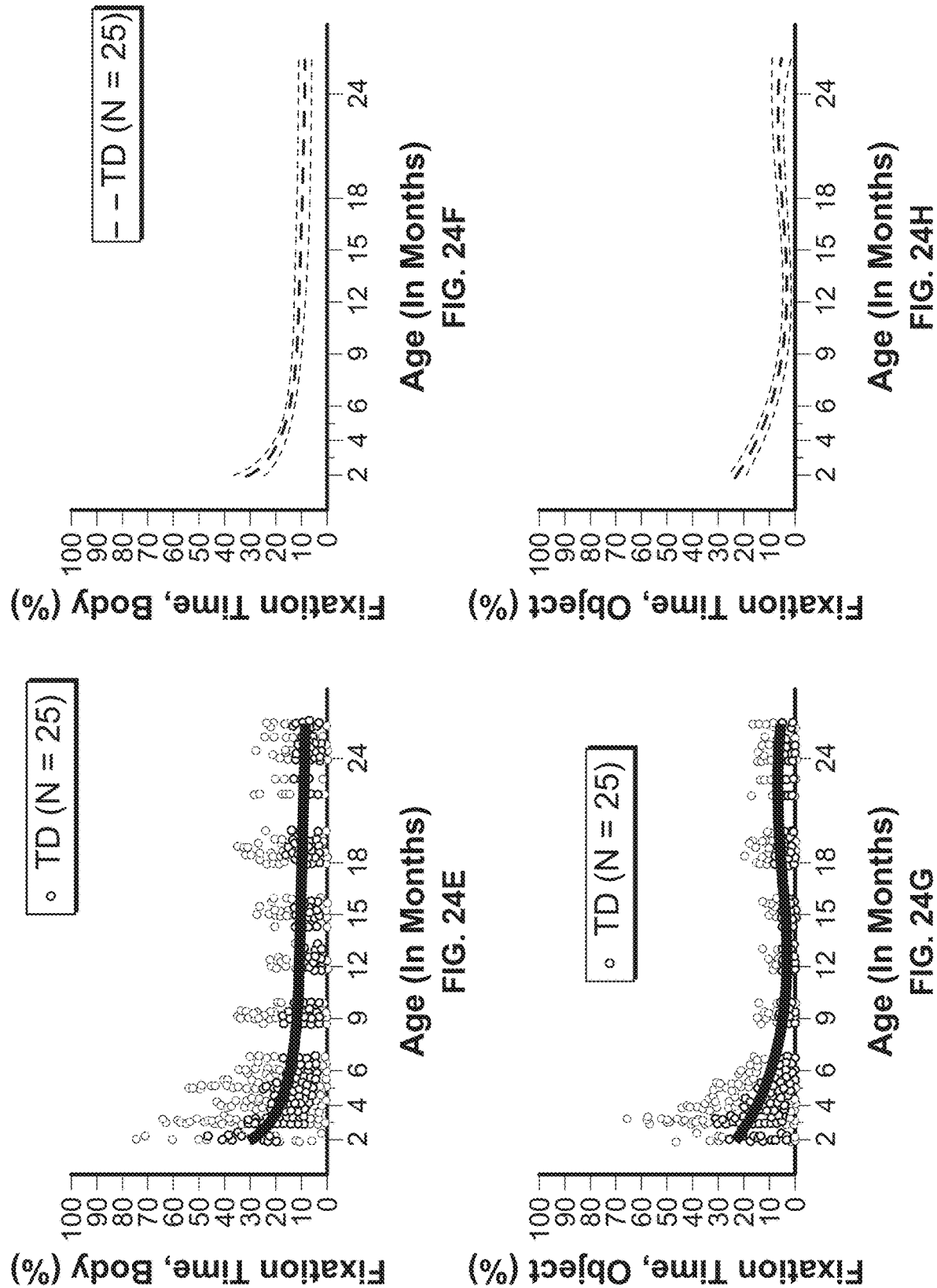

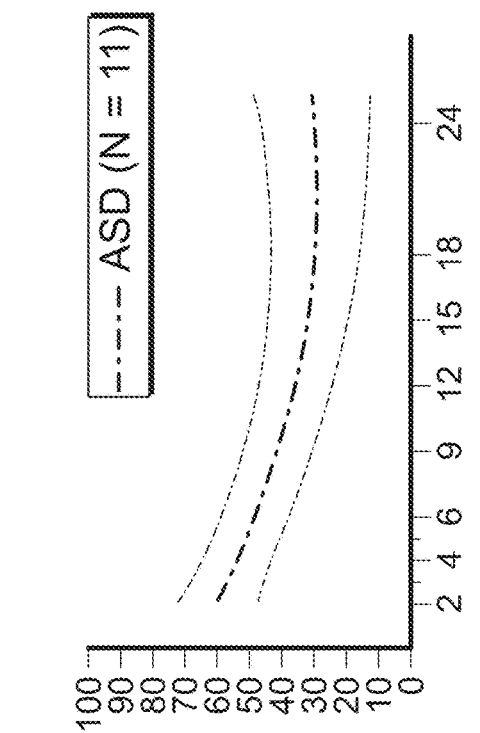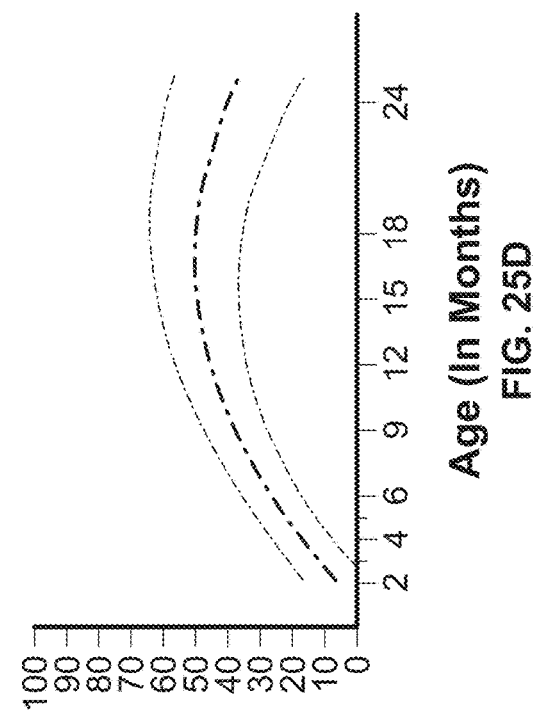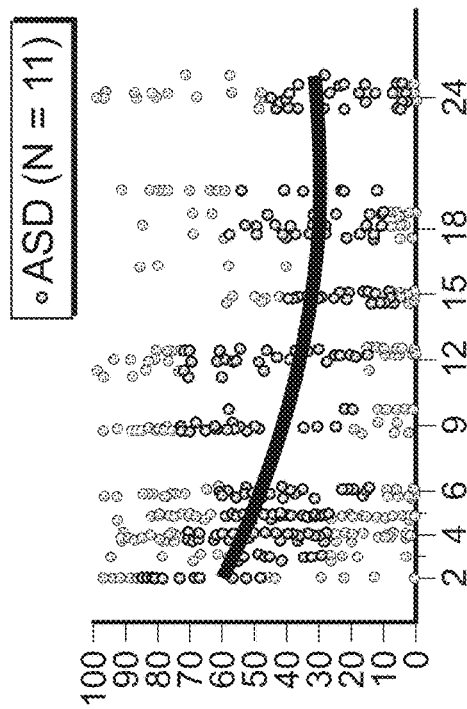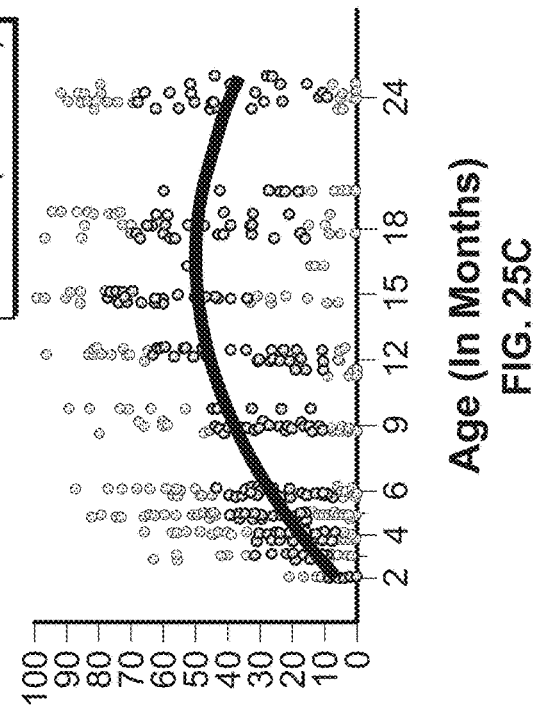

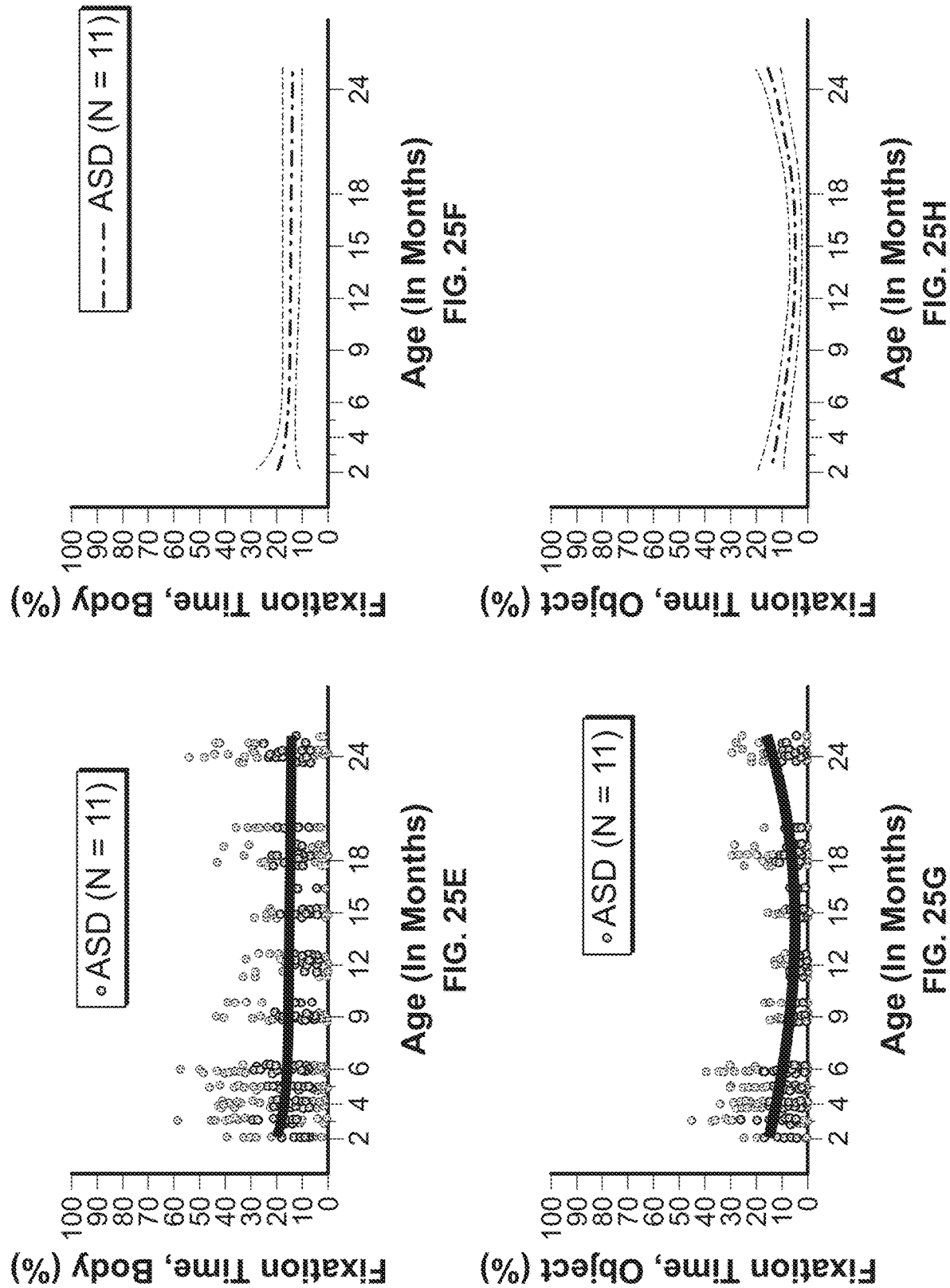

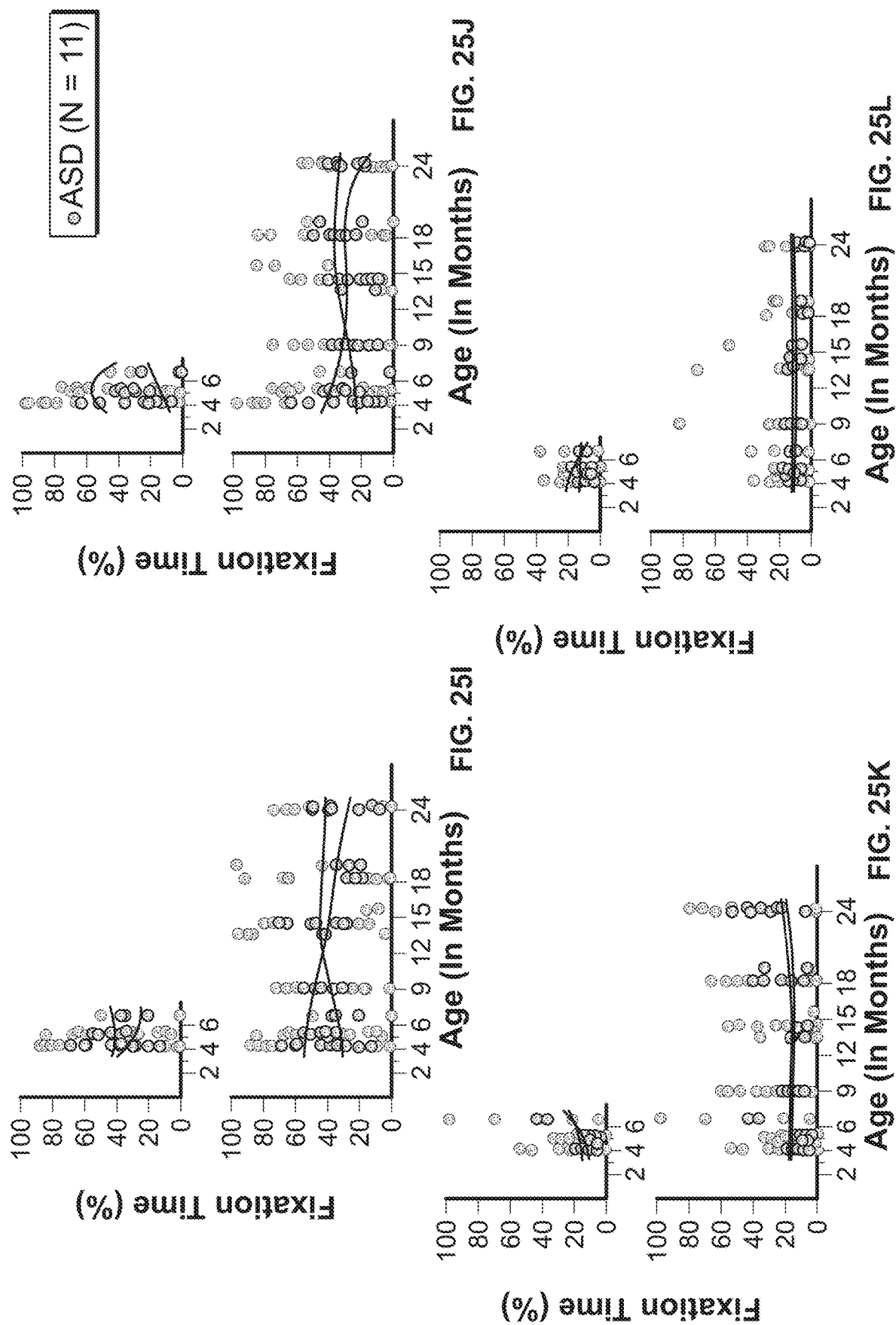

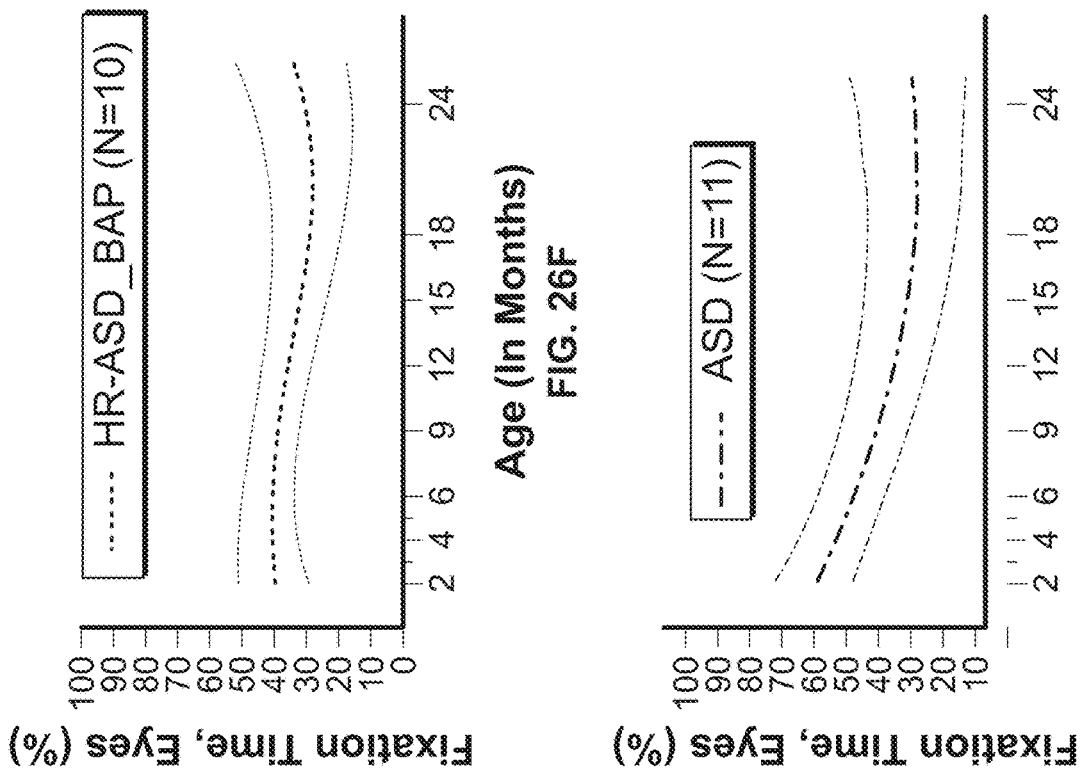
FIG. 26E
FIG. 26F
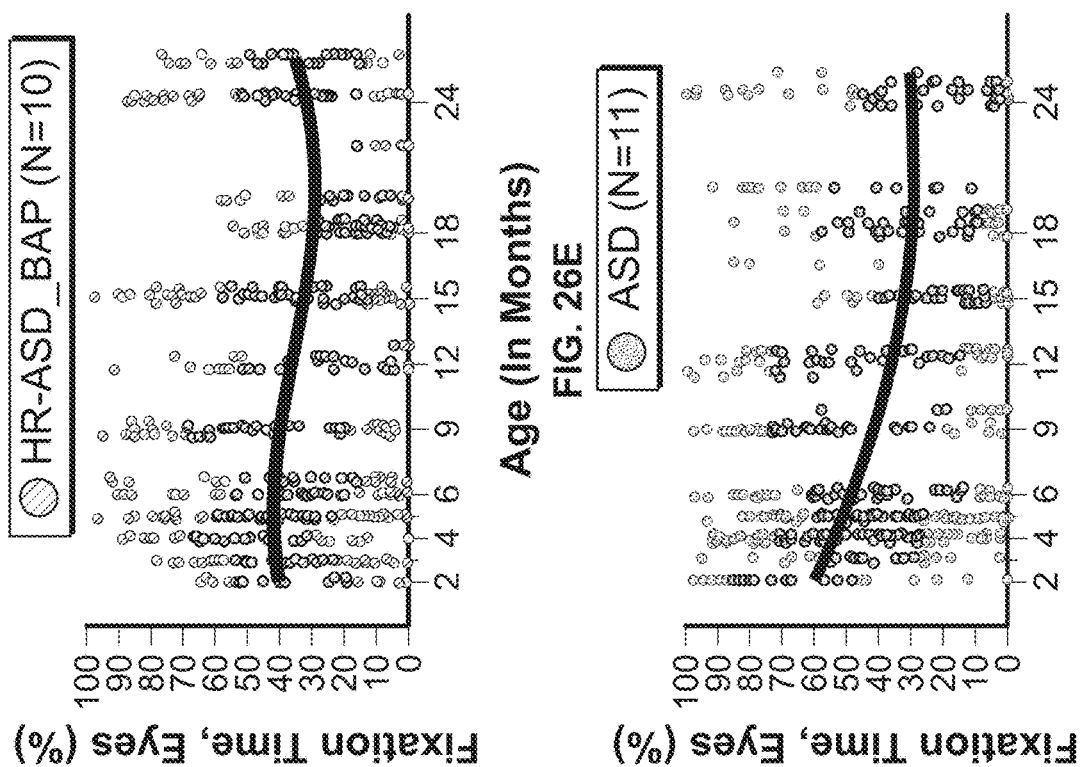
FIG. 26G
FIG. 26H

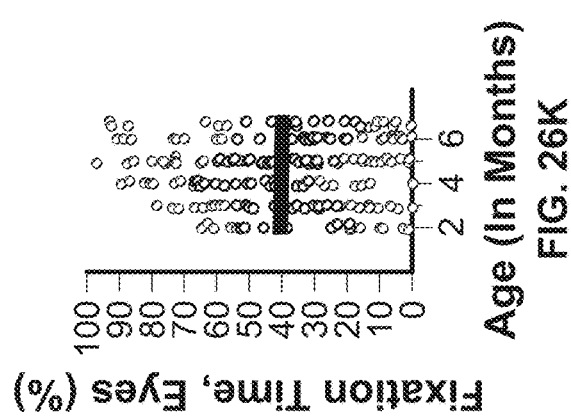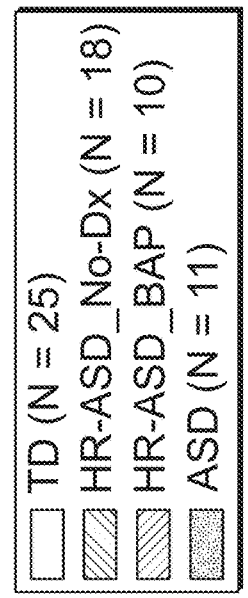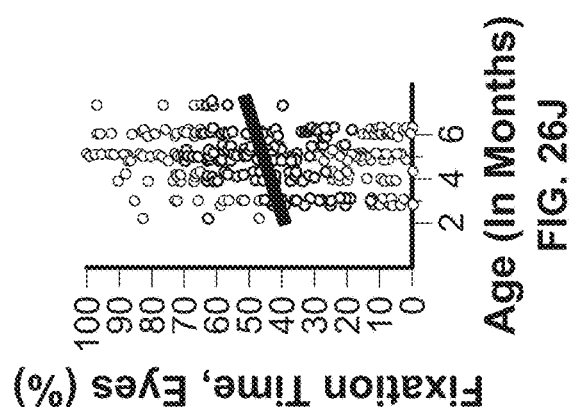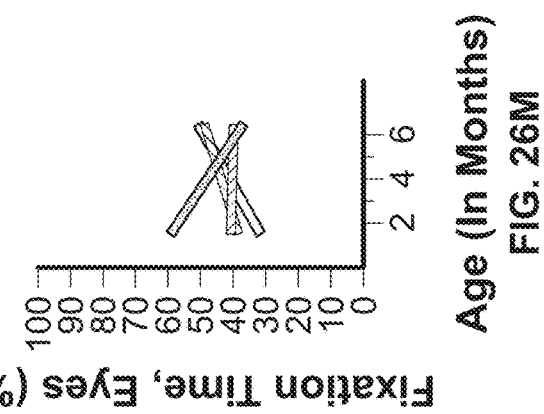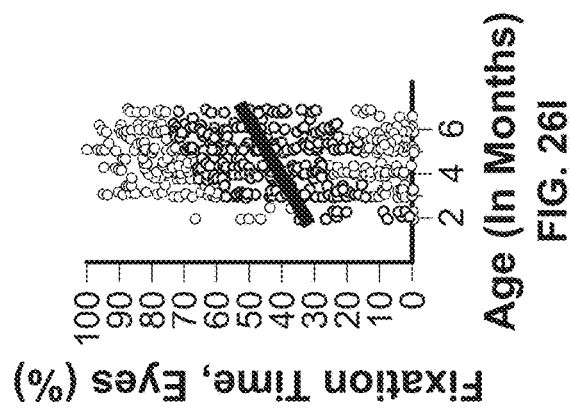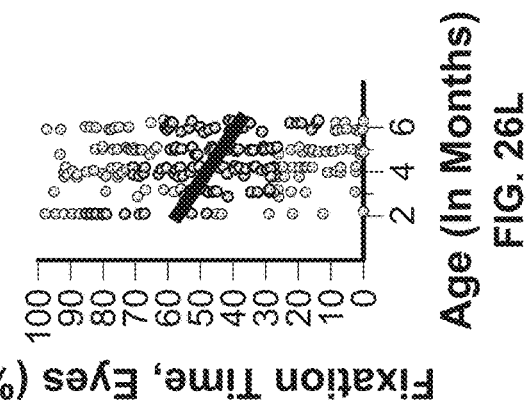

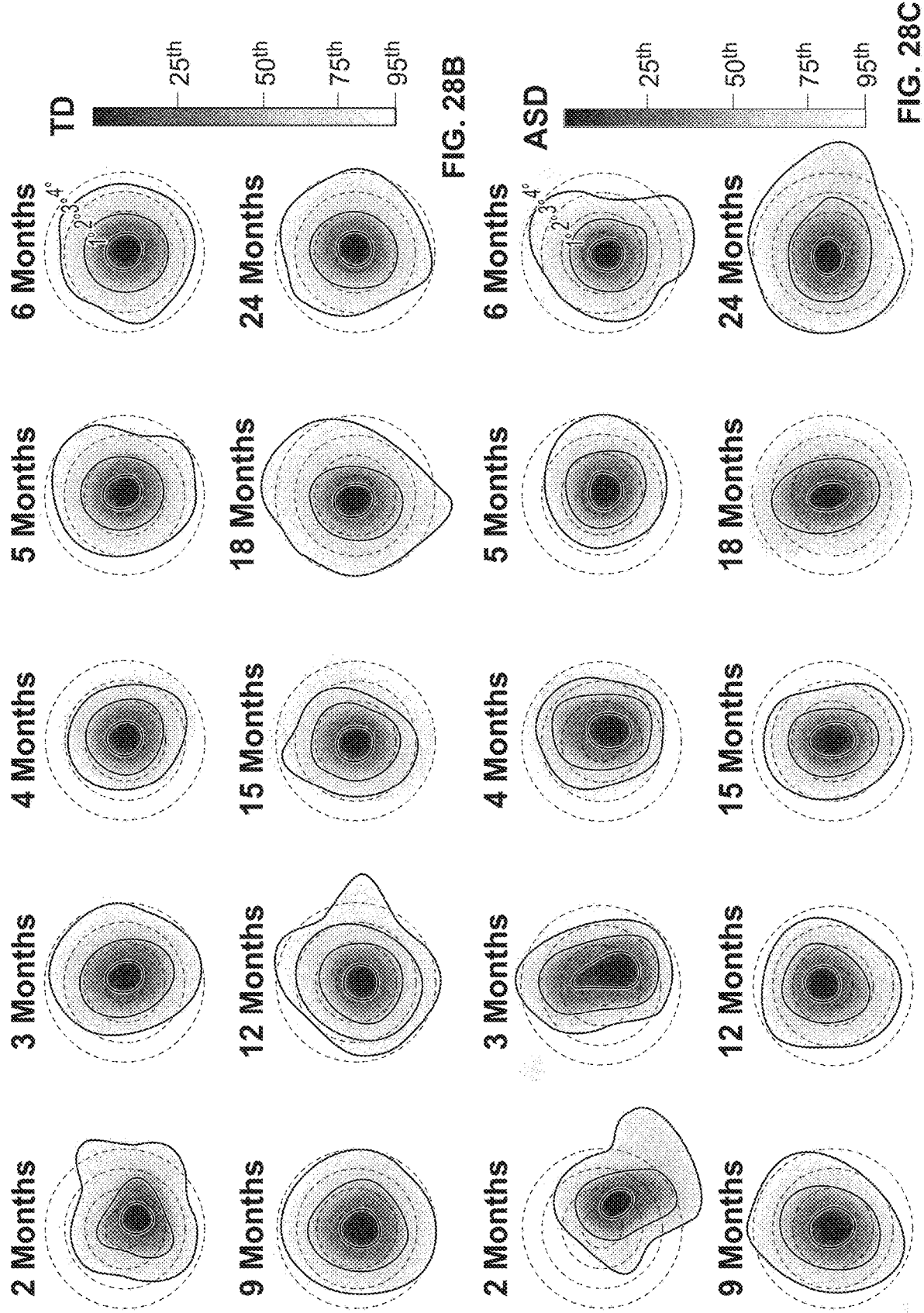

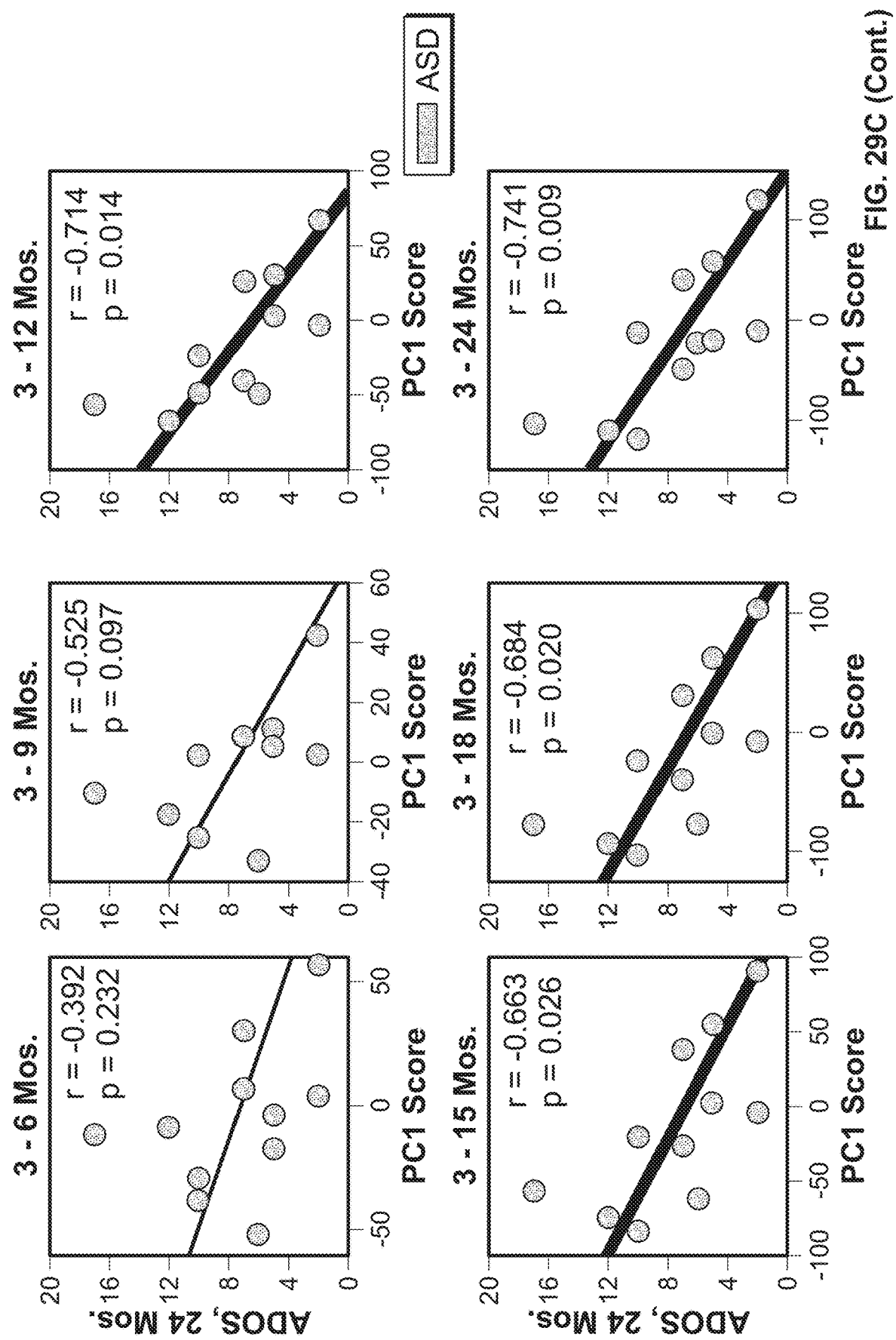

SYSTEMS AND METHODS FOR ASSESSING INFANT AND CHILD DEVELOPMENT VIA EYE TRACKING

CROSS-REFERENCE TO RELATED APPLICATIONS

This application is a continuation of, and claims benefit of and priority to, U.S. application Ser. No. 17/943,719, filed Sep. 13, 2022, entitled "Systems and Methods for Assessing Infant and Child Development via Eye Tracking," which is a continuation of, and claims benefit of and priority to, U.S. application Ser. No. 16/810,995, filed Mar. 6, 2020, entitled "Systems and Methods for Assessing Infant and Child Development via Eye Tracking," now U.S. Pat. No. 11,471,047, which is a divisional of, and claims benefit of and priority to, U.S. application Ser. No. 15/029,808, filed Apr. 15, 2016, entitled "Systems and Methods for Assessing Infant and Child Development via Eye Tracking," now U.S. Pat. No. 10,617,295, which is a national stage entry of, and claims benefit of and priority under 35 U.S.C. § 371 to, International Application No. PCT/US2014/055008, filed Sep. 10, 2014, entitled "Methods for Assessing Infant and Child Development via Eye Tracking", which claims the benefit under 35 U.S.C. § 119(e) to U.S. Provisional Application No. 61/892,301, filed Oct. 17, 2013, entitled "Systems and Methods for Assessing Infant and Child Development via Eye Tracking," and U.S. Provisional Application No. 61/892,300, filed Oct. 17, 2013, entitled "Systems and Methods for Assessing Infant and Child Development via Eye Tracking," all of which are hereby incorporated by reference herein in their entireties.

STATEMENT REGARDING FEDERALLY-SPONSORED RESEARCH

This invention was made with government support under grant number RO1 MH083727 awarded by the National Institute of Mental Health and the Simons Foundation. The government has certain rights in the invention.

BACKGROUND

Developmental disorders such as autism spectrum disorders (ASD) affect nearly 14% of children in the United States. Diagnostic methods for conditions such as ASD vary considerably, and even the use of "best practice" tools provides rather poor sensitivity and specificity to the conditions. Late diagnosis of developmental disabilities reduces effectiveness of treatments and often results in poor outcomes. Furthermore, treatment providers (e.g., pediatricians or other medical professionals) lack adequate tools for measuring progress in these conditions, especially very early in a patient's life.

BRIEF SUMMARY

The present systems, devices, and methods relate generally to the detection of developmental, cognitive, social, or mental abilities or disabilities, including ASD, in subjects using analysis of eye tracking data generated in response to display of specific predetermined visual stimuli (e.g., one or more videos) to the subject. Specifically, the detection of developmental, cognitive, social, or mental disabilities is applicable to the detection of such conditions as, but not limited to, expressive and receptive language developmental delays, non-verbal developmental delays, intellectual disabilities, intellectual disabilities of known or unknown genetic origin, traumatic brain injuries, disorders of infancy not otherwise specified (DOI-NOS), social communication disorder, and autism spectrum disorders (ASD), as well as such conditions as attention deficit hyperactivity disorder (ADHD), attention deficit disorder (ADD), post-traumatic stress disorder (PTSD), concussion, sports injuries, and dementia. The present systems, devices, and methods are also applicable to the measurement of developmental, cognitive, social, or mental abilities such as, but not limited to, expressive and receptive language levels in the normative to exceptional range, non-verbal cognitive function in the normative to exceptional range, and social developmental levels in the normative to exceptional range. Furthermore, such systems, devices, and methods can be applied to quantitatively measure and monitor symptomatology of the respective ability or disability and, in certain cases, provide more accurate and relevant prescriptive information to patients, families, and service providers. According to additional aspects, the disclosed systems, device, and methods can be used to predict outcome in subjects with autism (thus providing prescriptive power) while also providing similar diagnostic and prescriptive measures for global developmental, cognitive, social, or mental ability or disabilities.

According to some embodiments, the present systems, devices, and methods relate to assessing the risk of developmental, cognitive, social, or mental abilities or disabilities in very young patients (e.g., in the first 2-6 months of life). According to certain aspects, the decline in visual fixation of a subject over time with respect to certain dynamic stimuli provides a marker of a possible developmental, cognitive, social, or mental abilities or disabilities (such as ASD) of the subject. The visual fixation of the subject is identified, monitored, and tracked over time (e.g., in the first 6 months of life) through repeated eye tracking sessions, and data relating to the visual fixation is then compared to relative norms to determine a possible increased risk of such a condition in the subject. A change in visual fixation (in particular, a decline in visual fixation by a subject with the image of eyes, body, or other region-of-interest of a person or object displayed on a visual stimulus) as compared to similar visual fixation data of typically-developing subjects or to a subject's own, prior visual fixation data provides an indication of a developmental, cognitive, or mental disorder.

According to some embodiments, the present disclosure relates to systems, methods, and devices for evaluating, monitoring or diagnosing a developmental, cognitive, social, or mental disability or ability based on identifying a change in visual fixation of an individual over time during at least two sessions. Generally, these methods comprise at least the following steps: positioning an individual in a data collection apparatus during a first session, the apparatus having a display device for displaying a stimulus to the individual and a sensor for detecting visual fixation of the individual in response to the stimulus displayed by the display device, wherein the individual is positioned in an orientation in the data collection apparatus with respect to the display device and the sensor that allows for collection of eye movement data; during the first session, causing display on the display device of a first visual stimulus to the individual; receiving first eye movement data from the sensor that indicates visual fixation of the individual with respect to the displayed first visual stimulus; positioning the individual in the data collection apparatus during a second session; during the second session, causing display on the display device of a second visual stimulus to the individual; receiving second eye movement data from the sensor that indicates visual fixation of the individual with respect to the displayed second visual stimulus; and comparing, via software executing on a processor, the first eye movement data to the second eye movement data to identify a change in visual fixation for the individual with respect to the displayed first visual stimulus and the displayed second visual stimulus, wherein the change in visual fixation over time for the individual is a marker of a developmental, cognitive, social, or mental disability or ability.

According to further embodiments, the present disclosure relates to systems, methods, and devices for identifying a change in visual fixation of an individual over time. Generally, these methods comprise at least the following steps: receiving a first data set collected from an eye tracking device indicative of an individual's visual fixation with respect to a first visual stimulus, wherein the individual's visual fixation corresponds to at least one spatial region-of-interest in the first visual stimulus; receiving a second data set collected from the eye tracking device indicative of the individual's visual fixation with respect to a second visual stimulus, wherein the individual's visual fixation corresponds to at least one spatial region-of-interest in the second visual stimulus, and wherein the second data set was collected during a second session performed after a first session in which the first data set was collected; generating, via software executing on a processor, a representation of the first data set and the second data set, wherein the representation demonstrates visual fixation with respect to the at least one spatial region-of-interest; and calculating, via software executing on a processor, a change or rate-of-change in visual fixation for the individual from the first session to the second session based on the representation of the first data set and the second data set, wherein the change or rate-of-change in visual fixation from the first session to the second session for the individual is a marker of a developmental, cognitive, social, or mental disability or ability.

According to additional embodiments, the present disclosure relates to systems, methods, and devices for evaluating, monitoring or diagnosing a developmental, cognitive, social, or mental disability or ability based on change or rate-of-change of visual fixation of an individual over time during at least two sessions. Generally, these methods comprise at least the following steps: positioning an individual in a data collection apparatus during a first session, the apparatus having a display device for displaying a stimulus to the individual and a sensor for detecting visual fixation of the individual in response to the stimulus displayed by the display device, wherein the individual is positioned in an orientation in the data collection apparatus with respect to the display device and the sensor that allows for collection of eye movement data; during the first session, causing display on the display device of a first visual stimulus to the individual; receiving first eye movement data from the sensor that indicates visual fixation of the individual with respect to the displayed first visual stimulus; positioning the individual in the data collection apparatus during a second session; during the second session, causing display on the display device of a second visual stimulus to the individual; receiving second eye movement data from the sensor that indicates visual fixation of the individual with respect to the displayed second visual stimulus; generating, via software executing on a processor, a representation of the first eye movement data and the second eye movement data, wherein the representation demonstrates a change or rate-of-change in visual fixation for the individual from the first session to the second session; retrieving, via software executing on the processor, a comparison representation of change or rate-of-change in visual fixation for a comparison group with respect to the displayed first visual stimulus and the displayed second visual stimulus; and comparing, via software executing on the processor, the change or rate-of-change in visual fixation for the individual to the change or rate-of-change in visual fixation for the comparison group to determine whether the change or rate-of-change in visual fixation for the individual falls outside a predetermined range of the change or rate-of-change in visual fixation for the comparison group and thereby indicates a likelihood that the individual has a developmental, cognitive, or mental disability or ability.

According to certain embodiments, the present disclosure relates to systems, methods, and devices for evaluating, monitoring or diagnosing a developmental, cognitive, social, or mental disorder based on change or rate-of-change of visual fixation of an individual over time during a plurality of sessions. Generally, these methods comprise at least the following steps: (a) positioning an individual in a data collection apparatus during a session, the apparatus having a display device for displaying a stimulus to the individual and an eye tracking device for detecting visual fixation of the individual in response to the stimulus displayed by the display device, wherein the individual is positioned in an orientation in the data collection apparatus with respect to the display device and the eye tracking device that allows for collection of eye movement data; (b) during the session, causing display on the display device of a calibration image to the individual, wherein the calibration image is used to draw the attention of the individual to a spatial region-of-interest associated with the calibration image on the display device for purposes of calibrating visual fixation of the individual; (c) during the session and after causing display on the display device of the calibration image to the individual, causing display on the display device of an audiovisual stimulus to the individual, wherein the audiovisual stimulus comprises at least one scene of an actor portraying a caregiver; (d) in response to causing display of the audiovisual stimulus to the individual, receiving eye movement data from the eye tracking device that indicates visual fixation of the individual with respect to a particular spatial region-of-interest associated with the eyes of the actor portraying the caregiver in the displayed visual stimulus; (e) repeating steps a-d for a plurality of sessions within the first 24 months of life of the individual, wherein each session is separated by at least about one month; (f) upon completion of steps a-e, generating, via software executing on a processor, a representation of the received eye movement data over the plurality of sessions, wherein the representation demonstrates a change or rate-of-change in visual fixation for the individual over the plurality of sessions; (g) retrieving, via software executing on the processor, a comparison representation of change or rate-of-change in visual fixation for a comparison group with respect to a comparable plurality of sessions; and (h) comparing, via software executing on the processor, the change or rate-of-change in visual fixation for the individual to the change or rate-of-change in visual fixation for the comparison group to determine whether the change or rate-of-change in visual fixation for the individual falls outside a predetermined range of the change or rate-of-change in visual fixation for the comparison group and thereby indicates a likelihood that the individual has a developmental, cognitive, social, or mental disorder.

According to some aspects, the change in visual fixation of an individual comprises a decline in visual fixation of the individual with respect to the displayed first visual stimulus as compared to the displayed second visual stimulus. According to further aspects the change in visual fixation of the individual with respect to the displayed first visual stimulus as compared to the displayed second visual stimulus comprises a change in visual fixation that is statistically different from a change in visual fixation measured in a comparison group of individuals. According to certain embodiments, the change in visual fixation comprises a deviation in visual fixation equal to or greater than 1.96 times the standard error of the mean change in visual fixation of a comparison group.

According to certain aspects, the first eye movement data and the second eye movement data include visual fixation data indicative of the individual's visual fixation with respect to one or more regions-of-interest in the displayed first visual stimulus and the displayed second visual stimulus. In one aspect, the one or more regions-of-interest are spatially predefined. In further aspects, the one or more regions-of-interest comprise one or more discrete regions of visual space. In still further aspects, the one or more discrete regions of visual space are measured in degrees of visual angle equal to at least twice the minimum resolvable accuracy of the first eye movement data or the second eye movement data with 95% statistical confidence.

According to some aspects, the step of comparing the first eye movement data to the second eye movement data further comprises generating, via software executing on the processor, a graphical representation of the individual's visual fixation with respect to the one or more regions-of-interest in the displayed first visual stimulus and the displayed second visual stimulus. In some aspects, the graphical representation of the individual's visual fixation comprises one or more graduated lines marking measures of variance with respect to a comparison group. In certain aspects, the graduated lines marking measures of variance may comprise percentiles, standard deviations, or some other measure. In further aspects, the change in visual fixation comprises a decline in spatial visual fixation of the individual with respect to the one or more regions-of-interest.

According to some aspects, the visual stimulus (e.g., first visual stimulus and/or the second visual stimulus) comprise one or more of a static visual stimulus, a dynamic visual stimulus, a pre-recorded visual stimulus, a pre-recorded audiovisual stimulus, a live visual stimulus, a live audiovisual stimulus, a two-dimensional stimulus, or a three-dimensional stimulus. In certain aspects, the visual stimuli are normed for eliciting specific eye movement responses with greater than 95% statistical confidence. In further aspects, the visual stimuli elicit eye movement responses to discrete spatial-temporal locations with greater than 95% statistical confidence. In yet further aspects, the visual stimuli have measurable presentation durations equal to at least half the minimum eye movement fixation duration for the individual. In certain aspects, the minimum eye movement fixation may be measured, for example, in milliseconds or some other relevant time measure. In some aspects, the first visual stimulus is the same as the second visual stimulus, whereas in other aspects, the first visual stimulus is different from the second visual stimulus.

In some aspects, the data collection apparatus is specifically adapted for individuals less than 24 months old. In certain aspects, the data collection apparatus is specifically adapted for individuals less than 6 months old. In some aspects, the data collection apparatus includes a support device for seating and confining the individual in the orientation with respect to the display device and the sensor. In further aspects, the data collection apparatus includes a support device for linearly positioning the individual with respect to the display device such that a linear distance from the display device to the individual's eyes is minimized, while the available dynamic focal range of the eye movement sensor is maximized. In yet further aspects, the linear distance is in a range of about 40-80 cm and wherein the available dynamic focal range is about 50-70 cm.

According to some aspects, the data collection apparatus includes a support device for rotationally positioning the individual's head and eyes in a rotational position with respect to the display device such that eyelid separation, when not blinking, is maximized at the widest physical distance, while occlusion of the cornea by the eyelid is minimized or eliminated. In certain aspects, the rotational position of the head of the individual with respect to the display device is tilted forwards and downwards in a range of about 0-24 degrees. In some aspects of the data collection apparatus, the sensor comprises an eye tracking device. In additional aspects, the steps of positioning the individual in the data collection apparatus further comprise positioning the individual's eyes are about 60 cm from the display device and the sensor, positioning the head of the individual at an angle tilted forwards and downwards at about 12 degrees, and stabilizing head and neck supports of the data collection apparatus to maintain the position.

In some aspects, when at least two sessions are conducted, the first session and the second session occur at two of the following ages of an individual: 2 months old, 3 months old, 4 months old, 5 months old, 6 months old, 9 months old, 12 months old, 15 months old, 18 months old, and 24 months old. In certain aspects, the first session and second session are separated by a predetermined time period, which may be at least one calendar month.

According to some aspects, the step of scrubbing the eye movement data to remove poor quality data points based on insufficient data collection and/or poor quality data. According to certain aspects, an interpretation of insufficient data collection may be comprised of one or more of the following: a static threshold for setting the minimum percentage of visual fixation directed towards the stimulus, a fuzzy logic or adaptive threshold for setting the minimum percentage of visual fixation directed towards the stimulus, a static threshold for setting the minimum percentage of visual fixation directed away from the stimulus, a fuzzy logic or adaptive threshold for setting the minimum percentage of visual fixation directed away from the stimulus. According to further aspects, an interpretation of poor quality data may be comprised of one or more of the following: a static threshold for poor quality calibration accuracy, a fuzzy logic or adaptive threshold for poor quality calibration accuracy, a static threshold for low signal-to-noise ratio during fixation eye movements, a fuzzy logic or adaptive threshold for low signal-to-noise ratio during fixation eye movements, a static threshold for ratio of head movement artifact to eye movement signal, a fuzzy logic or adaptive threshold for ratio of head movement artifact to eye movement signal. In yet further aspects, one interpretation of signal-to-noise ratio during fixation eye movements may be quantified as the measurement variance in fixation location relative to the measurement mean fixation location, in one or more eye movement fixations.

Variations and modifications of these embodiments and aspects will occur to those of skill in the art after reviewing this disclosure. The foregoing features and aspects may be implemented, in any combination and subcombination (including multiple dependent combinations and subcombinations), with one or more other features described herein. The various features described or illustrated herein, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 2 shows front and rear perspective views, respectively, of an illustrative device for the assessment, screening, monitoring, or diagnosis of developmental or cognitive conditions in a subject, according to certain embodiments of the present disclosure;

FIGS. 17D and 17E show, respectively, graphical representations of experimental data with FDA curve fits plotting percentage of total fixation time for the test subjects on the "eye" regions-of-interest in the corresponding stimuli, from 2 until 24 months of age, for two representative children with ASD, and two representative typically-developing children, according to one embodiment of the present disclosure.

FIGS. 20A-20C show graphs illustrating visual fixation between individuals of 2-6 months relative to outcome levels of affectedness for one experimental test group, according to one embodiment of the present disclosure.

FIGS. 22A-22C show graphs illustrating raw eye fixation data collected in the first 6 months, for one experimental test group, according to one embodiment of the present disclosure.

FIGS. 22D-22F show graphs illustrating raw mouth fixation data collected in the first 6 months, for one experimental test group, according to one embodiment of the present disclosure.

FIGS. 22G-22I show graphs illustrating raw body fixation data collected in the first 6 months, for one experimental test group, according to one embodiment of the present disclosure.

FIGS. 22J-22L show graphs illustrating raw object fixation data collected in the first 6 months, for one experimental test group, according to one embodiment of the present disclosure.

FIGS. 23A-23C show graphs illustrating data plots of percentage of total time spent fixating for individuals between 2 and 6 months of age for one experimental test group, according to one embodiment of the present disclosure.

FIGS. 23D-23F show graphs illustrating data plots of percentage of total time spent saccading between 2 and 6 months of age.

FIGS. 24A, 24C, 24E, and 24G show data plots illustrating developmental change in visual fixation with respect to an actor's eyes, mouth, body, or an object, respectively, between 2 and 24 months of age in typically-developing children for one experimental test group, according to one embodiment of the present disclosure.

FIGS. 24B, 24D, 24F, and 24H show data plots illustrating mean fixation curves with 95% confidence intervals for fixation with respect to an actor's eyes, mouth, body, or an object, respectively, between 2 and 24 months of age in typically-developing children for one experimental test group, according to one embodiment of the present disclosure.

FIGS. 25A, 25C, 25E, and 25G show data plots illustrating developmental change in visual fixation with respect to an actor's eyes, mouth, body, or an object, respectively, between 2 and 24 months of age in children with ASD for one experimental test group, according to one embodiment of the present disclosure.

FIGS. 25B, 25D, 25F, and 25H show data plots illustrating mean fixation curves with 95% confidence intervals for fixation with respect to an actor's eyes, mouth, body, or an object, respectively, between 2 and 24 months of age in children with ASD for one experimental test group, according to one embodiment of the present disclosure.

FIGS. 25I-L show data plots illustrating mean fixation curves with respect to an actor's eyes, mouth, body, or an object, respectively, between 2 and 24 months of age in childbirth with ADS for one experimental test group, according to one embodiment of the present disclosure.

FIGS. 26A-26M show graphs illustrating developmental change in visual fixation on the eyes relative to outcome levels of affectedness for one experimental test group, according to one embodiment of the present disclosure.

FIG. 28B shows kernel density estimates plotting the distribution of fixation locations relative to fixation targets to typically-developing children for one experimental test group, according to one embodiment of the present disclosure.

FIG. 28C shows kernel density estimates plotting the distribution of fixation locations relative to fixation targets to children with ASD, for one experimental test group, according to one embodiment of the present disclosure.

DETAILED DESCRIPTION

Figure 1:
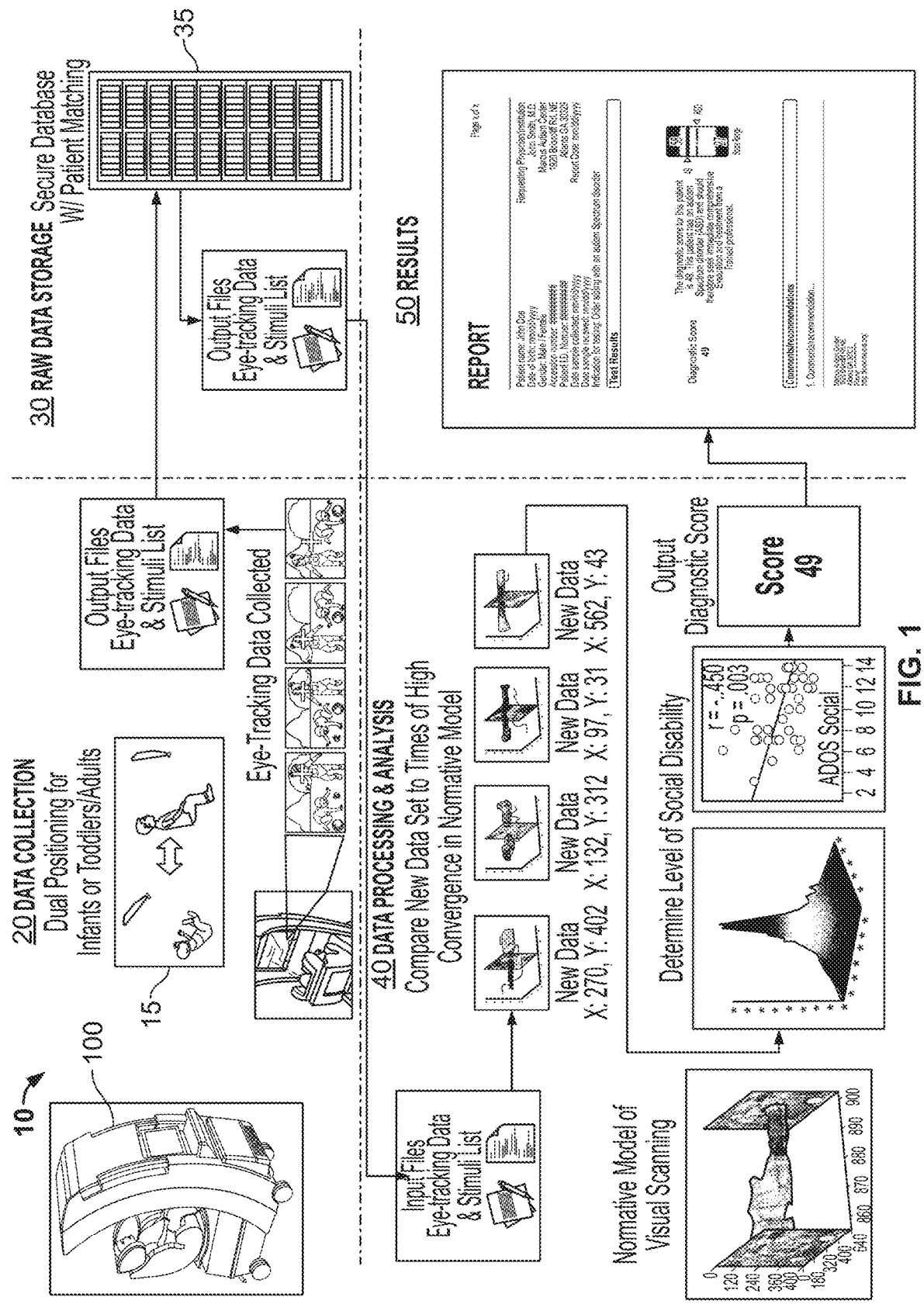
FIG. 1 shows a block diagram of an illustrative system that includes a device and supporting data infrastructure for the delivery of a diagnostic or prescriptive result according to certain embodiments of the present disclosure.

To provide an overall understanding of the systems, devices, and methods described herein, certain illustrative embodiments will be described. In some embodiments (described in greater detail below), the present disclosure relates generally to systems and methods for assessing the risk of developmental disabilities in very young patients (e.g., in the first 2-6 months of life). Although the embodiments and features herein are specifically described for use in connection with collecting and analyzing eye tracking data from subjects for the assessment, screening, monitoring, or diagnosis of autism spectrum disorders (ASD), it will be understood that the systems, devices, and methods may also apply to other developmental, or cognitive, social, or mental conditions, as well as other conditions, including but not limited to expressive and receptive language developmental delays, non-verbal developmental delays, intellectual disabilities, intellectual disabilities of known or unknown genetic origin, traumatic brain injuries, disorders of infancy not otherwise specified (DOI-NOS), social communication disorder, and autism spectrum disorders (ASD), as well as such conditions as attention deficit hyperactivity disorder (ADHD), attention deficit disorder (ADD), post-traumatic stress disorder (PTSD), concussion, sports injuries, and dementia. The present systems, devices, and methods are also applicable to the measurement of developmental, cognitive, social, or mental abilities such as, but not limited to, expressive and receptive language levels in the normative to exceptional range, non-verbal cognitive function in the normative to exceptional range, and social developmental levels in the normative to exceptional range. It will be understood that such data, if not indicating measures for a disorder, may provide a measure of the degree of typicality of normative development, providing an indication of variability in typical development. Further, all of the components and other features outlined below may be combined with one another in any suitable manner and may be adapted and applied to systems outside of medical diagnosis. For example, the interactive visual stimuli of the present disclosure may be used as a therapeutic tool. Further, the collected data may yield measures of certain types of visual stimuli that subjects attend to preferentially. Such measures of preference have applications both in and without the fields of medical diagnosis and therapy, including, for example advertising or other industries where data related to visual stimuli preference is of interest.

All publications, patents, and published patent applications referred to in this specification are specifically incorporated by reference herein. In case of conflict, the present specification, including its specific definitions, will control. Throughout the specification, the term "comprise" or variations such as "comprising" or "comprises" will be understood to imply the inclusion of a stated integer (or component) or group of integers (or components), but not the exclusion of any other integer (or component) or group of integers (or components). The singular forms "a", "an", and "the" include the plurals unless the context clearly dictates otherwise. Furthermore, the terms "patient", "participant", "subject", and "individual" are used interchangeably throughout this disclosure. As used herein, the terms "eye fixation" and "fixation" are generally synonymous with "visual fixation." A visual fixation is a type of eye movement used to stabilize visual information on the retina, and generally coincides with a person looking at or "fixating" upon a point or region on a display plane.

The systems, devices, and method described herein for the detection of developmental, cognitive, social, or mental conditions, including ASD, may be used together with other techniques for processing and analyzing collected eye tracking data including those described, for example, in U.S. Pat. No. 7,922,670, filed Feb. 23, 2006, and entitled "System and Method for Quantifying and Mapping Visual Salience," U.S. Patent Application Publication No. 2014/0192325, filed Dec. 11, 2013, and entitled "Systems and Methods for Detecting Blink Inhibition as a Marker of Engagement and Perceived Stimulus Salience," and U.S. patent application Ser. No. 14/205,012, filed Mar. 11, 2014, and entitled "Systems and Methods for Detection of Cognitive and Developmental Conditions," the disclosures of which are hereby incorporated by reference herein in their entireties.

FIG. 1 shows a block diagram of a system 10 that includes a device 100 and supporting data infrastructure for the delivery of a diagnostic or prescriptive result according to certain embodiments. As depicted, the system 10 is generally divided into four parts (sometimes also referred to herein as systems) related to data collection 20, data storage 30, data processing and analysis 40, and data results 50. In certain embodiments, the system 10 is used to diagnose a developmental, cognitive, social, or mental ability or disability, such as ASD, in subjects or patients. In particular, the system 10 allows for the diagnosis of ASD at a relatively young age, including toddlers and infants as young as six months and younger. In particular, the systems, devices, and methods can reliably collect data for patients of any age, from newborns to the elderly, and use that collected data for the diagnosis of ASD or other cognitive, developmental, social or mental abilities or disabilities. Generally, the system 10 collects and subsequently analyzes eye tracking data to determine a subject's level of social functioning. The system 10 is generally non-invasive. The procedure (also referred to as a "session") associated with collecting eye tracking data can run for any suitable amount of time (e.g., 15 minutes) and generally involves four major steps corresponding to the four parts of the system 10 shown in FIG. 1 (i.e., the data collection system 20, data storage system 30, data processing and analysis system 40, and data results system 50).

As a general overview, first eye tracking data are collected from a subject while he or she watches visual stimuli (e.g., dynamic visual stimuli, such as movies) depicting common social interactions (typically dyadic or triadic interactions) (data collection 20). The stimuli displayed to the subject for purposes of data collection can be any suitable visual image (whether static or dynamic), including movies or videos, as well as still images or any other visual stimuli. It will be understood that movies or videos are referenced solely by way of example and that any such discussion also applies to other forms of visual stimuli. Following the procedure, the eye tracking data, as well as any other suitable information (e.g., a list of the movies that the subject viewed), are transferred to a secure database (data storage 30). The database is preferably remote from the device, to accommodate and aggregate collected data from many devices, but it will be appreciated that in some embodiments the database may be local to the device. After that transfer, the data are again transferred to a central processing computer (local or remote to the database and/or the device) and are processed using custom software written in any suitable programming language (e.g., Matlab) (data processing and analysis 40). In certain embodiments and during the processing step, the data of an individual subject are compared to a statistical model or other relative norm. That comparison outputs a measure (e.g., a score) of social functioning based on that unique subject's own point-of-gaze during the movies he or she viewed (data results 50). That score is compared to predetermined cutoff or other values from the statistical model. In some embodiments, the output of that comparison is a determination of that subject's diagnosis of a developmental, cognitive, social, or mental ability or disability, including ASD, as well as a level of severity of the condition. In some embodiments, the subject's visual fixation (e.g., point-of-gaze data) is tracked over time (e.g., repeated sessions over many months or longer) to determine a change or rate-of-change in visual fixation (the decline of which, especially early in life, can be used as a marker of a developmental condition). In some embodiments, the output of that comparison is a measure of a subject's verbal or non-verbal cognitive skills. In some embodiments, the output of that comparison is a measure of the degree of typicality of normative development, providing an indication of variability in typical development. Additionally, the results may be used to monitor the effectiveness of treatment over time of subjects affected by ASD or other cognitive, developmental, social, or mental conditions. The results of the analysis and the processed files themselves are subsequently uploaded to a database. Typically, the results are made available to the physician (e.g., a pediatrician or other medical professional) or other caregiver of the subject.

In some embodiments, the data collection system 20 includes a mix of hardware and software components. These components together present visual and auditory stimuli to subjects and collect temporally-aligned eye tracking data. The device 100 used for data collection is designed to promote proper subject positioning (e.g., with respect to the subject monitor and eye tracking unit) while also minimizing visual distractions from the subject's field-of-view. Certain details of exemplary systems and devices for performing the methods of the present disclosure will be described with reference to the figures noted below.

FIG. 2 shows front and rear perspective views, respectively, of the device 100 of FIG. 1 according to certain embodiments. The device 100 is generally used for the assessment, screening, monitoring, or diagnosis of developmental, cognitive, social, or mental abilities or disabilities in a subject including ASD (or some other condition). In some embodiments, the device 100 sits atop wheels or casters 108 for efficient mobility across a variety of surfaces. Any suitable wheeled or other movement-facilitating components can be used in place of, or in addition to, the casters 108 to provide mobility. The device 100 is designed to move through standard hallways and doorways on the casters 108 and preferably has a weight (e.g., approximately 250 lbs. or less) that allows maneuverability for operators of all size and strength. The casters 108 may include brakes for securing the device in place when not being moved.

The device 100 also includes a comfortable seat 101 (or support device) for the subject, having a positioning or restraint system (e.g., a seatbelt) for preventing unintended egress from the seat 101 during testing. Any suitable support device may be used for positioning or seating the subject during the procedure, including car seats or high chairs for infants and toddlers, or other types of support devices such as customized chairs for older children and adults. The device has a monitor or display device 103 for viewing by the subject of testing stimuli (including visual images and calibration/fixation targets) and a speaker or other source of audio stimulus 106 for playing audio associated with the testing stimuli. In some embodiments the speakers are integrated with the monitor, although the components may be provided separately. The position of the monitor may be adjustable with respect to any axis of the monitor (e.g., vertical adjustment, horizontal adjustment, and adjustment towards or away from the subject).

As shown, the device 100 further includes an eye tracking unit, device, or sensor 104 for detecting eye movements of a subject in response to a stimulus displayed by the display device 103, operator controls 110, and a baffle or partition 107 for sufficient visual separation of the subject from distractions in the subject's field-of-view. The operator controls 110 are provided together with an operator monitor or display device 109 that allows the operator to observe the subject throughout the procedure via a feed from a video camera 105 that shows the subject and is displayed on the operator monitor 109. Thus, in some embodiments, the operator may be located remotely (e.g., in a different part of the same room or in a different room altogether) from the subject. The device 100 is provided with a control computer 111 for eye tracking collection and stimuli presentation and a power supply unit 112 for powering the components of the device 100. The device 100 is configurable to connect to a network at the physician's office or clinic by direct plug-in or wireless connection. In certain embodiments, the device 100 allows only for outgoing data communication to prevent the introduction of malware. In some embodiments, the device 100 may be formed using a housing or frame structure that supports the various components of the device discussed above.

The support device or seat 101 of the device 100 may be adjustable to position the subject in an orientation with respect to the display device 103 and the eye tracking sensor 104 that allows for collection of eye movement data. And the seat 101, once positioned, may confine the subject in that particular orientation. This allows for the seat to operate in repeatable positions (whether from subject-to-subject or for multiple sessions with the same subject). For example, in some embodiments, the device 100 operates in two modes (an "infant mode" and a "toddler mode") such that the monitor 103 and seat 101 orientation can accommodate toddlers (who, like adults, prefer sitting upright) and infants (who prefer to be reclined). The dual positions for infants or toddlers/adults are shown in the insert 15 for the data collection system 20 of FIG. 1. Because there are many possible positions that can be used and that are repeatable from subject to subject, it will be understood that the seat may have any suitable number of "modes" and may be further positionable/adjustable. For example, embodiments of the device 100 have a swivel mechanism 102 for subject ingress/egress that can also be used for orienting the subject with respect to the display device 103 and the eye tracking unit.

The device 100 of FIG. 2 may be used for data collection 20, outlined above, such that (1) a subject is seated in front of a display screen (e.g., a computer monitor) on which varying dynamic videos and other stimuli are played for the subject, (2) an operator is able to control software which will (a) calibrate an eye tracking unit to the subject, (b) validate that the calibration is accurate, and (c) collect eye tracking data from the subject as he or she watches the dynamic videos or other visual stimuli. After this part of the procedure, generally referred to as "data collection," the subject's data may be transferred to a secure database. The database is preferably remote from the device, to accommodate and aggregate collected data from many devices, but it will be appreciated that in some embodiments a database may be local to the device. In some embodiments, receipt of the collected data by the database initiates an automatic software-implemented processing and analysis process in which the subject's individual data are compared to models of eye tracking data which were previously generated from historical eye tracking data. The result of the comparison is a diagnostic and/or prescriptive measure of the subject's developmental functioning. In other embodiments, the collected data is compared reviewed for a given subject over multiple sessions (and over a predetermined time period) to identify a potential change in visual fixation (e.g., a decline in visual fixation). Those results may be condensed into a diagnostic report for use by the subject's physician.

Generally, the device operator (e.g., a medical assistant or other medical professional) needs only minimal training to operate the device. The device is designed to allow for repeatable proper positioning of the subject in front of a display device (e.g., display device 103 of FIG. 2). After entering the operator's and subject's information into the custom software platform running on the device, the software selects age-specific stimuli (e.g., movies) and instructs the operator to position the display device in front of the subject at proper orientation. Then, a calibration procedure is performed to calibrate the subject to the eye tracking device (e.g., eye tracking device 104 of FIG. 2). Subsequent to a valid calibration (determined by the software), the software begins the data collection process by selecting videos that are played for the subject via the display device, and raw eye tracking data (from the subject moving his or her eyes in response to predetermined movies or other visual stimuli) is collected. Both the eye tracking data and information relating to the stimuli (e.g., a list of the stimuli viewed by the subject) are then transferred to a secure database for processing.

The movies that are displayed to a subject may be dependent on the subject's age. In some embodiments, the device measures the amount of fixation time a subject (positioned in the seat) spends looking at an actor's eyes, mouth, or body, or other predetermined region-of-interest, and the amount of time that subject spends looking at background areas in the video. Video scenes, shown to the subject via the display device, may depict scenes of social interaction (e.g., an actor looking directly into the camera, trying to engage the viewing subject, for instance, or scenes of children at play). In some embodiments, the video scenes can include other suitable stimuli including, for example, animations and preferential viewing tasks. Measures of fixation time with respect to particular spatial locations in the video may relate to a subject's level of social and/or cognitive development. For example, children between ages 12-15 months show increasing mouth fixation, and alternate between eye and mouth fixation, as a result of their developmental stage of language development. As another example, a decline in visual fixation over time by a subject with respect to the eyes of actors in videos may be an indicator of ASD or another developmental condition in the subject.

Analysis of the subject's viewing patterns (during the displayed movies and across a plurality of viewing sessions) is performed for the diagnosis and monitoring of a developmental, cognitive, social or mental ability or disability including ASD. During this data collection period, the system periodically shows calibration or fixation targets (that may be animated) to the subject. These data are used later to verify accuracy. The testing methodology depends on the subject being awake and looking at the screen. During both the calibration as well as the data collection procedures, predetermined movies and/or other visual stimuli are presented to the subject via the display device. These movies and/or other visual stimuli may include human or animated actors who make hand/face/body movements.

Any suitable eye tracking unit and associated software may be used with the systems, devices, and methods of the present disclosure. For example, various commercially available eye tracking units may be used, including those eye tracking units commercially available from SensoMotoric Instruments (e.g., model RED-m), ISCAN Inc. (e.g., model RK-464), and Tobii Technology (e.g., model X60), or any other suitable eye tracking unit from other manufacturers. In certain embodiments, master software code such as that developed by the applicants of the systems, devices, and methods disclosed herein is used to supervise or control the steps of the eye tracking software and is additionally used to perform other functions. Examples of such functions include presenting an interface to the operator showing the subject's name, date of birth, etc., information relating to the stimuli (e.g., movies) that are shown to the subject, and the like. In some embodiments, the master software code interfaces with the eye tracking software via a software development kit (SDK).

According to some embodiments, the computer that facilitates the diagnostic testing session is a special purpose computer with high processing abilities (e.g., because of the relatively high volume of video involved in the testing process). Eye tracking data are collected by the computer and stored in a data file (e.g., as .idf data) that is then transmitted via a secure network connection from the physician's office to a central database and processing computer for analysis. At the processing facility, offline analysis of the data may be performed by analyzing the eye tracking data (received from a subject tested at the physician's office) in relation to a model created from historical data (e.g., using data previously collected from subjects known to have ASD or other developmental, cognitive, social, or mental conditions and also healthy controls). As discussed throughout this disclosure, however, it will be understood that in some embodiments the processing and analysis steps may be performed in real time during the session by a computer local to the device.

Figure 3A:
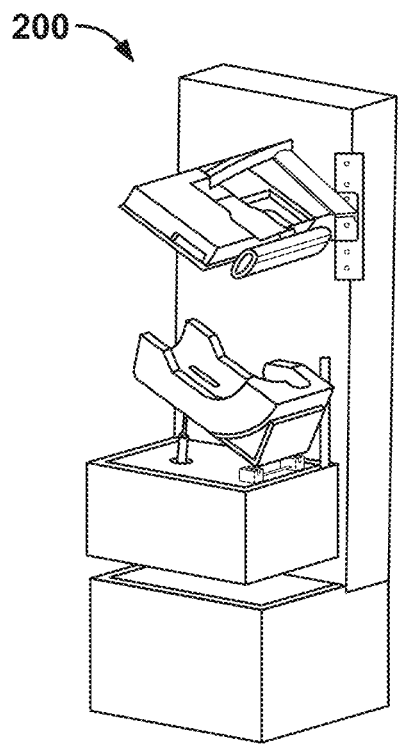
FIGS. 3A to 3F show perspective views of alternate embodiments of the device of FIG. 2 according to certain embodiments of the present disclosure.
Figure 3B:
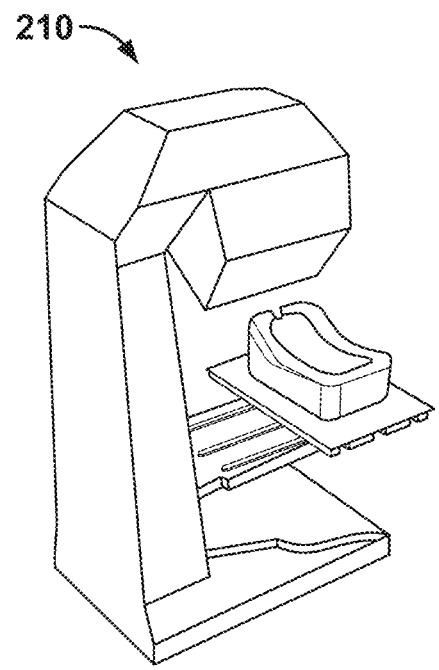
Figure 3C:
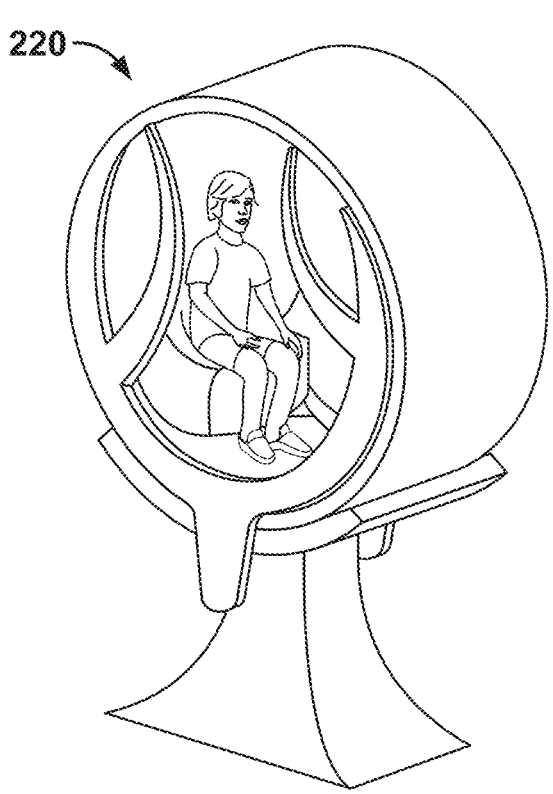
Figure 3D:
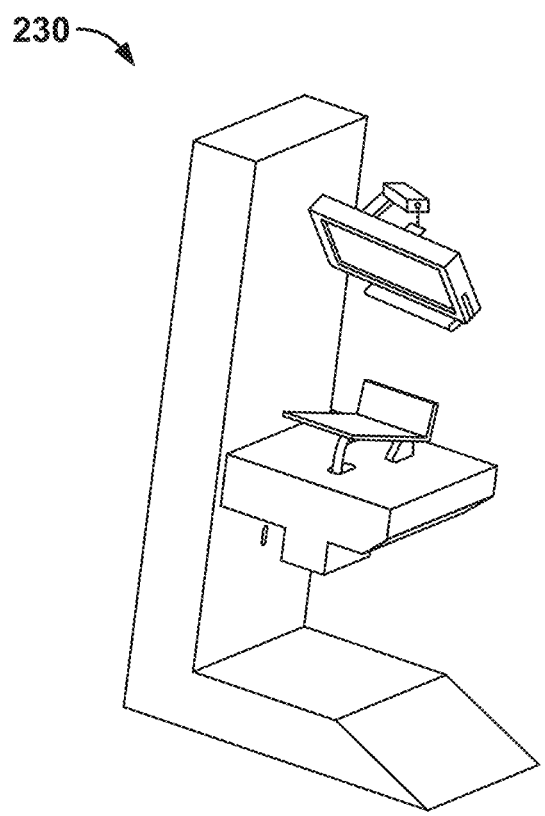
Figure 3E:
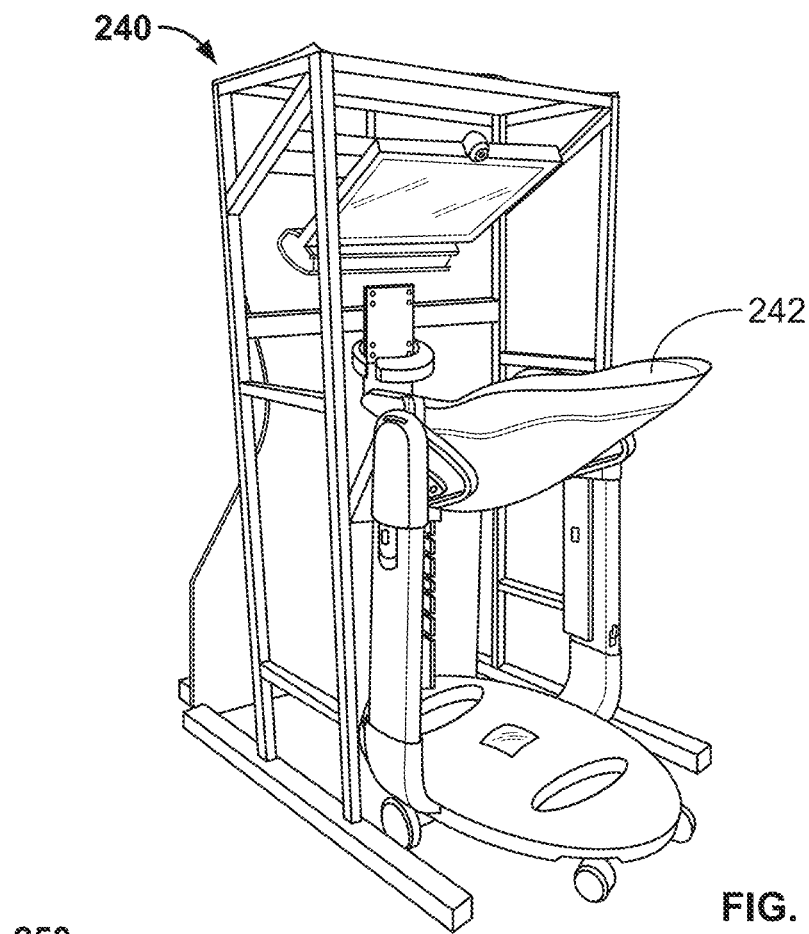
Figure 3F:
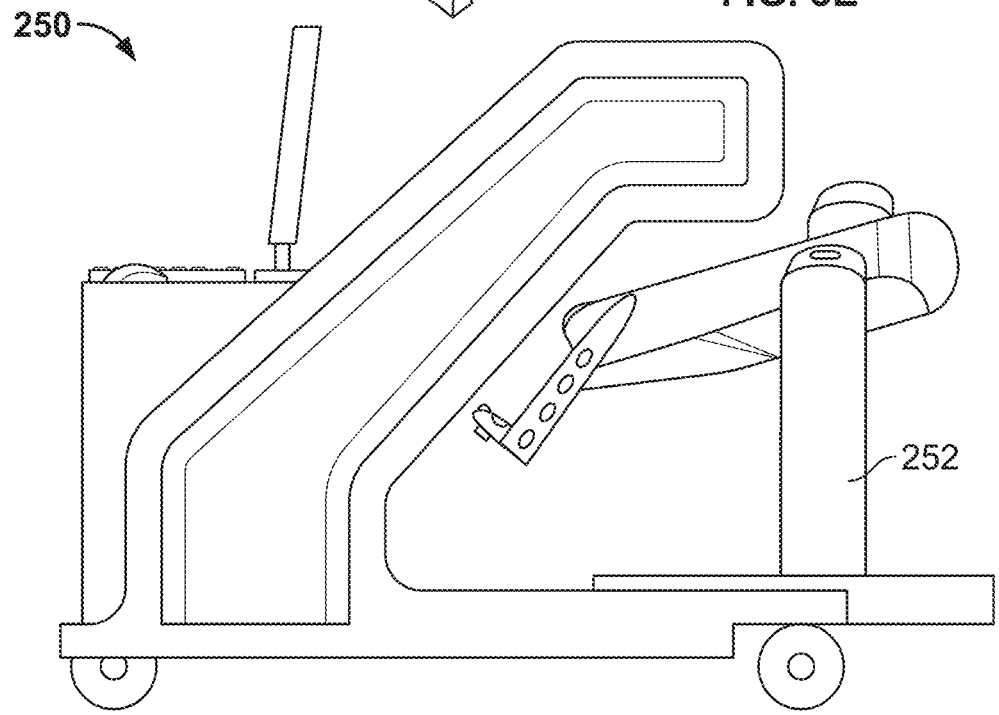

There are many possible modifications or alterations that can be made to the device 100 without affecting the manner in which the eye tracking data are collected, stored, analyzed and processed. In each case the modified or altered device provides for data collection and proper subject positioning (e.g., with respect to the subject monitor and eye tracking unit) while also minimizing visual distractions from the subject's field-of-view. FIGS. 3A to 3F show perspective views of alternate embodiments (A) through (F) of the device 100 of FIG. 2. For example, in some embodiments, the device is stationary (that is, the device is not mobile). The device may be permanently or semi-permanently secured to the floor (e.g., fixed in place in use), or the device may not include casters or wheels, and the weight of the device thus keeps it in place. As shown in FIGS. 3A through 3E, the respective devices do not include casters or wheels. In some embodiments, the support device (e.g., seat 101 of FIG. 2) may be separable from its respective device (whether or not the device itself is mobile or stationary). For example, the seat in which the subject is positioned may be slidably adjustable via a rolling mechanism. As shown in FIG. 3E, the device 240 is stationary but the support device 242 is mobile. As another example, in FIG. 3F, the device 250 is mobile and the support device 252 is also mobile.

According to certain embodiments, any of the devices of the present disclosure, including those discussed above in FIGS. 3A to 3F, may include (1) a seat for the subject that can be adjusted depending on the subject's age, (2) a mechanism for rotating the seat towards or away from the device, (3) a display device (that, manually or using an electrical motor can be adjusted for varying subject heights)

for showing the subject movies or other visual stimuli, (4) an eye tracking unit focusing a camera on the eyes of the subject and illuminating them with a safe amount of infrared or other electromagnetic energy, (5) a camera for the operator's use to monitor the general well-being and compliance of the subject, (6) one or more speakers which produce sound, (7) a mechanical system (optionally electrically powered) for positioning the display device, eye tracking unit, and any other components, (8) swiveling casters with brakes, (9) a monitor (e.g., touch-screen) for an operator operating the device, (10) a keyboard and mouse for the operator, (11) a control computer with custom software, (12) a power supply for delivering power to the various components of the device, and (13) a welded, sheathed mechanical frame to hold all of the components together.

In some embodiments, the above components (1)-(13) are aligned in a common frame of reference (e.g., the welded sheathed mechanical frame mentioned above or any other suitable housing or enclosure) such that they can be positioned or transported together. This frame of reference may be a static, custom designed metallic support structure. In some embodiments, the metallic support structure comprises welded tubular members arranged vertically, horizontally, and/or angularly to create the support frame and testing region; the seat is positioned inside the testing region with the subject positioned in proximity to the display device but shielded by most external distractions by a baffle or partition. The operator of the device may stand outside the framework in a position so as to oversee the subject via an operator computer, and observe the subject through the monitoring camera. The subject (positioned on the support device) is preferably unable to see the operator because the subject's view is obstructed by the partition. The partition may be formed of plastic-like material that is easy to clean and that is heat-molded to the metal framework. As shown in FIGS. 3A to 3F, for example, the devices have frames that support all or some of the components of the respective device.

Figure 4:
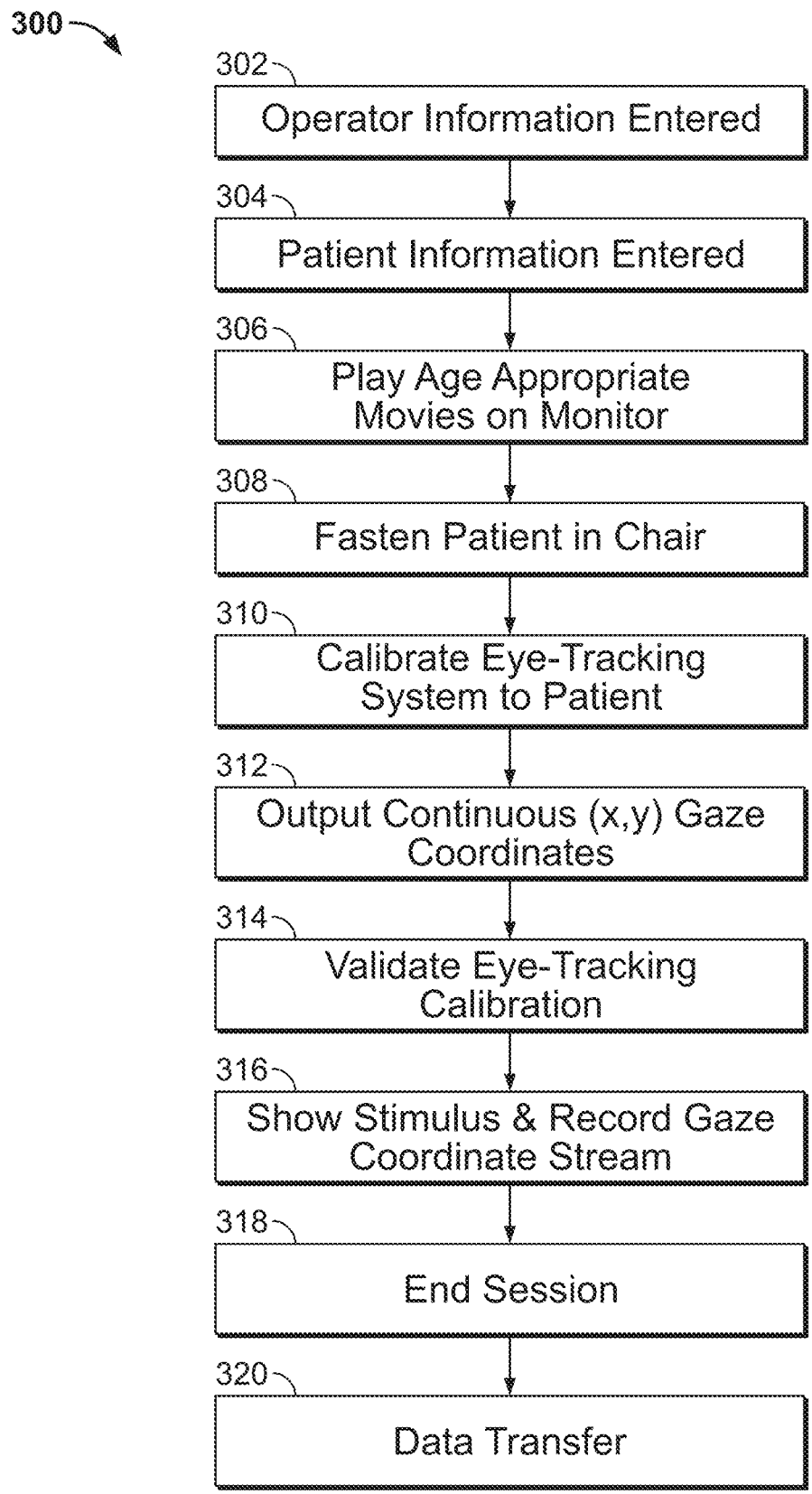
FIG. 4 shows an illustrative flowchart for data collection according to certain embodiments of the present disclosure.

FIG. 4 shows a flowchart 300 for data collection according to certain embodiments. In some embodiments, the data collection is accomplished using a custom-developed software application implemented with any of the devices, such as device 100 of FIG. 2, of the present disclosure. Certain steps of the process are computer-implemented functions implemented in software code associated with a computer that operates the disclosed device (e.g., computer 111 of FIG. 2). FIGS. 5A through 5L show a series of display screens that are presented to an operator (e.g., via operator monitor 109 of FIG. 2) during the data collection according to certain embodiments and will be referenced together with the discussion of the steps of process 300. It will be understood that the steps of the flowcharts of this disclosure are merely illustrative. Any of the steps of the flowcharts may be modified, omitted, or rearranged, two or more of the steps may be combined, or any additional steps may be added, without departing from the scope of the present disclosure.

In certain embodiments, a custom-developed software application enables the device operator to (a) associate a testing procedure with a specific subject, (b) calibrate eye tracking data collection equipment to the subject, (c) present video and audio stimulus on the subject stimulus monitor and speakers, and (d) collect eye tracking data (e.g., x,y coordinates of gaze) from the subject as related to the visual and audio stimulus. In some embodiments, at the end of the session, the collected data are transferred to a central database (e.g., process 1000 of FIG. 12) for further processing and analysis (e.g., process 1050 of FIG. 13).

Figure 5A:
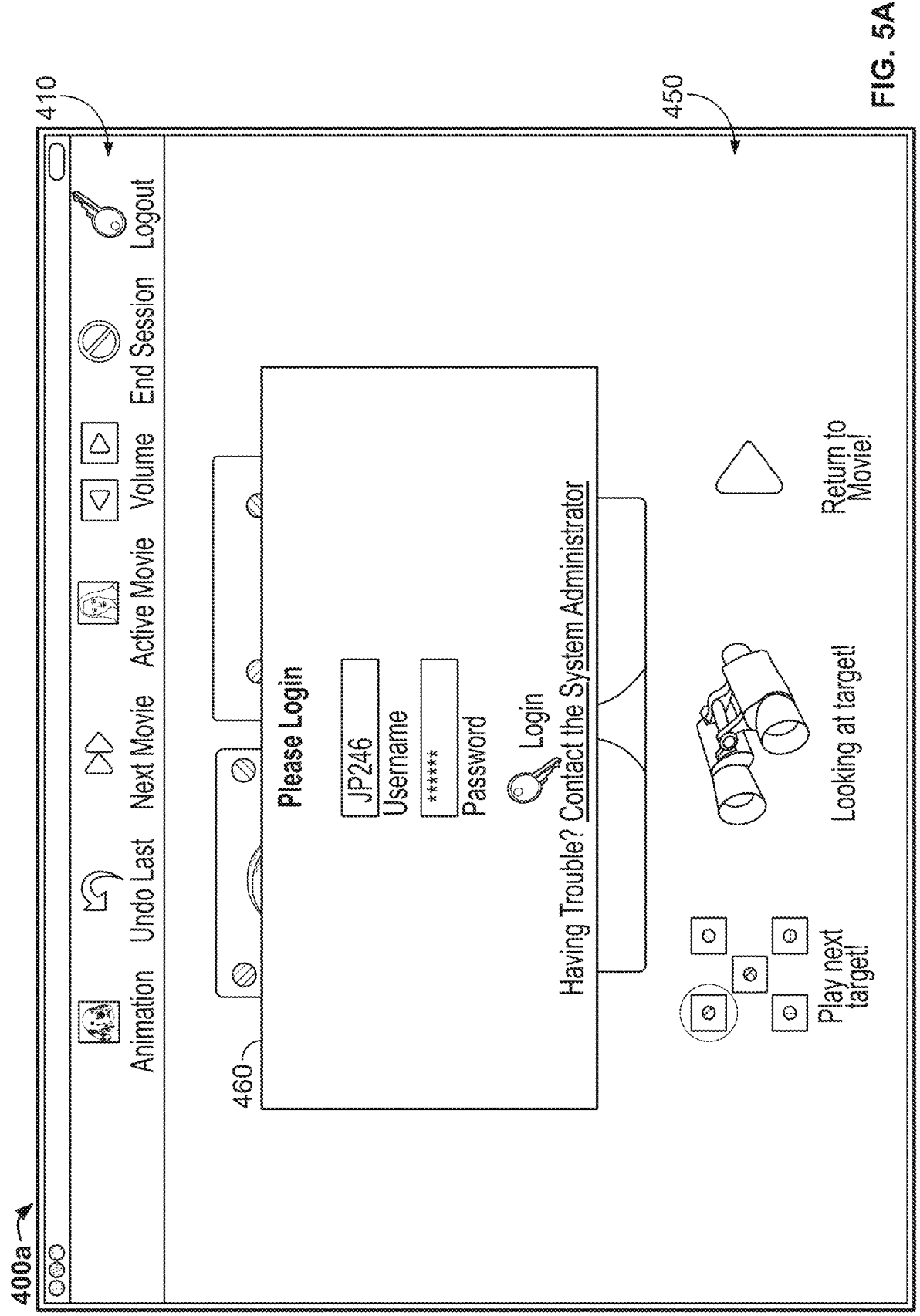
FIGS. 5A to 5L show a series of illustrative display screens that are presented to an operator during certain data collection processes according to certain embodiments of the present disclosure.

Process 300 begins at step 302, where operator information is entered (e.g., via operator controls 110 of FIG. 2). The information may be any suitable information that allows for identification of the operator. For example, the operator's first and last name may be recorded. The first and last name may be associated with a username for the purposes of logging into the system as well as identifying the operator. In some embodiments, the operator information is queried in a database (e.g., database 35 of FIG. 1) to monitor site utilization and operator-dependent data quality variations (although this is expected to be low). As shown in FIG. 5A, a display screen 400a includes an overlay 460 that allows the operator to log into the system using a username and a password. The display 400a also includes a banner bar 410 with various buttons (e.g., Animation, Undo Last, Next Movie, Active Movie, Volume, End Session, Logout) available throughout the session to navigate through portions of the session or control other functions of the session. Also presented at the bottom of the display 400a are contextual buttons 450 (e.g., Play next target, Looking at target!, Return to movie!) that relate to functions available for a particular mode of the application currently in session (e.g., display 400a has different contextual buttons 450 than those in display 400j).

Figure 5B:

At step 304 subject information is entered. The information may be any suitable information that allows for identification of the subject and any other information relevant for the purposes of data processing and analysis. For example, the subject's first and last name, date of birth, gender, and primary language may be entered. The subject information is used to link a given session's data to an individual record in the database. As shown in FIG. 5B, a display screen 400b includes an overlay 462 that allows the operator to enter subject information into various fields including those discussed above. Also shown in the overlay 462 is a "Session ID" that allows for indexing the collected data in the database according to sessions associated with respective subjects.

Figure 5C:
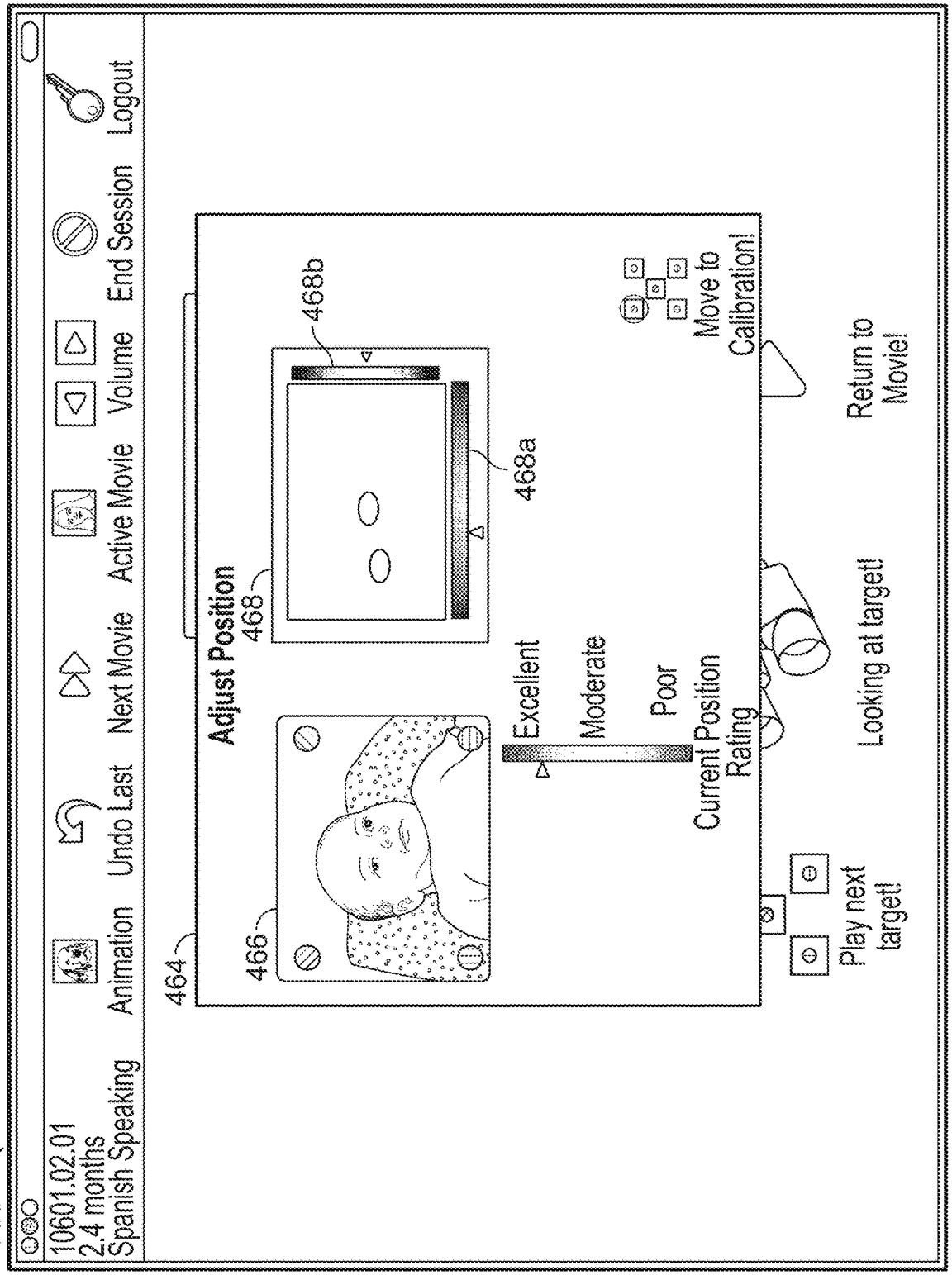

At step 306 age appropriate or age-specific stimuli (e.g., movies) are played on a monitor. This display attracts the subject's attention to the monitor (e.g., display device 103 of FIG. 2) and allows the operator or the subject's caregiver, at step 308, to fasten the subject in the chair. In certain embodiments, the application instructs the operator to (a) adjust the monitor and chair angle based on the subject's age, (b) place the subject in the chair and securely fasten the seatbelt, and (c) confirm that the eye tracker can identify the subject's eyes. As shown in FIG. 5C, a display screen 400c includes an overlay 464 for observing the position of the subject (using video window 466) and confirming that the subject's eyes are being identified by the eye tracker (using video window 468). The video window 466 shows a video feed of the subject and depicts the location of where fixation targets will be displayed relative to the position of the subject. The video window 468 shows whether the subject's eyes have been identified by the eye tracker, and provides feedback (elements 468a and 468b) on the current position rating. In some embodiments, the position rating is color coded to represent excellent, moderate, or poor positions.

Figure 5D:
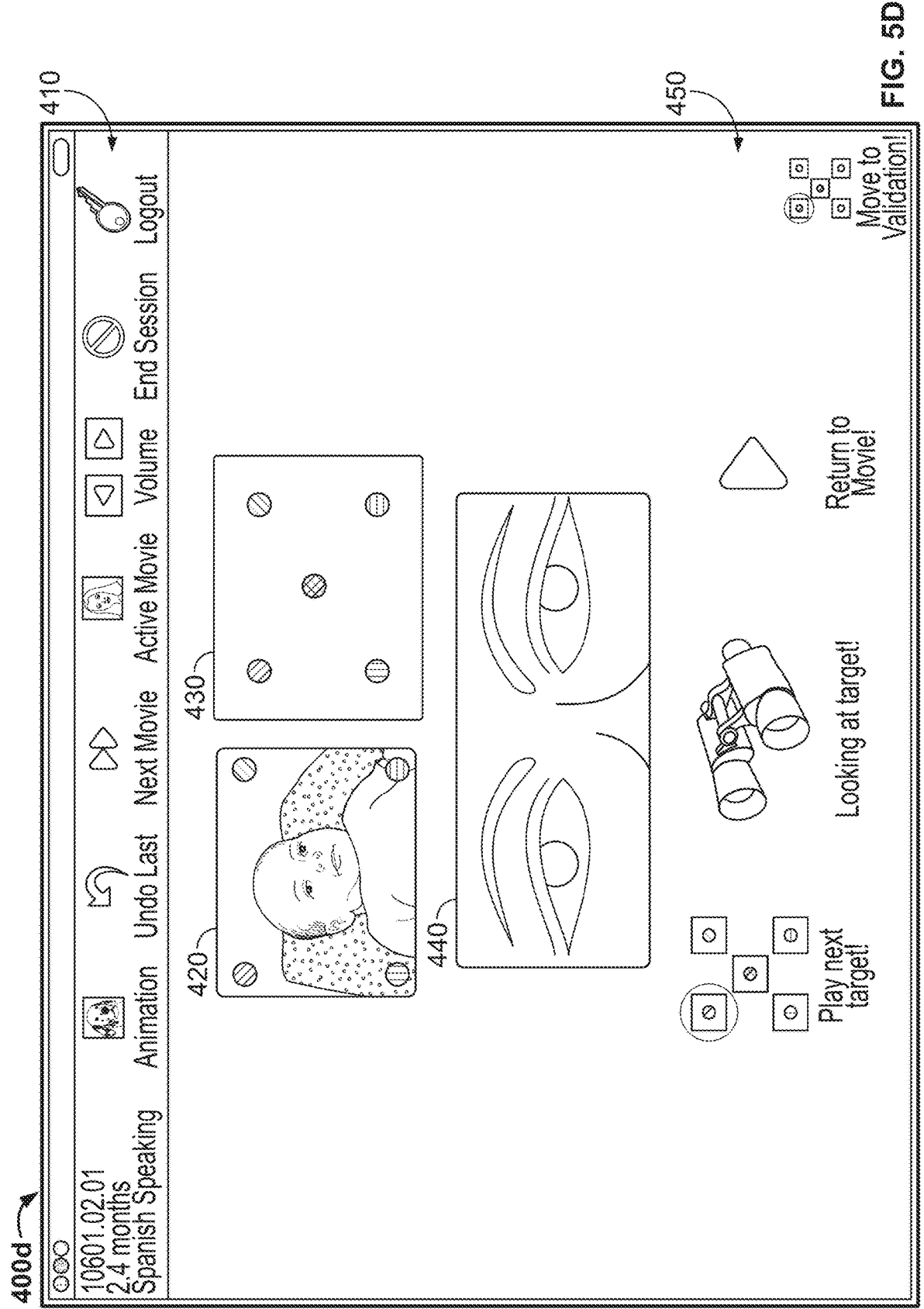
Figure 5E:
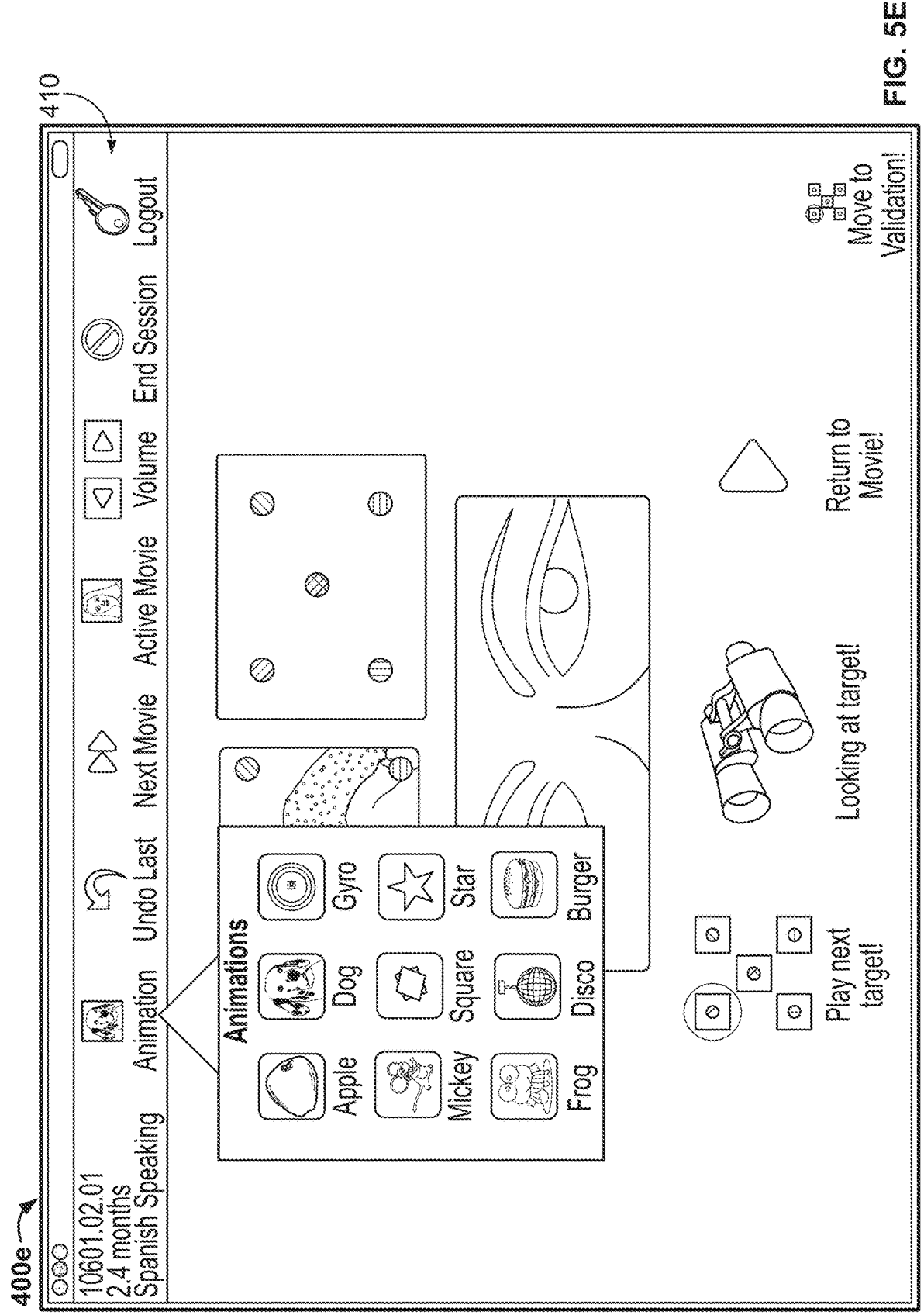

At step 310 the eye tracking system is calibrated to the subject. The operator maintains constant visual monitoring of the subject via a camera feed. In certain embodiments, when calibration targets, also called fixation targets, are presented to the subject, both the operator and the eye tracking unit (e.g., eye tracking unit 104 of FIG. 2) confirm that the subject is fixating. The targets reflexively capture the subject's attention and result in a saccade towards, and fixation upon, a known target location. The target reliably elicits fixations to a finite location; for example, a radially symmetric target spanning less than 0.5 degrees of visual angle. Other examples include concentric patterns, shapes, or shrinking stimuli that, even if initially larger in size, reliably elicit fixations to fixed target locations. As shown in FIG. 5D, a display screen 400d includes a video window 440 showing that the operator maintains constant visual monitoring of the subject, who is monitored via a camera feed in window 420. Overlaid over the camera feed in window 420 are the locations of calibration targets, or fixation targets, that are sequentially presented to the subject. The operator can visually confirm, by looking at video window 420, that the subject is fixating on a displayed target and then manually indicate the observed fixation using an input device. The video window 430 has targets that are overlaid over a feed that depicts information from the eye tracking equipment. Any suitable icon can be used as a calibration or fixation target, and the targets may be static or dynamic. For example, as shown in the display 400e of FIG. 5E, selection of the "Animation" button from banner bar 410 results in the display of a list of possible animations that can used as fixation targets. Dynamic or animated fixation targets may reflexively cause exogenous cueing by the subject without the need for verbal mediation or instruction by the operator. For example, the operator need not give instructions to look at the dynamic target because the target itself captures the subject's attention.

Figure 5F:
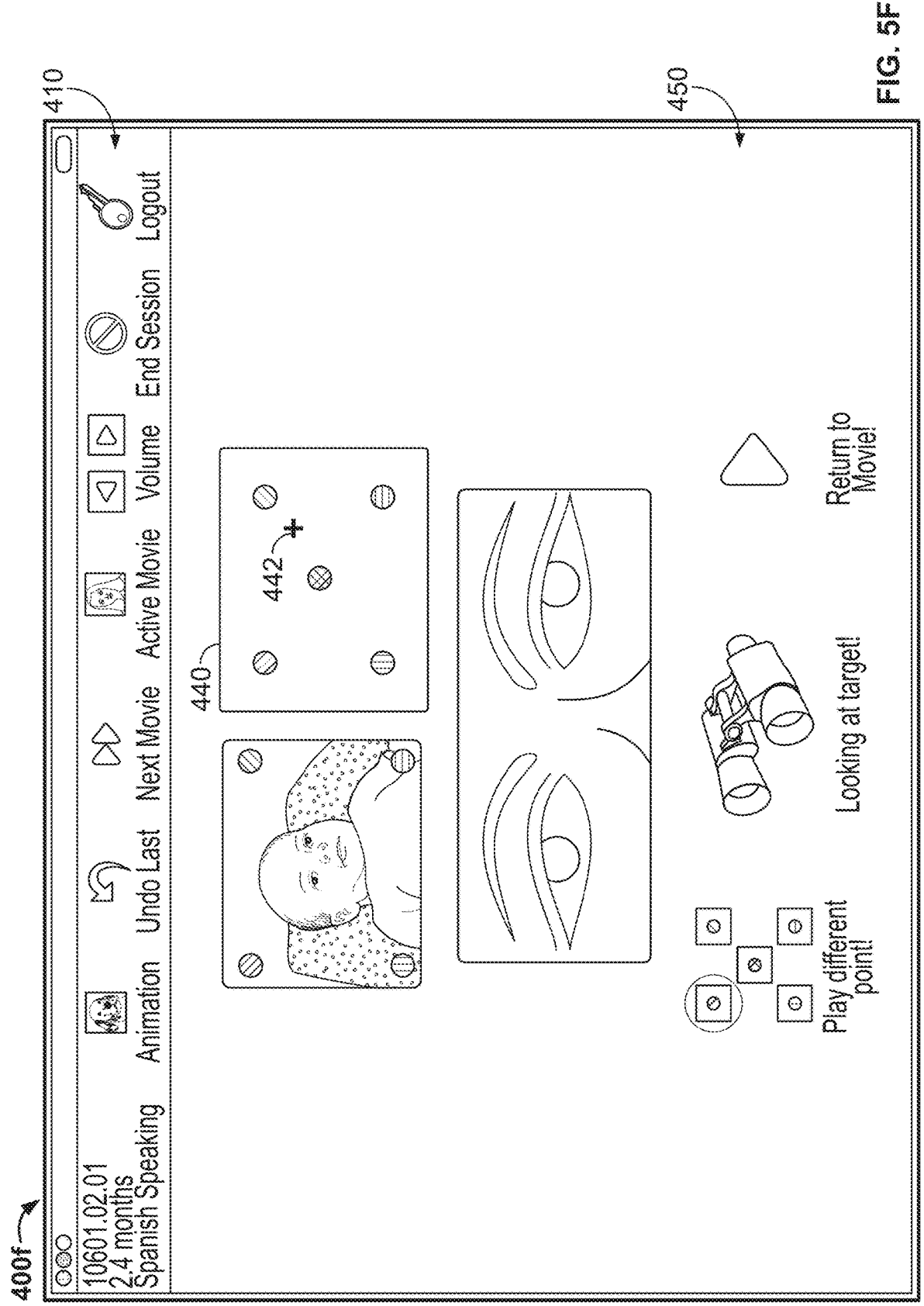
Figure 5G:
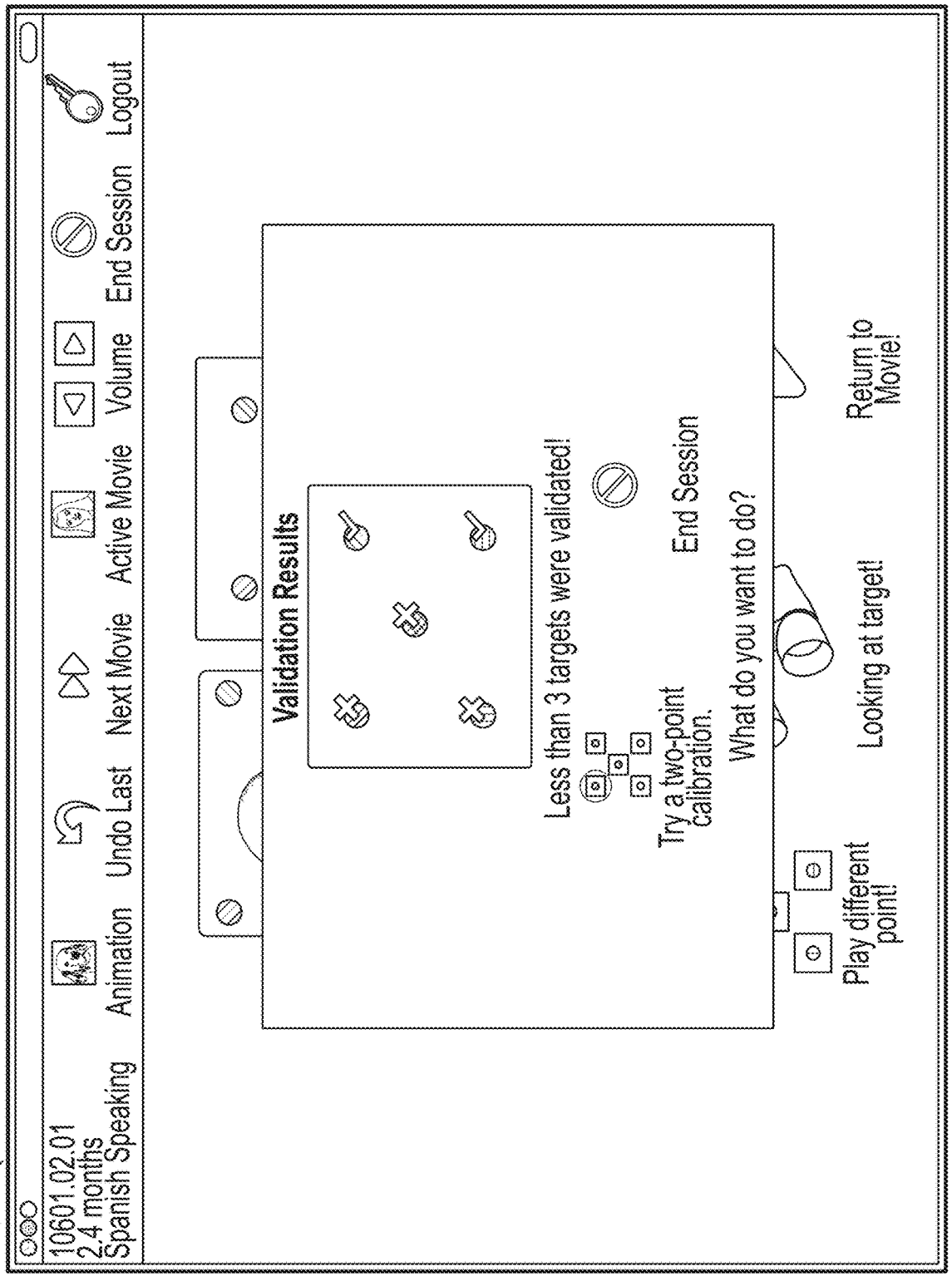
Figure 5H:
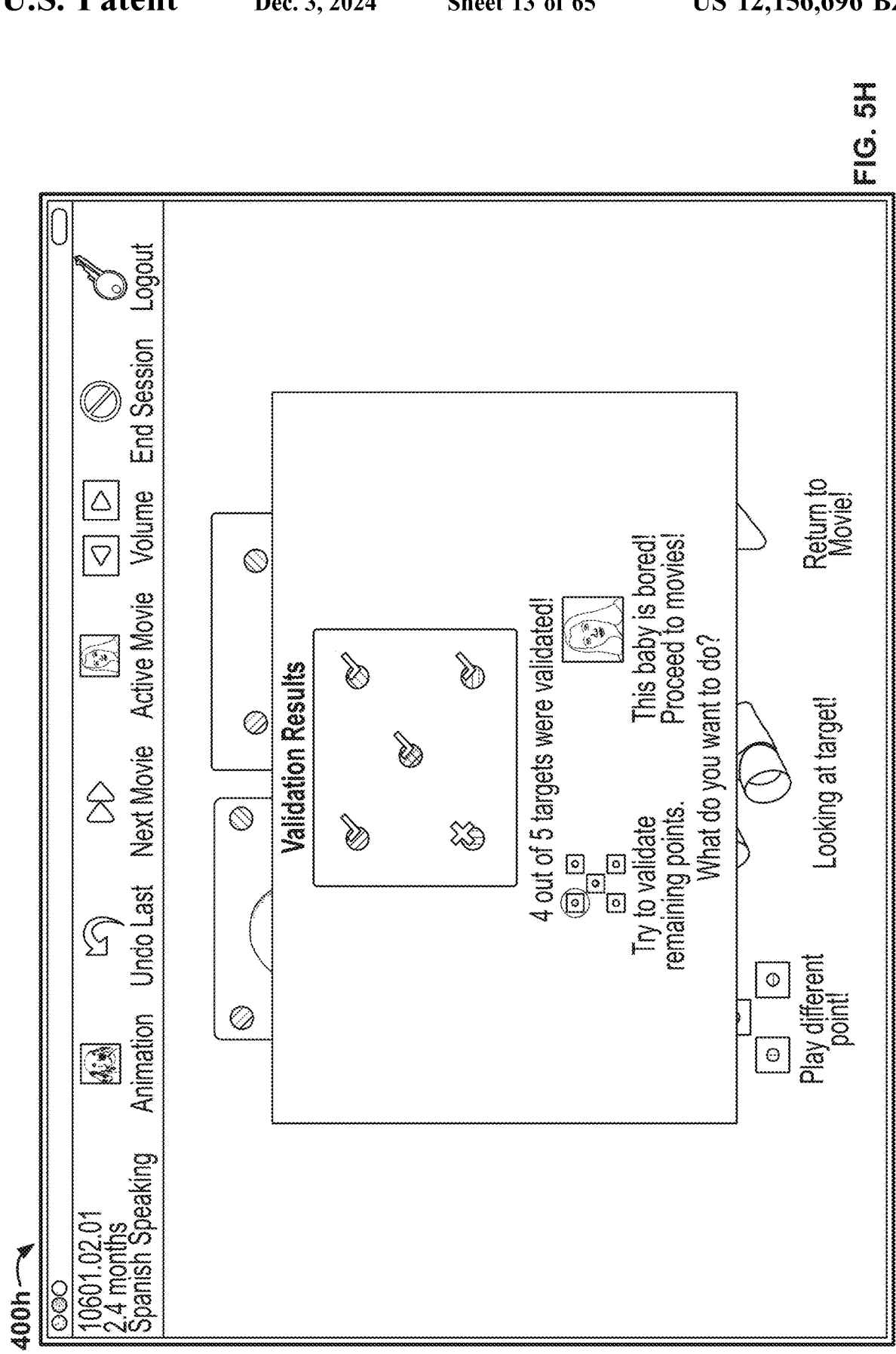
Figure 5I:
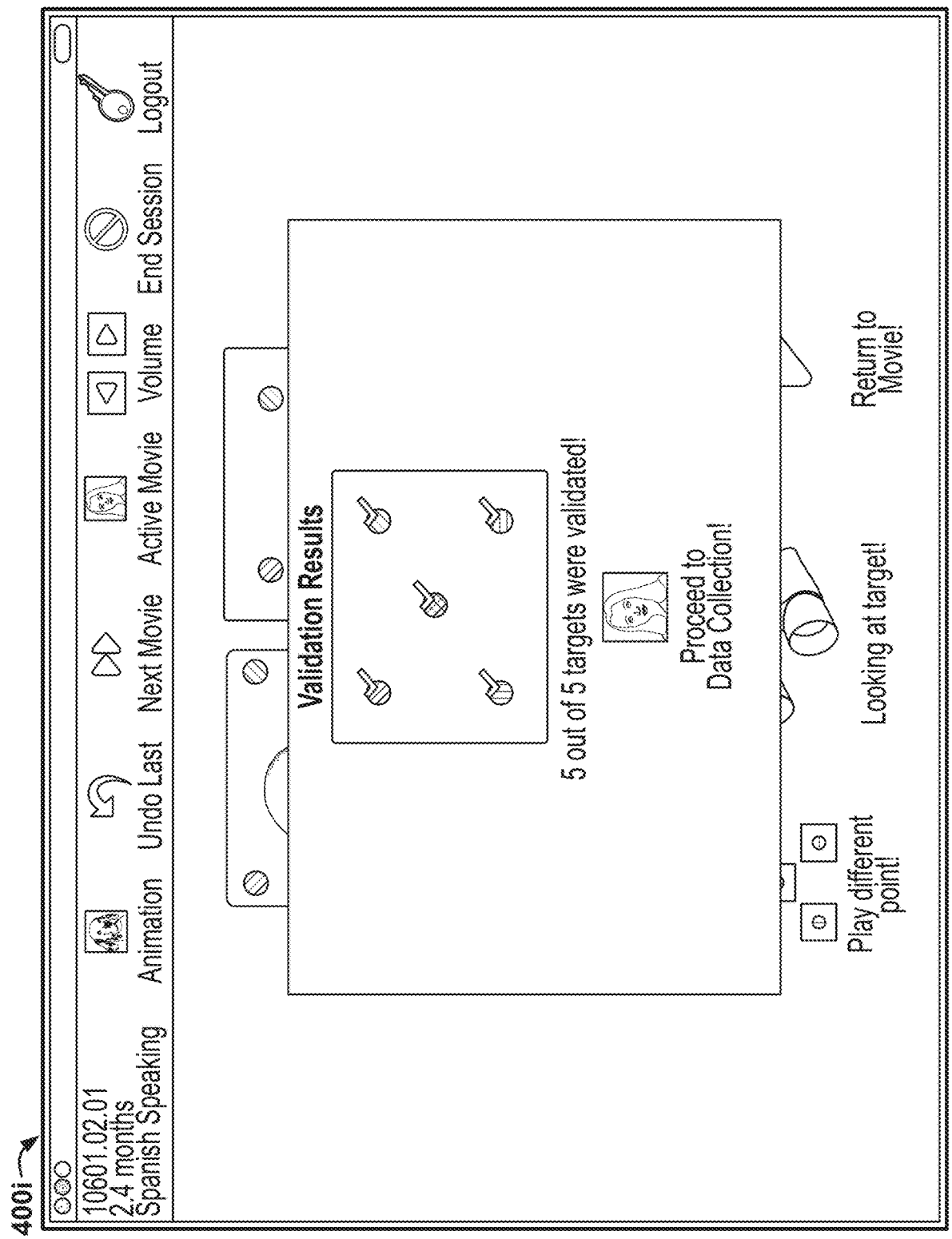
Figure 5J:
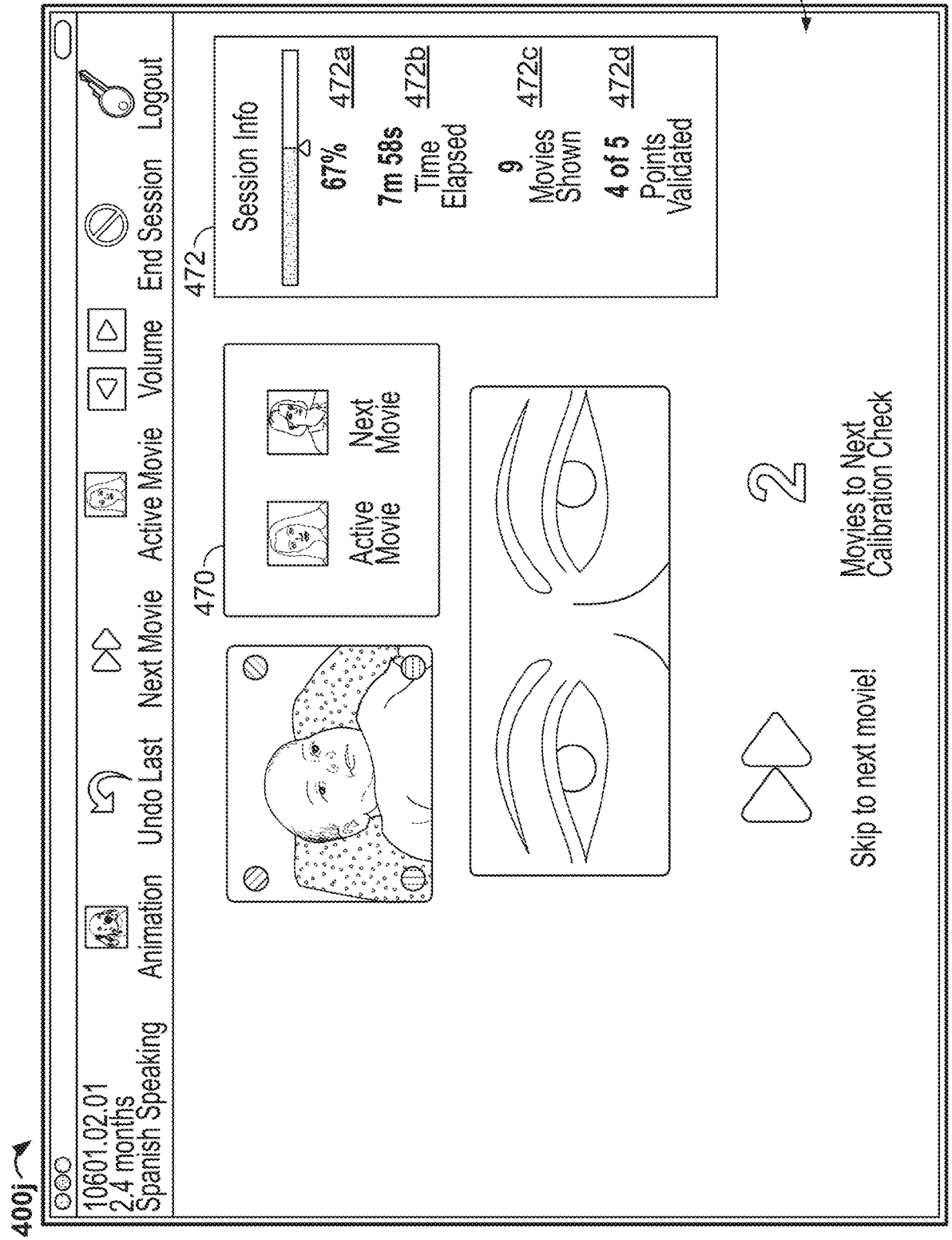
Figure 5K:
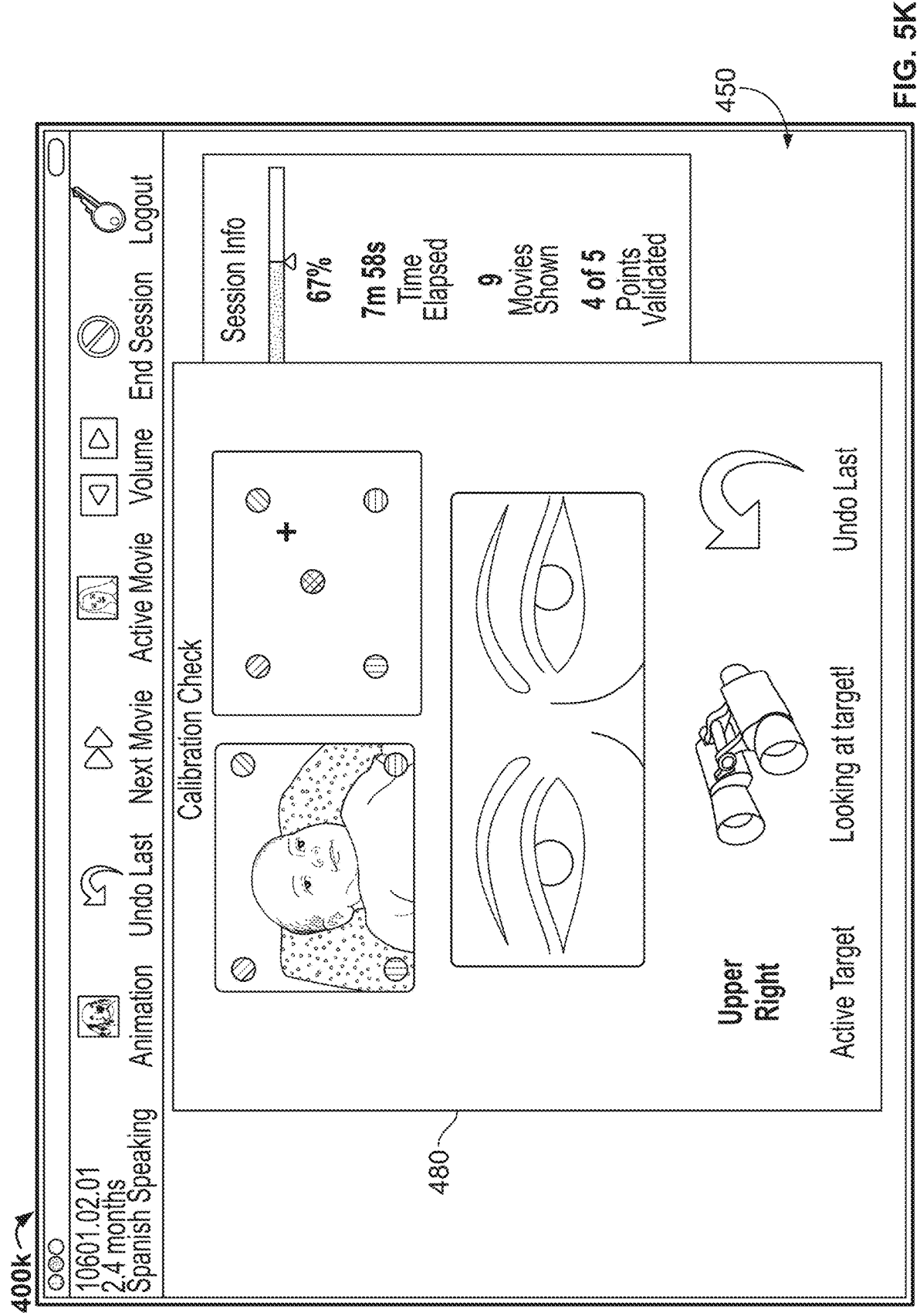
Figure 5L:
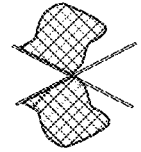

At step 312 continuous (x,y) gaze coordinates are output from the eye tracking equipment (e.g., eye tracking device 104 of FIG. 2). After a sufficient number of fixations towards calibration targets have been registered, a continuous stream of (x,y) gaze position coordinates are outputted, for example, at 120 Hz or any other suitable rate. As shown in FIG. 5F, the display 400f includes a gaze position coordinate 442 in the eye tracking video window 440. As the subject continues to look at the display device (before, during, or after the display of a stimulus), the eye tracking equipment outputs continuous gaze position coordinate for later data processing and analysis. As generally discussed herein, a subject's visual fixation can be defined in terms of point-of-gaze data (or gaze position coordinates), i.e., a spatial position at which a subject is looking.

Accuracy of collected eye tracking data can be assessed via the presentation of visual stimuli that reflexively capture attention and result in a saccade towards, and fixation upon, a known target location. The target reliably elicits fixations to a finite location; for example, a radially symmetric target spanning less than 0.5 degrees of visual angle. Other examples include concentric patterns, shapes, or shrinking stimuli that, even if initially larger in size, reliably elicit fixations to fixed target locations. Such stimuli may be tested under data collection with head restraint to ensure that they reliably elicit fixations under ideal testing circumstances; then their use can be expanded to include non-head-restrained data collection.

To ensure that the collected data are accurate, at step 314, the eye tracking calibration is validated. This step can occur immediately after the initial calibration, or this step can occur after a stimulus has been presented to the subject (e.g., after several movies have been shown). In some embodiments, additional fixation targets are shown to the subject and the outputted eye tracking data are compared to the known target location to assess data accuracy. The software application may instruct the operator to recalibrate if data quality is not sufficient. For example, as shown in the display 400g of FIG. 5G, less than three (of five) targets were validated and the operator is instructed to try a two-point calibration or end the session. As shown in the illustrative display 400h of FIG. 5H, four out of five targets were validated and the operator is instructed to try to validate the remaining points or to proceed (or continue with) display of stimulus. As shown in the illustrative display 400i of FIG. 5I, five out of five targets were validated and the operator is instructed to proceed with data collection. It will be understood that any suitable number of targets may be displayed and may be used for calibration and/or validation of the eye tracking device. For example, in some embodiments, two-point calibration and validation may be used for the collection of reliable eye tracking data.

At step 316 the stimulus is shown to the subject and a gaze coordinate stream is recorded. In certain embodiments, the gaze coordinate stream includes data sampled at a given frequency (e.g., 60 Hz, 120 Hz, 512 Hz, 1000 Hz, or any other suitable frequency) that indicates the instantaneous gaze position coordinates of the subject with respect to a display (e.g., display 103 of FIG. 2) for a given period of time (e.g., duration of a visual stimuli). Following successful validation (at step 314), stimuli (e.g., movies depicting common dyadic and triadic social interactions) are presented to the subject. Gaze position coordinates are recorded temporally in association with the stimuli presentation. For example, as shown in the display 400j of FIG. 5J, a window 470 indicates the current "Active Movie" and the "Next Movie" being displayed to the subject. Another window 472 has information on the current session, including the percentage completion 472a, time elapsed 472b, number of movies shown 472c, and number of points validated 472d. The contextual buttons 450, as noted previously, are different than those displayed in earlier displays, and give the operator the option to skip to the next movie as well as indicate the number of movies until the next calibration check. As discussed above with respect to step 314, the validation of eye tracking calibration can occur immediately after the initial calibration, and/or validation can occur after a stimulus has been presented to the subject. In the display 400k of FIG. 5K, a calibration check is performed after a stimulus has been presented to the subject (in this case, after nine movies were shown). An overlay 480 is displayed that includes similar windows to those discussed above with respect to FIG. 5F. The contextual buttons 450 indicate that the current active target is the "Upper Right" target.

At step 318 the session is ended when sufficient data has been collected or if the subject becomes fussy or otherwise uncooperative (e.g., given that subjects are often young children, toddlers, and infants). The reason for the procedure's end may be recorded and the operator is instructed to remove the subject (or have the subject's caregiver remove the subject). As shown in the display 400l of FIG. 5L, an overlay 490 is generated that asks several questions of the operator, including the reason for the end of the session and a questionnaire with rankings for various events during the session. Also shown is a summary 492 of various statistics for the current session, including the percentage of data requirements met, time elapsed, movies shown, calibration checks shown, and the number of calibration targets validated. Any other suitable metrics related to the session may be displayed.

According to certain embodiments, the systems, devices, and methods described herein do not require verbal mediation to instruct the subject about what to do during a given session. That is, the eye tracking system does not require a compliant person who can follow directions in order to collect meaningful data. To record meaningful data without verbal mediation, the systems, devices, and methods rely on reflexive or exogenous cueing of visual attention (whether for calibration, validation of calibration, or display of other visual stimuli) and may use naturalistic stimuli (e.g., video scenes of real-world social interaction) or quasi-naturalistic stimuli (e.g., video animations) to collect data and ultimately give a diagnosis. The naturalistic and quasi-naturalistic stimuli are effective because, even where a subject does not or cannot follow direction, the stimuli (e.g. videos) naturally gain the attention of the subject and meaningful data can be recorded. Therefore, the subject need not be aware that eye tracking data are being collected for that eye tracking data to be collected.

Figure 6:
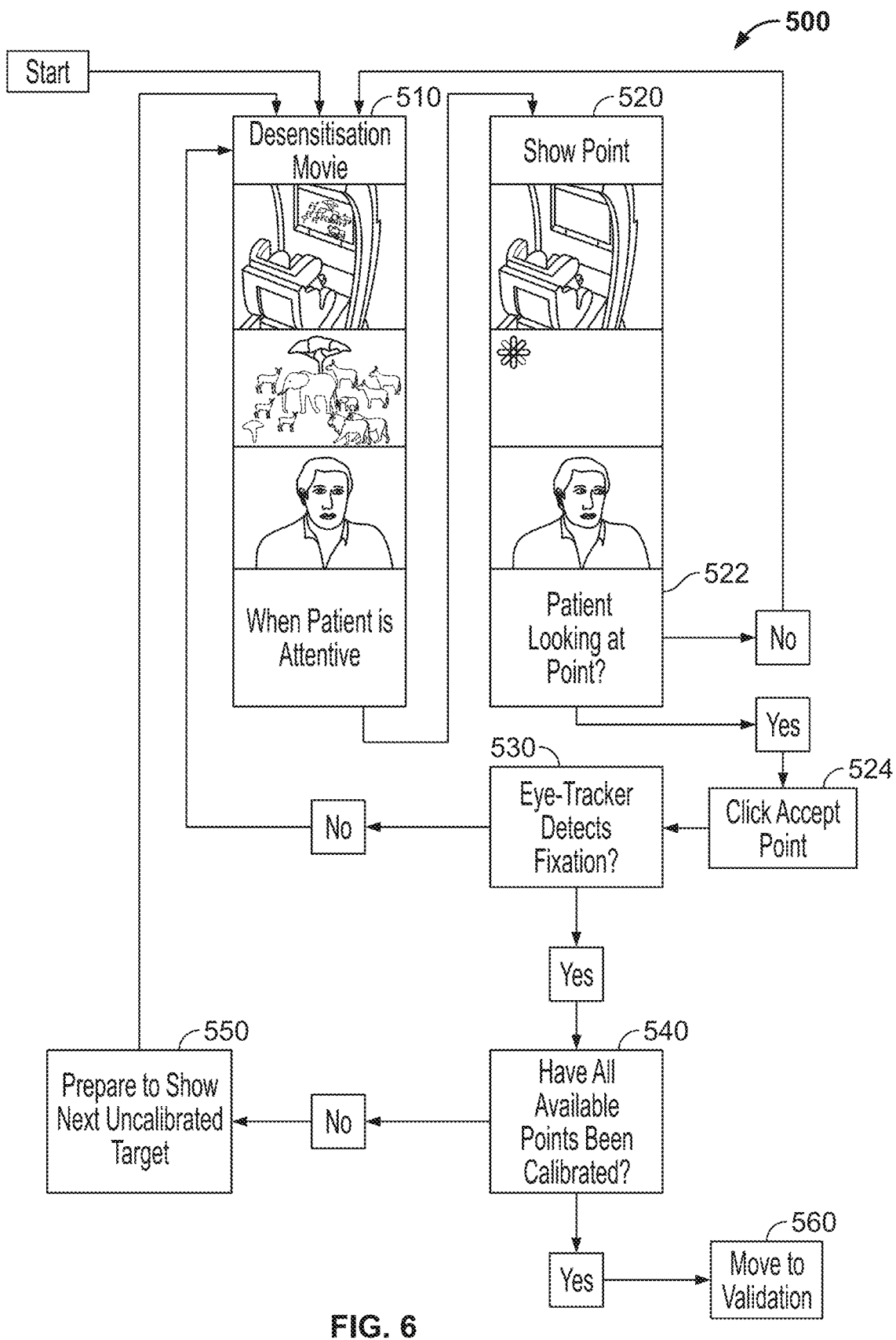
FIG. 6 shows an illustrative flowchart with computer-implemented functions for calibrating eye tracking data according to certain embodiments of the present disclosure.

There are several ways that calibration can be performed according to embodiments of the present disclosure. FIG. 6 shows a flowchart with computer-implemented functions for calibrating the eye tracking data according to certain embodiments. Proper calibration can be obtained from subjects who are unable to follow verbal instruction (e.g., because of age or cognitive level of functioning). The process 500 allows for the operator to have the discretion to decide when to show stimuli to attract the attention of subjects. The eye tracking systems, devices, and methods of the present disclosure are therefore effective with these populations because, based on such operator discretion, calibration need not be obtained only if the subject follows a set of target stimuli that appear with pre-specified duration and timing (though in some embodiments, calibration may be obtained in this way). In some embodiments, the calibration steps of process 500 may be performed as part of step 310 of FIG. 4.

Upon starting the calibration process 500, and in some embodiments, a desensitization movie is displayed for the subject at step 510. Data are generally not recorded during the display of the desensitization movie; instead, the movie is displayed to gain the attention of the subject. The movie may reflexively cause exogenous cueing by the subject without the need for verbal mediation or instruction by the operator. For example, the operator need not give instructions to look at the display device (e.g., display device 103 of FIG. 2) because the movie itself captures the subject's attention. When the subject is attentive, a calibration or fixation target is displayed at step 520. The calibration or fixation target reflexively captures the subject's attention and results in a saccade towards, and fixation upon, a known target location. The target reliably elicits fixations to a finite location; for example, a radially symmetric target spanning less than 0.5 degrees of visual angle. Other examples include concentric patterns, shapes, or shrinking stimuli that, even if initially larger in size, reliably elicit fixations to fixed target locations.

In some embodiments, when the subject is observed by the operator as looking at the target (step 522), the operator manually indicates (step 524) the observed fixation using an input device (e.g., by pressing an "accept point" button). If the subject is not looking at the target, the operator may continue displaying the target or cause the display of another desensitization movie. In certain embodiments rather than, or in addition to, the operator manually accepting that a subject is looking at a calibration target, the device (e.g., device 100) includes software or other logic capable of automatically determining that a subject is looking at the target (e.g., identifying a gaze within a predetermined spatial region around the target). At step 530, the eye tracker (e.g., eye tracking device 104 of FIG. 2) determines whether a fixation is detected. If no fixation is detected, the operator may allow for the continued display of the target and try to accept the target again, or the process 500 can be directed to return to step 510 and a desensitization movie is again displayed for the subject. If a fixation is detected, at step 540, it is determined whether all points have been calibrated. Any suitable number of points may be used in the calibration steps of the present disclosure. Preferably, at least two points are calibrated, though additional points (e.g., five) or fewer points (e.g., including no points) may be used. If all points have not been calibrated, the process prepares to show the next uncalibrated target at step 550 by first showing a desensitization movie at step 510. If all points have been calibrated at step 540, the process continues to step 560 where the calibrated points are validated.

Figure 7:
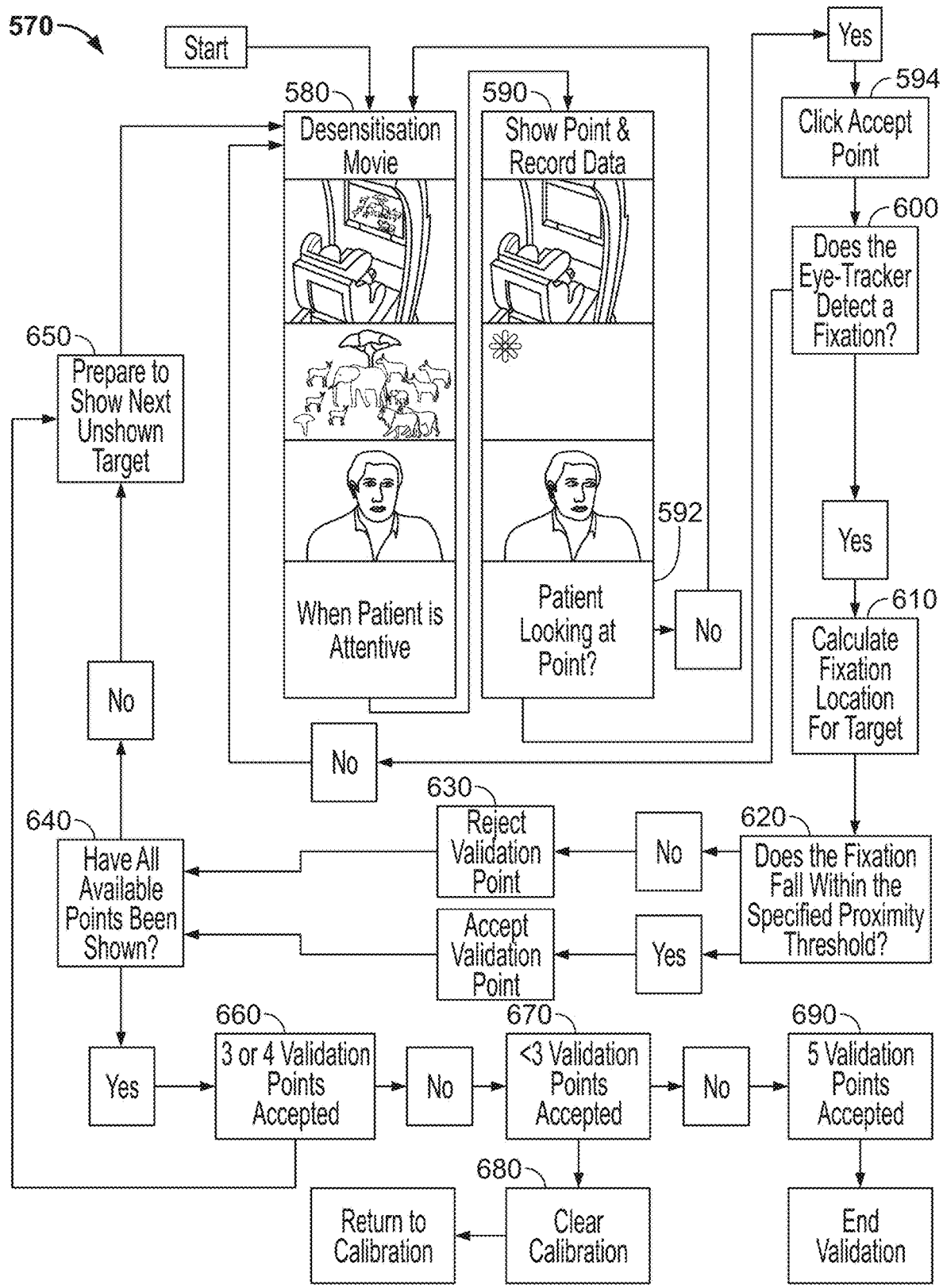
FIG. 7 shows an illustrative flowchart with computer-implemented functions for validating eye tracking data according to certain embodiments of the present disclosure.

FIG. 7 shows a flowchart with computer-implemented functions for validating the eye tracking data according to certain embodiments. Similar to the process 500 outlined in FIG. 6, the operator may have discretion to decide when to show stimuli to attract the attention of subjects. When the operator informs the software that a subject is looking at a target, recorded gaze coordinate information from that time is calculated and compared to the actual location of the displayed target. Initial validations with varying levels of success (e.g., number of points validated) will automatically instruct the operator to (1) recalibrate the eye tracker, (2) revalidate those targets which could not be validated, or (3) accept the calibration and continue to the "show stimulus and record gaze coordinate stream" state of the data collection software (e.g., step 316 of FIG. 4). Similar to calibration, it should be noted that the present systems, devices, and methods allow the operator to have discretion in the timing of showing target points and desensitization stimuli (e.g., movies). In some embodiments, the validation steps of process 570 may be performed as part of step 314 of FIG. 4.

The validation process 570 may begin after step 560 of the calibration process 500. In some embodiments, however, the validation process 570 may be performed (one or more times) after stimuli (e.g., movies) have been displayed to the subject in order to assess data accuracy during the course of data collection. At step 580 a desensitization movie is displayed to the subject. Data are generally not recorded during the display of the desensitization movie; instead, the movie is displayed to gain the attention of the subject. The movie may reflexively cause exogenous cueing by the subject without the need for verbal mediation or instruction by the operator. For example, the operator need not give instructions to look at the display device (e.g., display device 103 of FIG. 2) because the movie itself captures the subject's attention. When the subject is attentive, a calibration or fixation target is displayed at step 590 and data related to the subject's gaze position coordinates is recorded. The calibration or fixation target reflexively captures the subject's attention and results in a saccade towards, and fixation upon, a known target location. The target reliably elicits fixations to a finite location; for example, a radially symmetric target spanning less than 0.5 degrees of visual angle. Other examples include concentric patterns, shapes, or shrinking stimuli that, even if initially larger in size, reliably elicit fixations to fixed target locations.

In some embodiments, when the subject is observed by the operator as looking at the target (step 592), the operator manually indicates (step 594) the observed fixation using an input device (e.g., by pressing an "accept point" button). If the subject is not looking at the target, the operator may continue displaying the target or cause the display of another desensitization movie. In certain embodiments rather than, or in addition to, the operator manually accepting that a subject is looking at a calibration target, the device (e.g., device 100) includes software or other logic capable of automatically determining that a subject is looking at the target (e.g., identifying a gaze within a predetermined spatial region around the target). At step 600, the eye tracker (e.g., eye tracking device 104 of FIG. 2) determines whether a fixation is detected. If no fixation is detected, the operator may allow for the continued display of the target and try to accept the target again, or the process 570 can be directed to return to step 580 and a desensitization movie is again displayed for the subject. If a fixation is detected, at step 610, a fixation location is calculated for the fixation and it is determined, at step 620, whether the fixation falls within a specified proximity threshold of a known location coordinate for the target. At step 630, if the fixation is not within the specified proximity threshold, the fixation is rejected as a validation point. Otherwise, at step 630, if the fixation is within the specified proximity threshold, the fixation is accepted as a validation point.

Following the acceptance or rejection of the fixation, at step 640, it is determined whether all available points (corresponding to the number of points calibrated) have been shown. If not all points have been shown, the process prepares to show the next target at step 650 by first showing a desensitization movie at step 580. If all points have been shown, the process continues at step 660 where it is determined whether three or four validation points were accepted. In the affirmative, the process repeats at step 650 to show additional points. If less than three validation points were accepted (step 670) the system clears the calibration at step 680 and returns to the calibration process (e.g., process 500 of FIG. 6). The remaining alternative indicates, at step 690, that all five validation points have been accepted. At this step the validation process 570 ends. The foregoing discussion assumes that five calibration points are being validated. In some embodiments, validation may be acceptable where only four of five, or in some cases three of five, calibration points are accepted. Moreover, it will be appreciated that any suitable number of calibration points may be used, including in some embodiments zero calibration points, and that the validation process 570 (in particular steps 660, 670, 690) may be updated accordingly.

Figure 8:
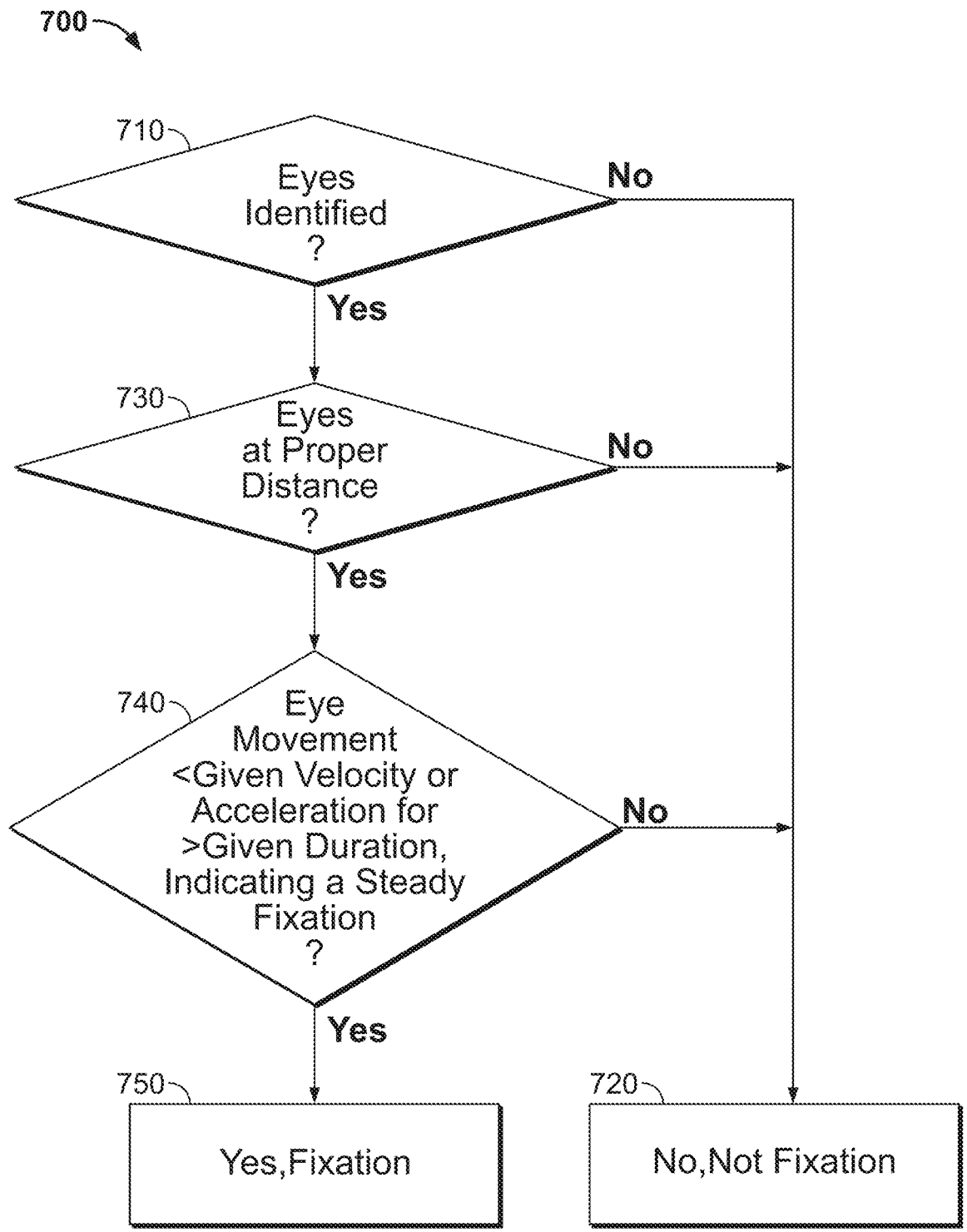
FIG. 8 shows an illustrative flowchart with computer-implemented functions for detecting whether a potential calibration point includes a fixation according to certain embodiments of the present disclosure.

In both the calibration and validation processes discussed above, there is included a step for determining whether the eye tracker detects a fixation (steps 530 and 600). FIG. 8 shows a flowchart with computer-implemented functions for detecting whether a potential calibration point includes a fixation according to certain embodiments. In some embodiments, the steps of process 700 may be performed as part of step 530 of FIG. 6 and/or step 600 of FIG. 7. After the operator indicates an observed fixation, the system may confirm or deny that indicated fixation using the steps of process 700. The eye tracking data collection software determines whether the gaze position coordinates in the data recorded at, or near, the time at which an observed fixation was indicated by the operator actually indicate a fixation on the target. In some cases, there may be a delay in the time the operator observes a fixation and the time a fixation actually occurs. The eye tracking data collection software and/or eye tracking device may thus consider a range of times at or near the time the operator indicated an observed fixation. For example, a window of two seconds may be analyzed relative to the observed fixation (one second prior to and one second after the time of the observed fixation). If there is no fixation during that window, the data point is determined not to include a fixation and may be rejected for calibration and/or validation purposes. If there is a fixation in that window, the data point is determined to include a fixation and may be accepted for calibration and/or validation purposes.

At step 710, the eye tracker determines whether the subject's eyes are identified. If the eyes are not identified, the data point is determined not to include a fixation at step 720 and may be rejected for calibration and/or validation purposes. If the eyes are identified, then at step 730 it is determined whether the eyes are a proper distance from the eye tracking device. Any suitable distance may be used for collecting data from the subject, and in some embodiments, the proper distance may depend on one or more attributes of the particular subject (e.g., age) or the eye tracker device itself. If the eyes are not at proper distance from the eye tracker, the data point is determined not to include a fixation at step 720 and may be rejected for calibration and/or validation purposes. If the eyes are at proper distance, then at step 740 it is determined whether the eye movement indicates a steady fixation. For example, even where the data includes a fixation, any of saccades, smooth pursuits, or blinks may also be present in the time window being analyzed. If there is such eye movement (e.g., saccades, smooth pursuits, blinks, etc.), the data may not be desirable for purposes of calibration or validation. Various techniques may be employed to detect a steady fixation at step 740. In some embodiments, an indication of fixation may occur when eye movement is less than a given velocity or acceleration for a given duration. For example, an indication of fixation may occur when eye movement is less than about five degrees/second for about 100 ms or more. It will be understood that any other suitable events may be defined to determine the occurrence of a steady fixation. If that event does not occur, the data point is determined not to include a fixation at step 720 and may be rejected for calibration and/or validation purposes. If that event does occur, then at step 750 the data point is determined to include a fixation and may be accepted for calibration and/or validation purposes.

In addition to the validation and error checking of calibration data that takes place during the data collection session, the validation and error checking of calibration data may occur after a given session is completed. The accuracy of eye tracking data is a feature that potentially limits the validity of subsequent analyses. Accuracy is dependent upon, among other things, the accuracy of the initial subject calibration (typically conducted at the start of a data collection session), on any head movements that may happen throughout the period of data collection, and on the natural and expected inter-subject variation in data quality and accuracy. If head movement is restrained, the accuracy of the initial calibration can be maintained; if head movement is not restrained, as is preferable, accuracy is likely to vary during the data collection session (e.g., skewed data points, or drift in the accuracy of initial calibration, may occur as a result of head movement during the data collection session). An algorithm for assessing and correcting spatial inaccuracy in collected eye tracking data is discussed below and with reference to FIGS. 9 and 10. This algorithm utilizes representative fixation points during recalibration instances within a testing procedure. Such representative fixation points may then be used in a post-hoc (i.e., after the testing procedure) transformation to correct skewed data points. In some embodiments, the transformation may occur in real-time as the data are collected. The figures show representative images of assessment and correction of calibration inaccuracies based on computer-implemented functions and criteria according to certain embodiments.

Accuracy of collected eye tracking data can be assessed, as discussed above, via the presentation of visual stimuli that reflexively capture attention and result in a saccade towards, and fixation upon, a known target location. The target reliably elicits fixations to a finite location; for example, a radially symmetric target spans less than 0.5 degrees of visual angle. Other examples include concentric patterns, shapes, or shrinking stimuli that, even if initially larger in size, reliably elicit fixations to fixed target locations. Such stimuli may be tested under data collection with head restraint to ensure that they reliably elicit fixations under ideal testing circumstances; then their use can be expanded to include non-head-restrained data collection.

In some embodiments, numerical assessment of the accuracy of collected eye tracking data may include the following steps: (1) presenting a fixation target that reliably elicits fixation to a small area of the visual display unit; (2) recording eye tracking data throughout target presentation; (3) identifying fixations in collected eye tracking data; (4) calculating a difference between fixation location coordinates and target location coordinates; (5) storing the calculated difference between fixation location coordinates and target location coordinates as vector data (direction and magnitude) for as few as one target or for as many targets as possible (typically five or nine but can be more); and (6) applying spatial transform to align fixation location coordinates with actual target location coordinates, by approaches including but not limited to (a) Trilinear interpolation, (b) linear interpolation in barycentric coordinates, (c) affine transformation, and (d) piecewise polynomial transformation.

Figure 9:
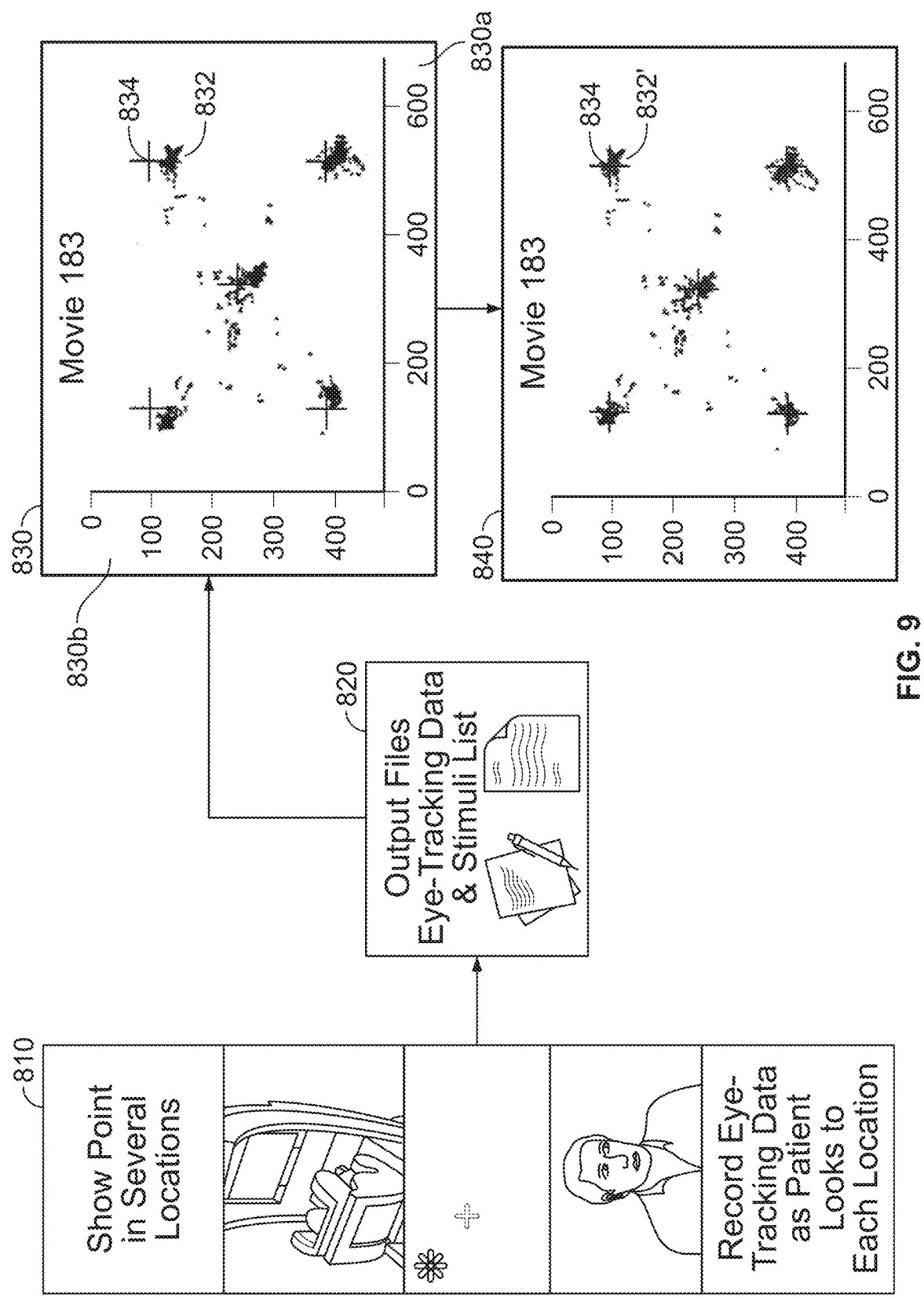
FIGS. 9 and 10 show representative images of assessment and correction of calibration inaccuracies based on computer-implemented functions and criteria according to certain embodiments of the present disclosure.
Figure 10:
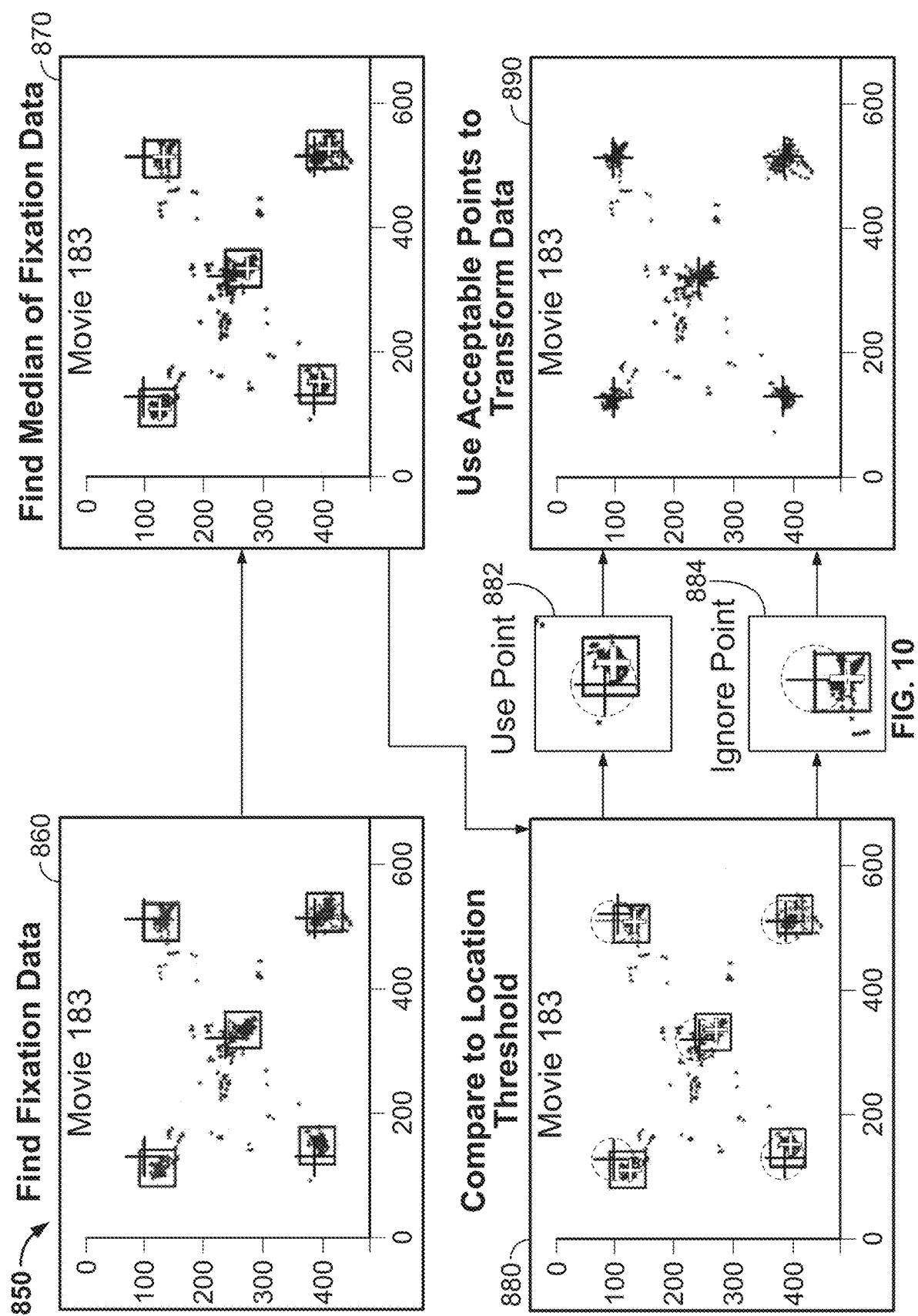

As shown in FIG. 9, recorded eye tracking data 810 is output to a file 820 (or multiple files) that contains eye tracking data and information relating to the stimuli (e.g., a list of movies viewed by the subject). The collected raw data are visually depicted in the figure as a display 830 with axes 830a, 830b that correspond to an image resolution (this resolution may be the actual resolution of the display screen or may be a reduced resolution to reduce processing times). As can be seen in the display 830, the raw data indicates that certain fixation location coordinates (e.g., points 832) are generally consistent with one another but are offset from their respective known target position coordinate (e.g., target 834). Display 840 shows the result of the spatial transform to align the fixation location coordinates 832' with the target location coordinate 834. Further details on the transform are shown in the progression of displays 850 in FIG. 10. The first display 860 shows the fixation data are extracted from the collected raw data. The second display 870 shows that a median of the fixation data is determined, and then in the third display 880, the median of fixation data is compared to a respective fixation location threshold. In some embodiments, points that are outside the threshold (points 884) are ignored. Alternatively, or additionally, such points may be weighted, in a probabilistic fashion, according to their proximity so as to calculate a weighted estimate of central tendency (e.g., median) without depending upon (or in addition to depending on) a fixed threshold. In some embodiments, points that are within the threshold (points 882) are used as acceptable points to transform the data to the result shown in display 890. It will be understood and appreciated that the accuracy of the detection of ASD as well as other developmental, cognitive, social, or mental conditions depends on the accuracy of the eye tracking data received from the eye tracking unit in the disclosed device.

Returning now to FIG. 1, in the embodiment shown, after data are collected by the data collection system 20, that data are transferred to the data storage system 30, which includes a secure database 35 with subject matching. The database is preferably remote from the device 100, to accommodate and aggregate collected data from many devices, but it will be appreciated that in some embodiments a database may be local to the device. Once the data collection is complete, the data are manually or automatically transferred (e.g., on a period basis, such as hourly or nightly) to an online database via a secure network connection. After the data are received at the online database, the data are analyzed. Generally, the analysis involves comparing the behavior of one particular subject to the behavior of other subjects who have seen similar movies while being eye tracked. In certain embodiments, however, the behavior of a particular subject is compared to that same subject's behavior earlier in time (e.g., compared to earlier sessions conducted in the preceding weeks, months, or years). According to certain embodiments, the results of the data processing and analysis indicate the likelihood that a subject has (or will develop) ASD symptomatology. In some embodiments, the results indicate a measure of the degree of typicality of normative development, providing an indication of variability in typical development.

Results of the analysis are generally delivered to each subject's physician or other caregiver via a secure, web-based portal. In some embodiments, there may be an operator portal and a physician portal. For example, a custom interface of the operator portal is provided for operators to access the database via one or more electronic devices. In some embodiments, the one or more electronic devices do not have reciprocal network access (i.e., data can only be pushed out to the devices, not received from the devices). In some embodiments, via this portal, users can (a) enter intake information for new subjects, (b) access user manuals and quick reference cards, and (c) access information about a past subject's experience with the device (e.g., notes about previous sessions, etc.). The physician portal enables physicians to access the results of a subject's test, once the raw data has been processed. The portal is usually accessible from an internet-enabled device.

Figure 11:
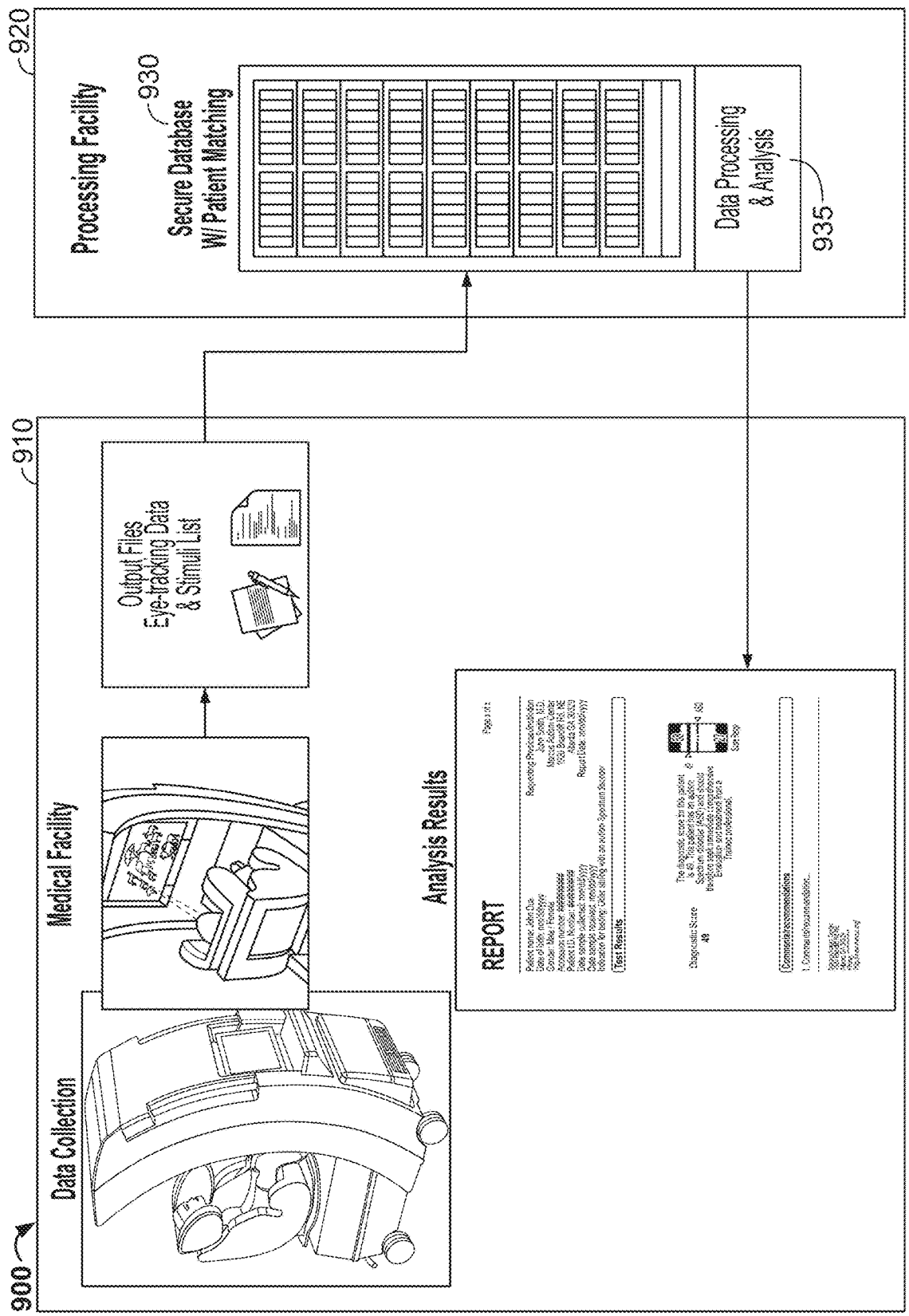
FIG. 11 shows a block diagram of an illustrative system for transferring collected data according to certain embodiments of the present disclosure.

FIG. 11 shows a block diagram of a system 900 for transferring collected data (e.g., from the data collection system 20 of FIG. 1) according to certain embodiments of the present disclosure. The arrangement of system 900 may be embodied as the data storage system 30 and data processing and analysis system 40 of FIG. 1. According to certain embodiments, the database 930 at the processing facility 920 provides centralized data storage and interfaces with other components such as a data collection system 20, and the data processing and analysis system 40, and generally provides subject specific information both to device operators and to physicians and/or specialists using the device. The data storage system 30 may be remote from the data processing and analysis system 40 or the two systems may be part of the same computing system. For example, as shown in FIG. 9, the processing facility 920 includes both data storage 930 and data processing and analysis 935 systems.

In some embodiments, the database is a SQL server, and is paired with tools written in any suitable programming language (e.g., Python, Matlab), allowing for URL based interface and query to the database. Additionally, the database may be compatible with programming languages (e.g., Python, Matlab) used for transferring data from the data collection system to the database, and from the database to the central processing computer. For example, where the device (e.g., device 100 of FIG. 1) is located at a medical facility 910, data collection occurs at that facility 910 and the data are transferred between the database 930 of the processing facility 920 and the medical facility 910. Generally, the database is secure, HIPAA-compliant, and protected by a redundant backup system.

Figure 12:
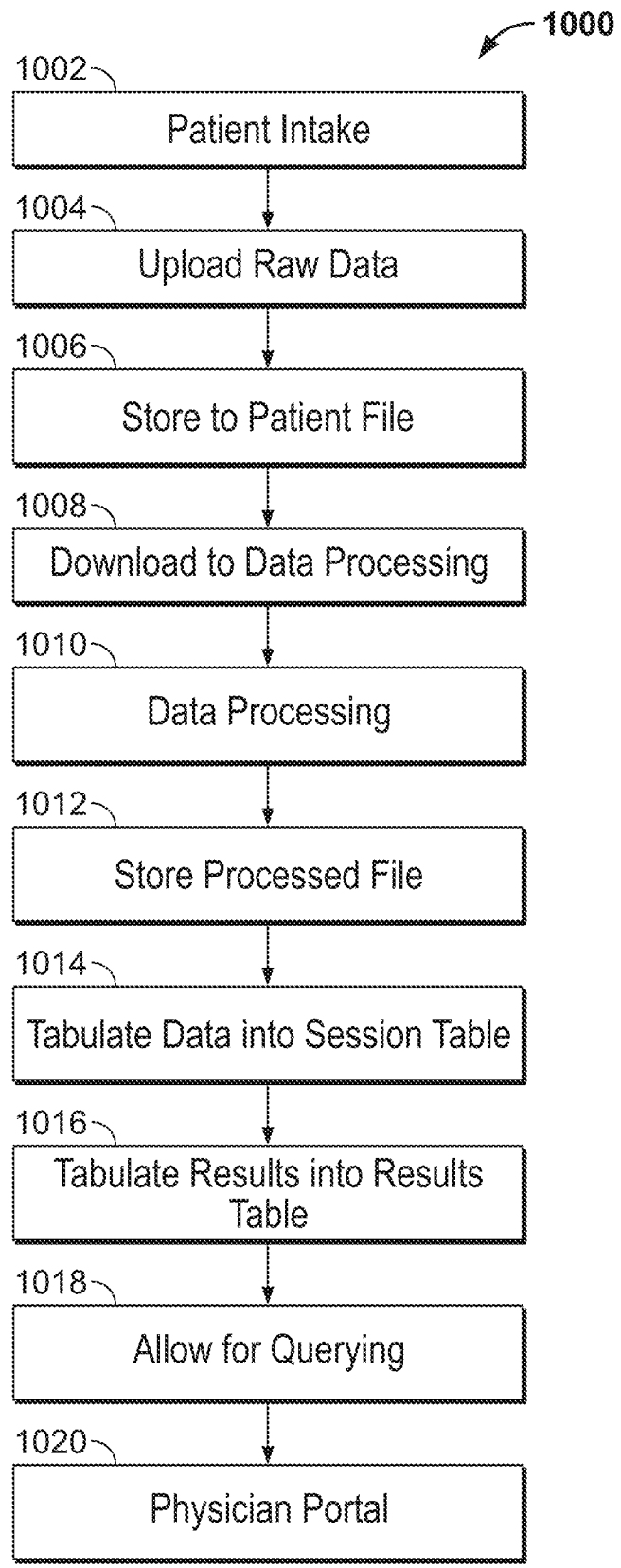
FIG. 12 shows an illustrative flowchart for supporting certain data collection and data processing and analysis steps using a centralized database according to certain embodiments of the present disclosure.
Figure 13:
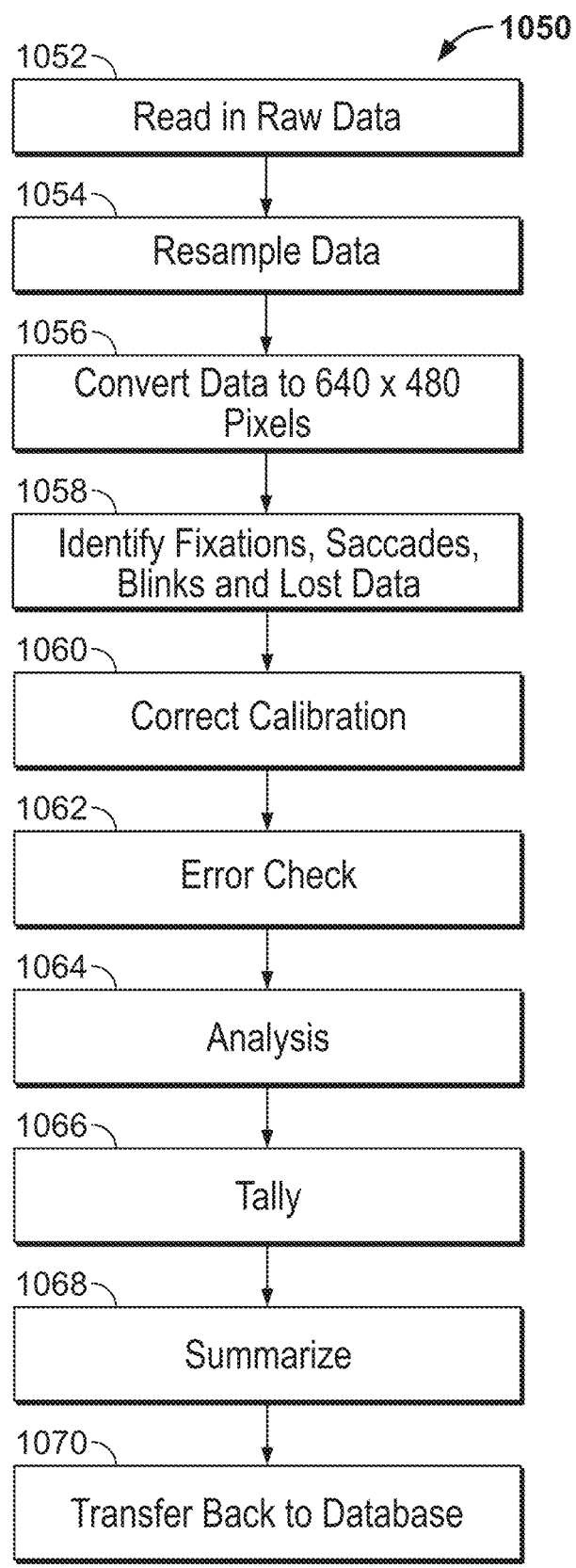
FIG. 13 shows an illustrative flowchart for processing collected data according to certain embodiments of the present disclosure.

In certain embodiments, the database is designed to enable (a) intake of new subject information, (b) storage of raw data files (e.g., including eye tracking data), (c) automated and secure transfer of files between a data collection device, data processing computer, and database, (d) tabulation and querying of data for the purposes of assessing device utilization and other data quality metrics, and e) access to results of processing by physicians. Exemplary functions of the database are depicted in FIG. 12 as a flowchart 1000 for supporting the data collection of data processing and analysis steps using a centralized database according to certain embodiments. Further functions of the database for data processing are depicted in FIG. 13 as a flowchart 1050 for processing the collected data according to certain embodiments. The flowcharts depict computer-implemented functions implemented in software code associated with a database that stores raw subject data, as well as files generated through data processing and analysis.

At step 1002, subject intake is performed. Prior to collecting data, the operator, or another trained user, may add the subject to the database (e.g., database 35 of FIG. 1) using an operator portal or any other suitable secure, web-based tool for entering and viewing intake information. At step 1004, the raw data are uploaded to the database. After a data collection session is completed using a device (e.g., device 100 of FIG. 1), two files are uploaded to the database, one containing raw eye tracking gaze position coordinates, and the other containing information relating to the stimuli (e.g., a list or playlist of those movies viewed by the subject). If a session attempt was unsuccessful, an empty playlist with the subject's identifiers may still be uploaded as a record.

At step 1006, the data are stored to the subject file. The uploaded data (and the identifiers within the playlist) are checked against the intake record, and (if matched) linked to the subject's record. If there is a mismatch, the data are stored in an error table for manual reconciliation. At step 1008, the data are downloaded to data processing. Regularly scheduled queries indicate raw data that has yet to be processed and push that raw data to a central processing computer. The data processing at step 1010 generally involves processing and then analyzing the raw data files, which yields diagnostic information about the subject. In certain embodiments, three files are generated, one containing processed ET data, one containing summary eye tracking statistics, and one containing diagnostic information. Further details of data processing are discussed below with respect to process 1050 of FIG. 13. At step 1012, the processed file is stored. The three files generated through processing at step 1010 are subsequently uploaded to the database and associated with the subject. At step 1014, the data are tabulated into a session table. Summary eye tracking information (e.g., fixation samples/movie, etc.) is read from the process summary ET file and tabulated in the database for subsequent query. Summary values (e.g., percentage fixation/movie, etc.) are then calculated within the database.

According to some embodiments, at step 1016 the results are tabulated into a results table. The summary diagnostic data are read from the diagnostic summary processed files and subsequently visualized within the database for physician review. At step 1018 the data may be queried. The database allows for URL-based querying (e.g., for those with administrative roles) to query across multiple variables. For example, variable may include subjects/devices, adverse events, etc. At step 1020, a physician portal (e.g., a web based interface) allows for physicians to view test results. A prewritten course of action may be provided based on the test results (e.g., seek further evaluation). It will be understood that the steps of the flowcharts of this disclosure are merely illustrative. Any of the steps of the flowcharts may be modified, omitted, or rearranged, two or more of the steps may be combined, or any additional steps may be added, without departing from the scope of the present disclosure.

As mentioned above, FIG. 13 shows a flowchart 1050 for processing the collected data according to certain embodiments. At step 1052, raw data are read into the database (e.g., database 35 of FIG. 1). For example, a software script written in any suitable programming language (e.g., Python, Matlab) may be used to transfer raw, unprocessed data files from the database to a computer for processing. This computer generally processes and analyzes the incoming data. Two files may be read into a program for analysis, one containing eye tracking data including (x,y) gaze position coordinates, the other containing information relating to the stimuli (e.g., a list of the movies viewed by the subject). Relevant information is separated out and binned. At step 1054 the data are resampled to account for any variance in time between samples. The data are resampled using any suitable interpolation technique. At step 1056 the data are converted to an appropriate resolution for analysis (e.g., 640×480 pixels). Raw data are typically collected at a higher resolution (e.g., 1024×768 pixels) than that used for processing (e.g., rescaled to 640×480 pixels). It will be understood that any suitable resolution may be used for data processing including any specified original resolution of the collected data.

At step 1058, unwanted fixations, saccades, blinks, and off-screen or failed data points are identified. Algorithms automatically identify times at which the subject was fixating (in an undesirable way), saccading, blinking, or times when the subject was not looking at the screen. In an exemplary embodiment, the data processing application is an automated executable written in a programming language such as Matlab, although any other suitable programming language may be used. Generally, the software extracts relevant information from the raw files generated during a subject's testing session, and uses that information to derive a diagnosis through statistical analysis. The program, in one aspect, automatically identifies basic oculomotor events (unwanted fixations, saccades, blinks, off-screen or missing data, etc.) and adjusts for aberrations in gaze position estimations as output by the eye tracking equipment. For example, at step 1060 the calibration is corrected. With data from times during which additional calibration targets were shown, any discrepancies in gaze position are corrected. Some larger discrepancies may exclude certain data from subsequent analysis. At step 1062 error checking is performed. Data from movies may be excluded from subsequent analysis if (a) the subject fixated on the screen for less than 20% (or any other suitable percentage) of the movie duration or (b) movies were not shown for their entire duration. At either or both of steps 1060 and 1062, the data assessment and correction discussed above with respect to FIGS. 9 and 10 may be used.

At step 1064 data analysis is performed. Individual subject data are compared to instances of significant difference in gaze position for subjects (e.g., infants and toddlers) across varying levels of social, cognitive, or developmental functioning. Analysis of the data may reveal the level of social functioning by comparison. Within this processing step, a statistical analysis of the subject's eye tracking data may be used to determine if that subject is diagnosed with a development or cognitive condition including ASD. As previously disclosed in U.S. Pat. No. 7,922,670, incorporated by reference above, processed eye tracking data are compared to existing data models to determine a level of a developmental, cognitive, social, or mental condition. The generated score is then compared to predetermined cutoff or other values to determine that subject's diagnosis of ASD, as well as a level of severity of the condition. In certain other embodiments, a subject's point-of-gaze data (i.e., visual fixation data) is analyzed over a predetermined time period (e.g., over multiple sessions spanning several months) to identify a decline or other salient change in visual fixation (e.g., point-of-gaze data that initially corresponds to that of typically-developing children changing to more erratic point-of-gaze data corresponding to that of children exhibiting ASD).

At step 1066 a tally is performed. Gaze position coordinates are compared to pre-specified regions of interest across each frame of the movie shown. At step 1068 relevant statistics are summarized. Summary statistics for each movie, including time of fixation on screen and each region-of-interest, as well as time spent saccading, blinking, or otherwise not engaging with the screen are recorded. The results of the social functioning analysis are also summarized. Finally, at step 1070, the processed data are transferred back to the database. In certain embodiments, two files are transferred back to the database, one containing summary statistics and one containing binned information with tracking of each step of processing and analysis. Similar to the raw data download script discussed above at step 1052, any suitable script may be used to transfer all of the processed data files back to the database. As discussed previously, diagnostic results of the processing can be accessed via the physician portal. It will be understood that the steps of the flowcharts of this disclosure are merely illustrative. Any of the steps of the flowcharts may be modified, omitted, or rearranged, two or more of the steps may be combined, or any additional steps may be added, without departing from the scope of the present disclosure.

Figure 14:
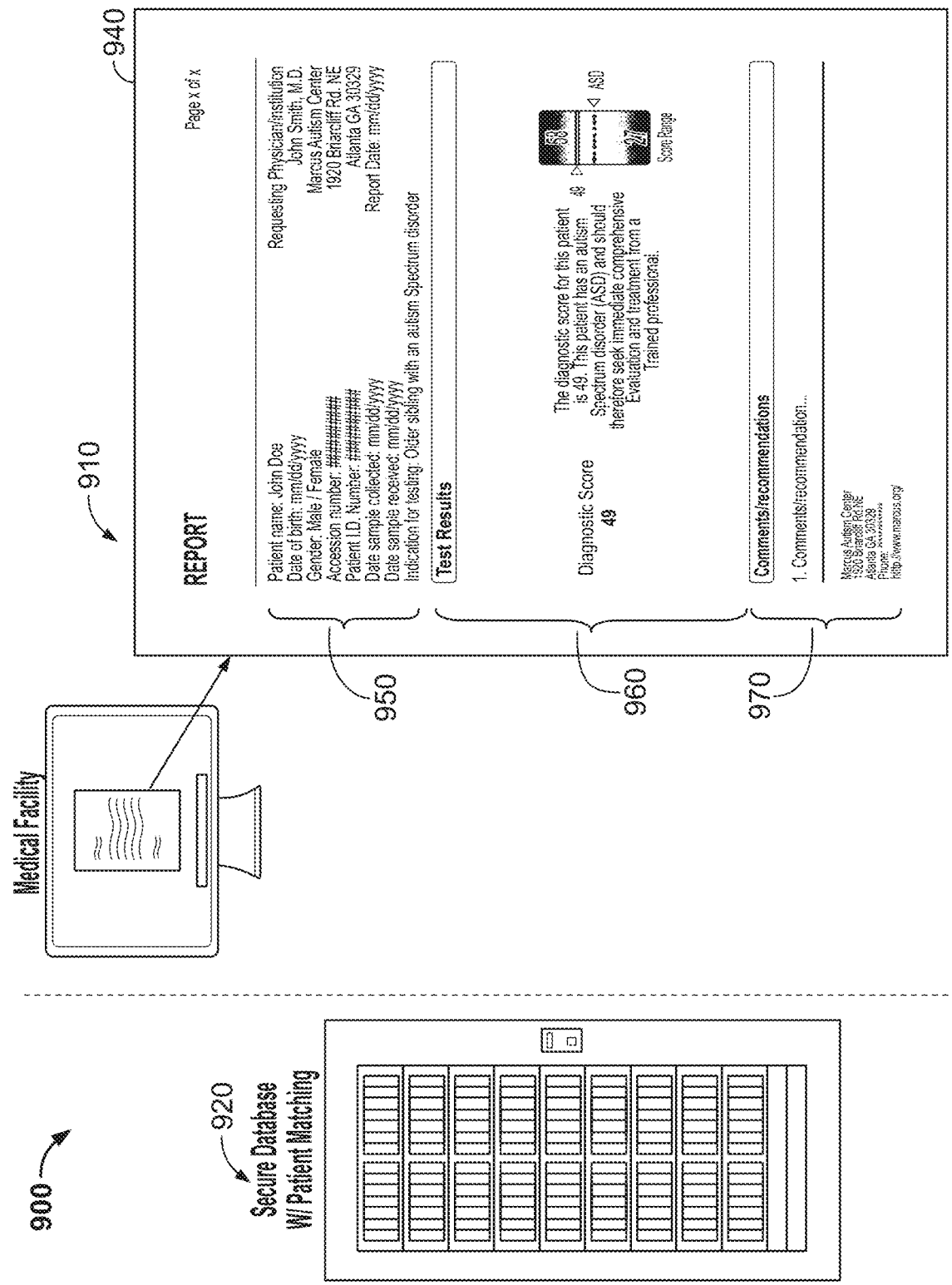
FIG. 14 shows a block diagram of an illustrative system for delivering results of data analysis according to certain embodiments of the present disclosure.

The diagnostic or prescriptive result, based on the data processing and analysis, can be presented to the physician or other caregiver in any suitable manner. For example, FIG. 14 shows a block diagram of the system 900 of FIG. 11 used for delivering results of the data processing and analysis according to certain embodiments. This arrangement of system 900 includes the medical facility 910 and the database 930 of processing facility 920. The processing facility 920, through the database 930, may deliver a diagnostic report/results sheet 940 as shown. The report 940 includes bibliographic and other relevant information 950 related to the data collection, the test results 960, depicted as a diagnostic score, and comments and recommendations 970. It will be understood that any suitable format may be used to provide the diagnostic or prescriptive result to the physician or other caregiver. In some embodiments, the device may be provided with a printer to deliver the test results directly.

Figure 15:
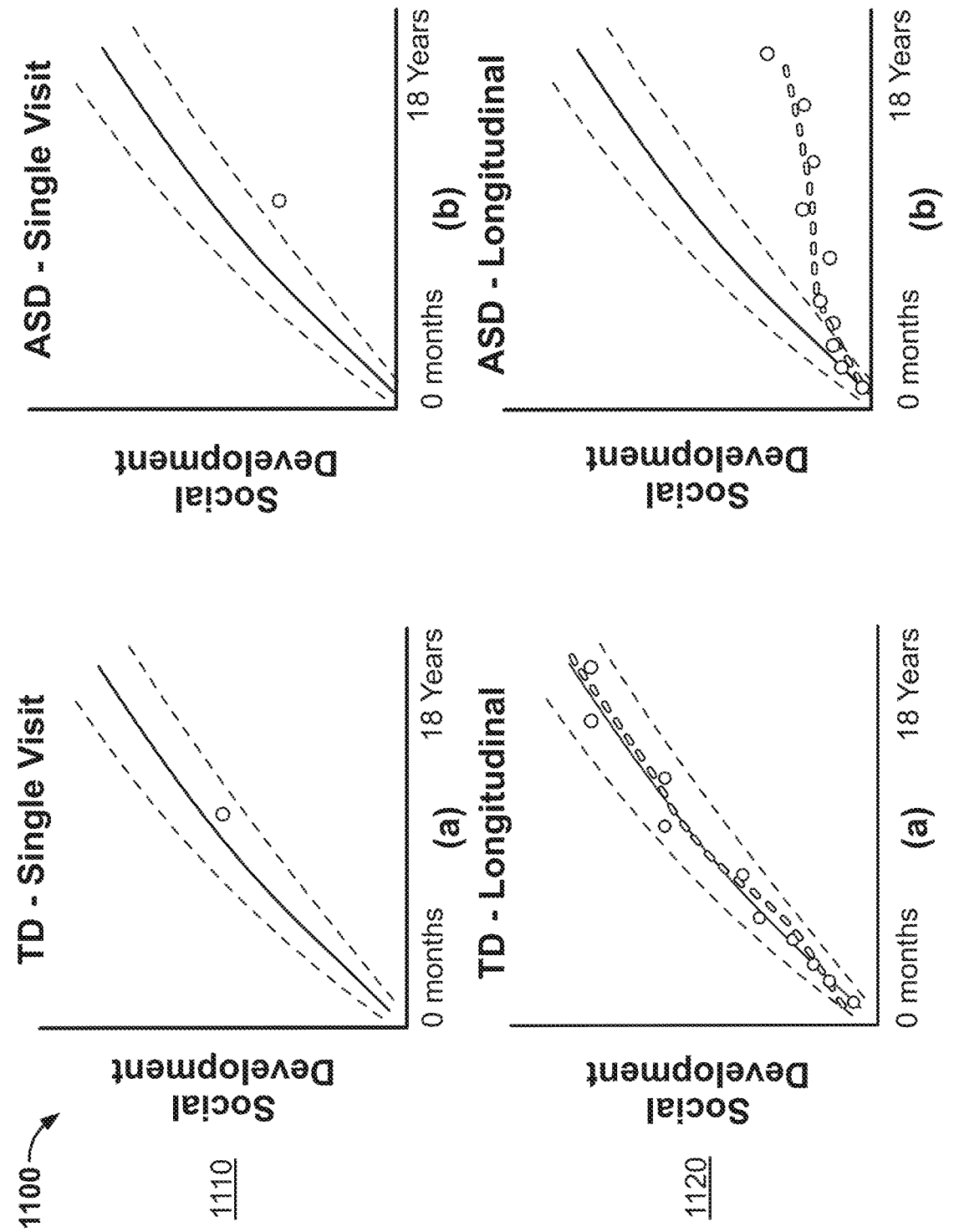
FIG. 15 shows illustrative computer-generated data representations of a subject's developmental or cognitive progression relative to other developmental or cognitive profiles according to certain embodiments of the present disclosure.

For example, referring now to FIG. 15, computer-generated data representations of a subject's developmental, cognitive, social or mental progression relative to other developmental, cognitive, social, or mental profiles are shown. The diagnostic growth charts 1100 indicate several illustrative subjects' social development as compared to historic norms for typically developed subjects and those known to have ASD. For example, charts 1110(*a*) and 1120(*a*) relate to subjects showing typical development relative to those with ASD based on a single data point 1110 or on multiple data points 1120 taken over time. Charts 1110(*b*) and 1120(*b*) relate to subjects showing various levels of ASD based on a single data point 1110 or on multiple data points 1120 taken over time.

The above disclosure relates generally to systems, devices, and methods for the detection of developmental, cognitive, social, or mental abilities or disabilities, including ASD, in subjects using analysis of eye tracking data generated in response to display of specific predetermined visual stimuli (e.g., one or more videos) to the subject. What follows next is a discussion of particular embodiments of the present disclosure in which the present systems, devices, and methods relate to assessing the risk of developmental abilities and disabilities in very young patients (e.g., in the first 2-6 months of life). For convenience, the discussion herein relates to assessing developmental disabilities, but it will be understood that the disclosure also applies for assessing normative/typical development and abilities in subjects. According to certain aspects, the decline in visual fixation of a subject over time with respect to certain dynamic stimuli provides a marker of a possible developmental condition (such as ASD) of the subject. The visual fixation of the subject is identified, monitored, and/or tracked over time (e.g., in the first 6 months of life) through repeated eye tracking sessions, and data relating to the visual fixation is then compared to relative norms to determine a possible increased risk of a developmental condition in the subject. A change in visual fixation (in particular, a decline in visual fixation by a subject with image of eyes, body, or other region-of-interest of a person or object displayed on a visual stimulus) as compared to similar visual fixation data of typically-developing subjects or to a subject's own, prior visual fixation data provides an indication of a developmental, cognitive, social, or mental ability or disability.

As indicated earlier above, although the majority of the present disclosure generally refers to assessing and/or diagnosing the risk of autism, the systems, methods, research, and information described herein can be used to assess the risk of a host of other developmental, cognitive, social, and mental disabilities in young patients, including attention deficit disorder (ADD), attention deficit hyperactivity disorder (ADHD), certain learning disabilities, and others. Accordingly, it will be understood and appreciated that the systems and methods described in the present disclosure are not limited to the specific autism detection techniques described herein, but may apply broadly to other disabilities as will occur to one of ordinary skill in the art. For ease of reference and discussion, however, the following disclosure describes embodiments, research, examples, experimental methodologies, information, and conclusions that relate specifically to a non-limiting example of autism.

Generally, deficits in eye contact have been a hallmark of autism since the condition's initial description; however, the early onset of these deficits has not been known. The present disclosure provides systems, methods, devices, and evidence indicating that infants later diagnosed with autism spectrum disorders exhibit mean decline in eye fixation (and, generally, visual fixation) within the first 2 to 6 months of life. This decline in visual fixation is generally correlated with severity of clinical outcome; and decline in the first year alone, before overt symptoms manifest, significantly predicts severity of future outcome. The timing of decline pinpoints a narrow developmental window of cortical maturation, and reveals the early derailment of processes that would otherwise play a key role in canalizing typical social development. This early divergence from normative experience suggests a means by which diverse genetic liabilities are instantiated, developmentally, into a spectrum of affectedness. Finally, the observation of this decline rather than outright absence offers a promising opportunity for early intervention, one that could build on the apparent preservation of mechanisms subserving reflexive initial orientation towards the eyes.

Again, according to aspects of the present disclosure, identifying and analyzing a decline in eye fixation (or visual fixation) for an individual over a predetermined time period (e.g., the first 2-6 months of life) provides a marker of ASD or another developmental, cognitive, social, or mental condition. What immediately follows next is a discussion of exemplary data collection and analysis methods associated with the present embodiment.

Figure 16A:
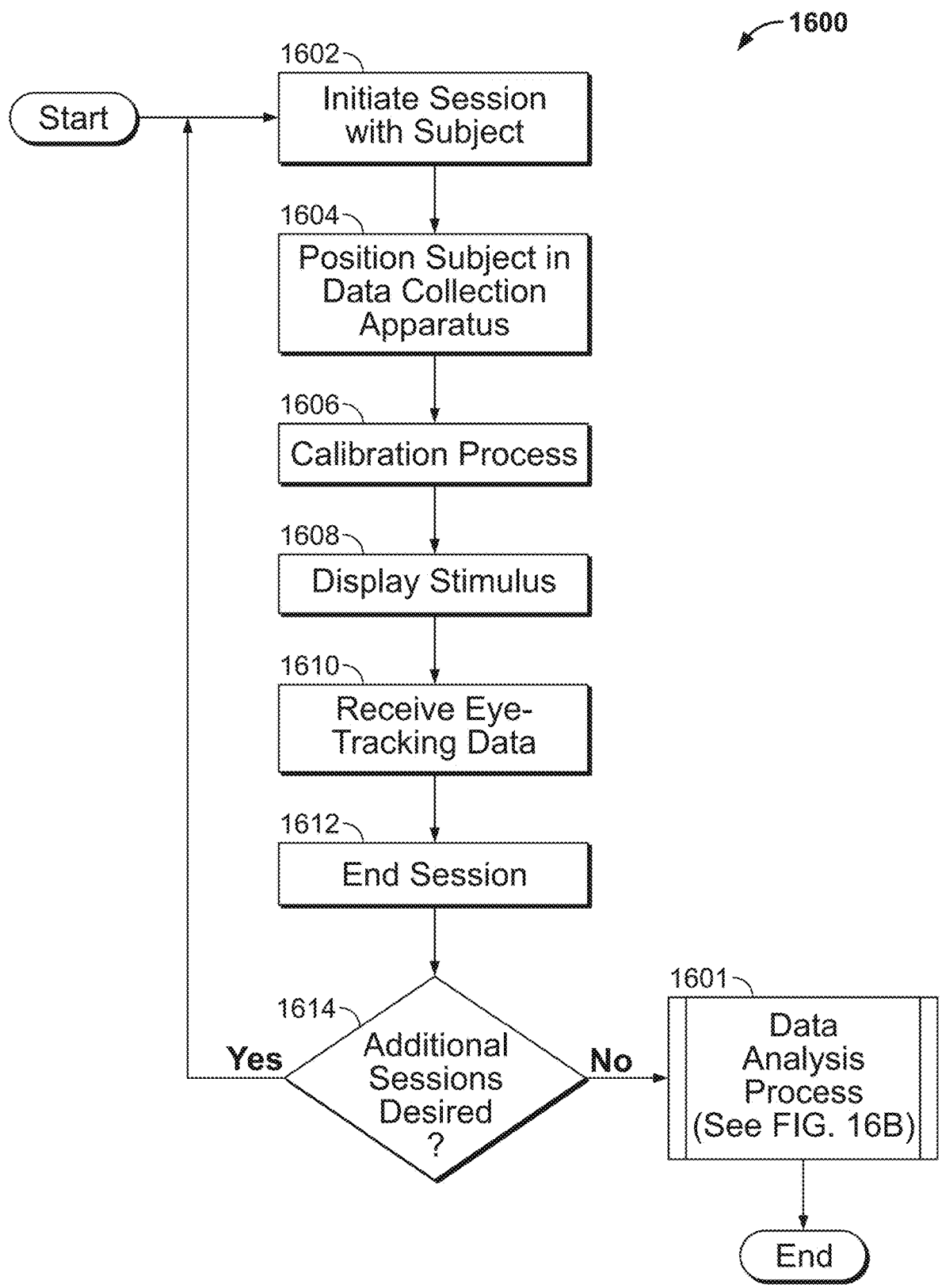
FIG. 16A shows an illustrative flowchart of an exemplary data collection process according to one embodiment of the present disclosure.

Referring again to the Figures, FIG. 16A is a flowchart illustrating an exemplary data collection process 1600 according to some embodiments of the present disclosure. Generally, aspects of the process 1600 correspond to collecting data for an individual or subject over two or more sessions spanning a predetermined time period (e.g., weeks, months, years, or longer). At the start of process 1600, a session is imitated with a given subject (step 1602). For purposes of the presently-described embodiment, the subject will generally be between 2 and 24 months of age, but as will be understood and appreciated, not limitation on the age of the subjects is intended by the present disclosure. To initiate a session, the subject is positioned in a data collection apparatus, such as the device 100 described in connection with FIGS. 1-3 above. Generally, the subject is positioned within the device to avoid unwanted movement and to enable clear viewing of a visual display (e.g., display device 103). Infants and young toddlers are generally positioned in a seat that accommodates their preferred body position (e.g., laying or being cradled, such as that shown in FIGS. 3A, 3B, and 3D-3F, described above), whereas toddlers, older children, and adults are generally positioned in a seat that reflects a preferred upright positioning (e.g., such as that shown in FIGS. 2 and 3C).

After the subject has been positioned in the data collection device, the device may be calibrated to the specific subject (e.g., positioning, eye positioning, height, weight, etc.) (step 1606). Details of a calibration process have been discussed earlier in this disclosure (see FIGS. 4 and 5 and related disclosure). After calibration, a first stimulus is displayed to the subject (step 1608). As mentioned previously, this stimulus may be a dynamic visual stimulus (or other type of stimulus) designed to elicit eye-looking. During the display of the stimulus, the device receives and captures eye-tracking data (also referred to as point-of-gaze data) (e.g., from an eye-tracking device or sensor 104). Generally, the eye-tracking data will include frame-by-frame eye-looking positions (e.g., coordinates or point-of-gaze data) that can be later mapped to regions-of-interest in the stimulus.

At step 1614, the system queries whether or not additional sessions with the respective subject are desired. In some embodiments, step 1614 is initiated only after a predetermined amount of time (e.g., one week, two weeks, one month, several months, etc.). Generally, sessions are separated by predetermined periods of time so that change in visual fixation for the subject can be tracked over time. Thus, at step 1614, if it is determined that another session is desired, the process 1600 loops back to initial step 1602, and another session is initiated with the subject (i.e., steps 1602-1614 are repeated). If no additional sessions are desired (i.e., sufficient data over time has been collected for the given subject), then the process proceeds to a data analysis process 1601.

Figure 16B:
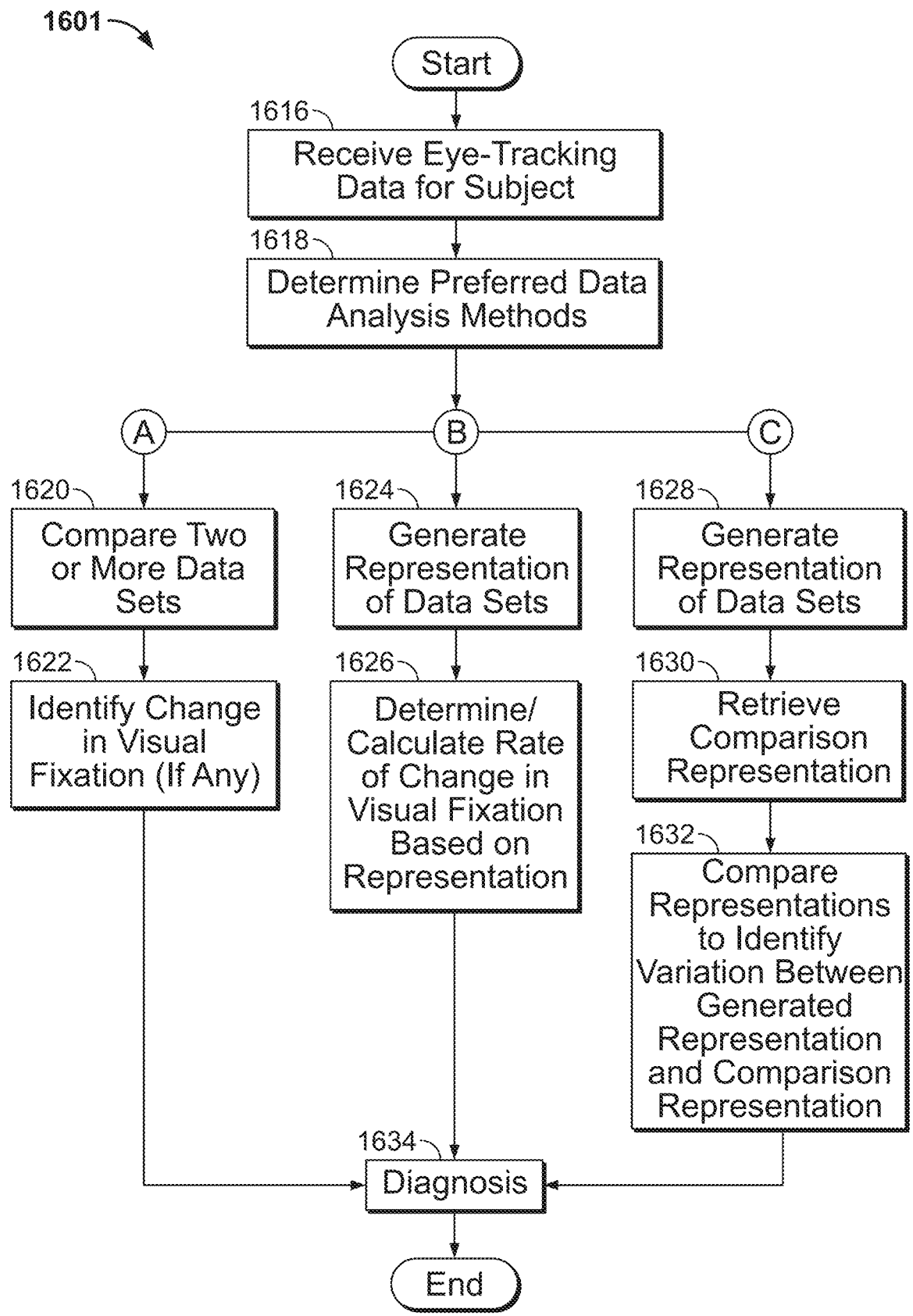
FIG. 16B shows an illustrative flowchart of an exemplary data analysis process, according to one embodiment of the present disclosure.

FIG. 16B is a flowchart illustrating an exemplary data analysis process 1601, according to some embodiments of the present disclosure. As shown, the process 1601 includes several exemplary methodologies for analyzing eye-tracking data to determine the visual fixation for a subject and identify or track the change or rate-of-change (e.g., decline) in visual fixation for the subject over time. At step 1616, the system receives eye-tracking data for a given subject. This data may be collected through a process such as the exemplary process 1600 shown in FIG. 16A, or another similar data collection process.

Once the data is received, there are different ways in which the data can be analyzed to determine a change in visual fixation (and, ultimately, arrive at a potential diagnosis for the subject). According to some embodiments (path A), data sets of eye-tracking data for the given subject are compared to each other (step 1620) to identify a change in visual fixation for the subject (if any) (step 1622). In this embodiment, at least two data sets are required (corresponding to at least two different sessions over a given time period). For example, as shown in more detail below, certain declines in visual fixation, which can be represented by changes in slope or downward trends in data points, may indicate a potential for the individual to develop ASD (or some other condition). According to another embodiment (path B), the data sets can be visualized as a graphical representation or plot (step 1624), and a rate-of-change or slope in the representation can be measured and/or calculated. In yet another embodiment (path C), a representation of the given subject's data (step 1628) can be compared to a retrieved comparison representation of data for a similar stimulus or control group (step 1630). The comparison representation (e.g., graph, data plot, table, etc.) may relate to a control group, a similar test group, prior data of the subject himself/herself, etc.). These representations are then compared to each other to identify a variation between the two (e.g., whether or not the subject's representation falls within some predetermined threshold of the comparison representation).

At the end of any of the embodiments represented by paths A, B, or C, a diagnosis of the subject may be performed (step 1634). For example, if the data for the subject strongly indicates a decline in eye fixation in the first 6 months of life, such that the decline is beyond some acceptable limit or clearly has a downwardly-trending slope, then such decline may be a marker for ASD or some other developmental, cognitive, social, or mental condition. The graphs and experimental data shown and described in more detail below provide additional details relating to this concept.

It will be understood that the steps of the flowcharts of this disclosure are merely illustrative. Any of the steps of the flowcharts may be modified, omitted, or rearranged, two or more of the steps may be combined, or any additional steps may be added, without departing from the scope of the present disclosure.

Experimental Overview

The following exemplary discussion relates to particular experiment(s) to test the extent to which measures of early-emerging normative processes (e.g., preferential attention to familiar voices, faces, face-like stimuli, etc.) may reveal disruptions in ASD at a point prior to the manifestation of overt symptoms. Generally, the experiments included using eye tracking data for infants and young toddlers over the course of multiple sessions (spanning several months) to identify changes (and, in particular, a decline) in visual fixation (i.e., point-of-gaze data) for the infants and toddlers with respect to visual stimuli that were presented to the infants and toddlers. Details of the experiment(s) conducted, along with associated data/parameters, exemplary settings, the associated results from the experiment(s), general implications, and alternate embodiments, will be better understood in the description and accompanying figures provided in greater detail below.

In general, the tests measured preferential attention to the eyes of others, a skill present in typical infants, but significantly impaired in 2-year-olds with ASD. Data were collected at 10 time points: at months 2, 3, 4, 5, 6, 9, 12, 15, 18, and 24. The experiments focused on 110 infants, enrolled as risk-based cohorts: N=59 at high-risk for ASD (full siblings of a child with ASD) and N=51 at low-risk (without $1^{st}$, $2^{nd}$ or $3^{rd}$ degree relatives with ASD). Diagnostic status was ascertained at 36 months for each individual tested. Further details relating to the study design, clinical characterization of participants, and experimental procedures are provided below in the Experimental Methods and Supplemental Experiment Information Sections of this disclosure.

Of the high-risk infants, N=12 met criteria for ASD (10 males, 2 females), indicating a conversion rate of 20.3%. One child from the low-risk cohort was also diagnosed with ASD. Given the small number of girls in the ASD group, the analyzed test subjects were constrained to males only, N=11 ASD (10 from the high-risk cohort and 1 from the low-risk), and N=25 typically-developing (TD) (all from the low-risk cohort).

Figure 17C:
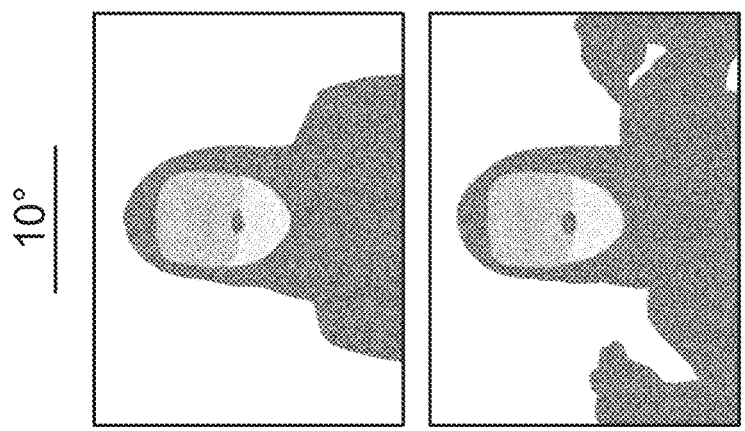
FIG. 17C shows exemplary regions-of-interest corresponding to the exemplary screens of FIGS. 17A and 17B, according to one embodiment of the present disclosure.
Figure 17B:
FIGS. 17A and 17B show illustrative screenshots of exemplary stimuli frames showing a representative caregiver, according to one embodiment of the present disclosure.
Figure 17A:
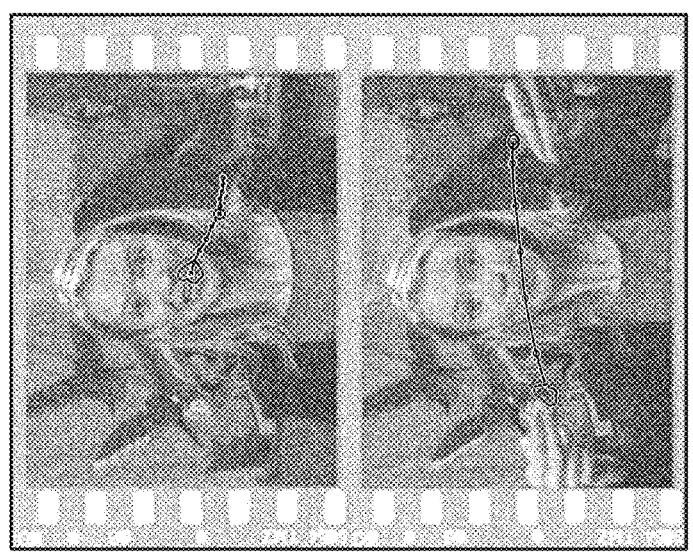

At each testing session, infants viewed scenes of naturalistic caregiver interaction while their visual scanning was measured with eye-tracking equipment. FIGS. 17A and 17B are illustrative screenshots of stimuli (e.g., video) frames showing a representative caregiver. Representative data (two seconds of eye tracking data) from a 6-month-old that was later diagnosed with ASD are overlaid (as data dots/points) on the screens 1702 of FIG. 17A. Representative data (2 seconds of eye tracking data) from a typically-developing 6-month-old are overlaid (as data dots/points) on the screens 1704 of FIG. 17B. In FIGS. 17A and 17B, saccades are plotted as thin lines with dots, whereas fixation data are plotted as larger dots. The N=36 TD and ASD children viewed 2,384 trials of video scenes.

Figure 28A:
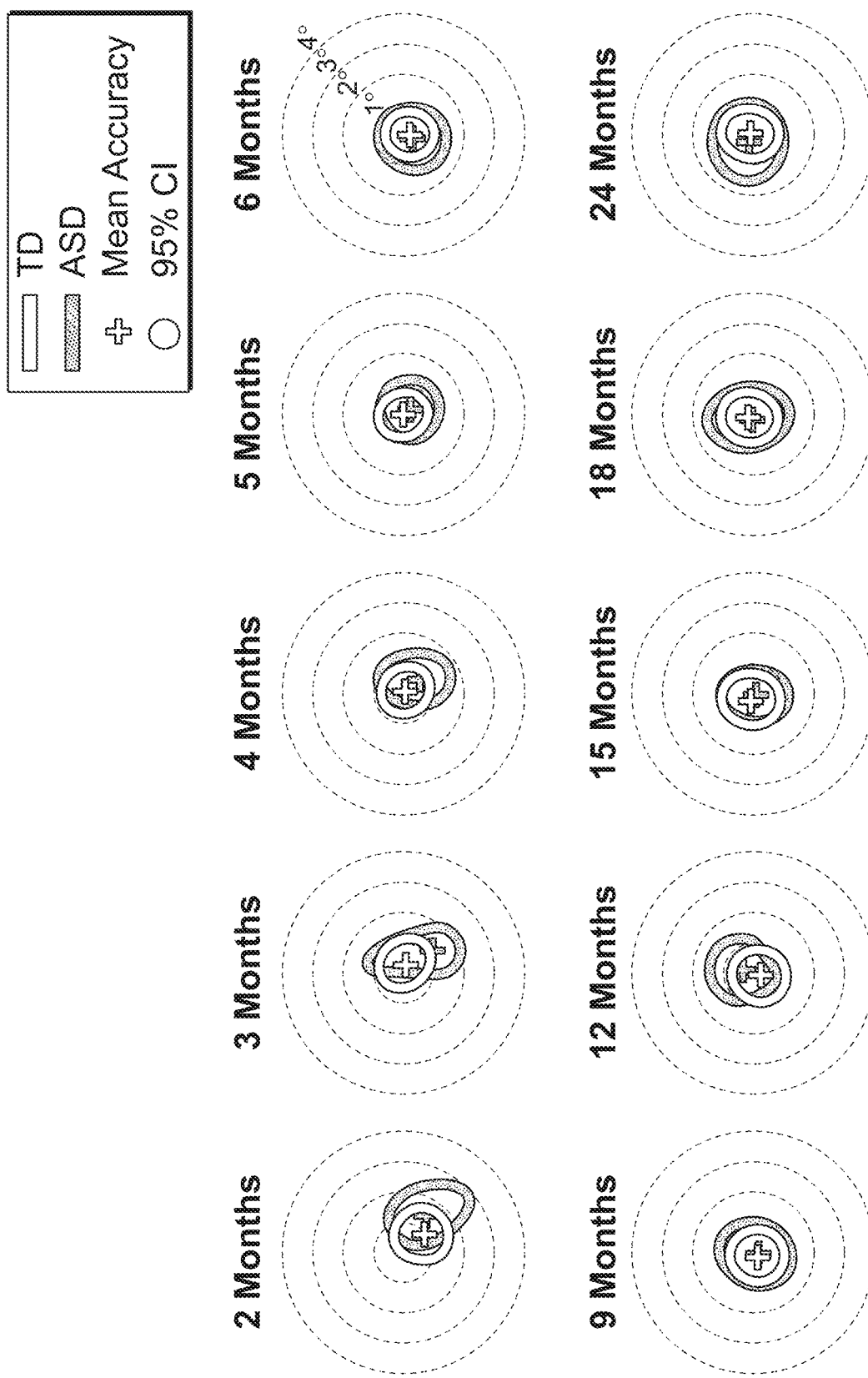
FIG. 28A shows a graphical illustration of calibration accuracy, based on an annulus showing the 95% confidence interval for calibration for one experimental test group, according to one embodiment of the present disclosure.
Figure 29A:
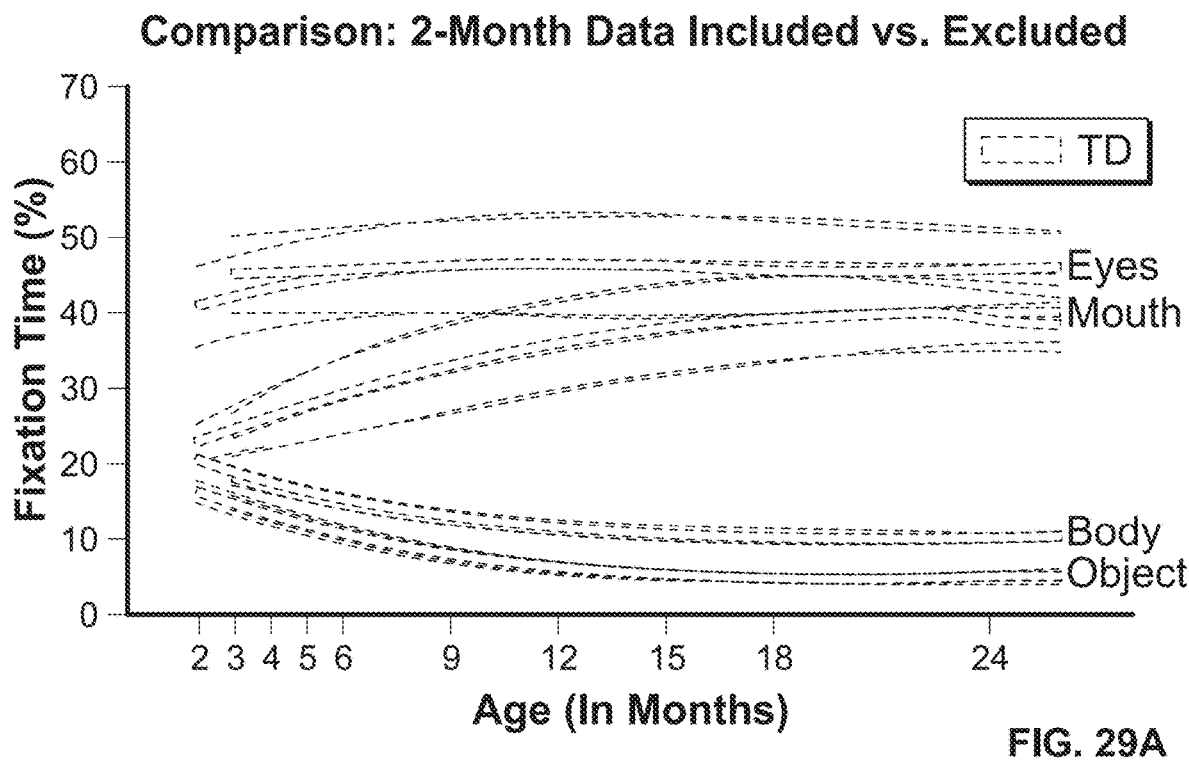
FIGS. 29A and 29B show growth charts of visual engagement and their relationship to dimensional and categorical outcome, with data from month 2 included versus excluded, for typically-developing children and those with ASD, respectively, for one experimental test group, according to one embodiment of the present disclosure.
Figure 29B:
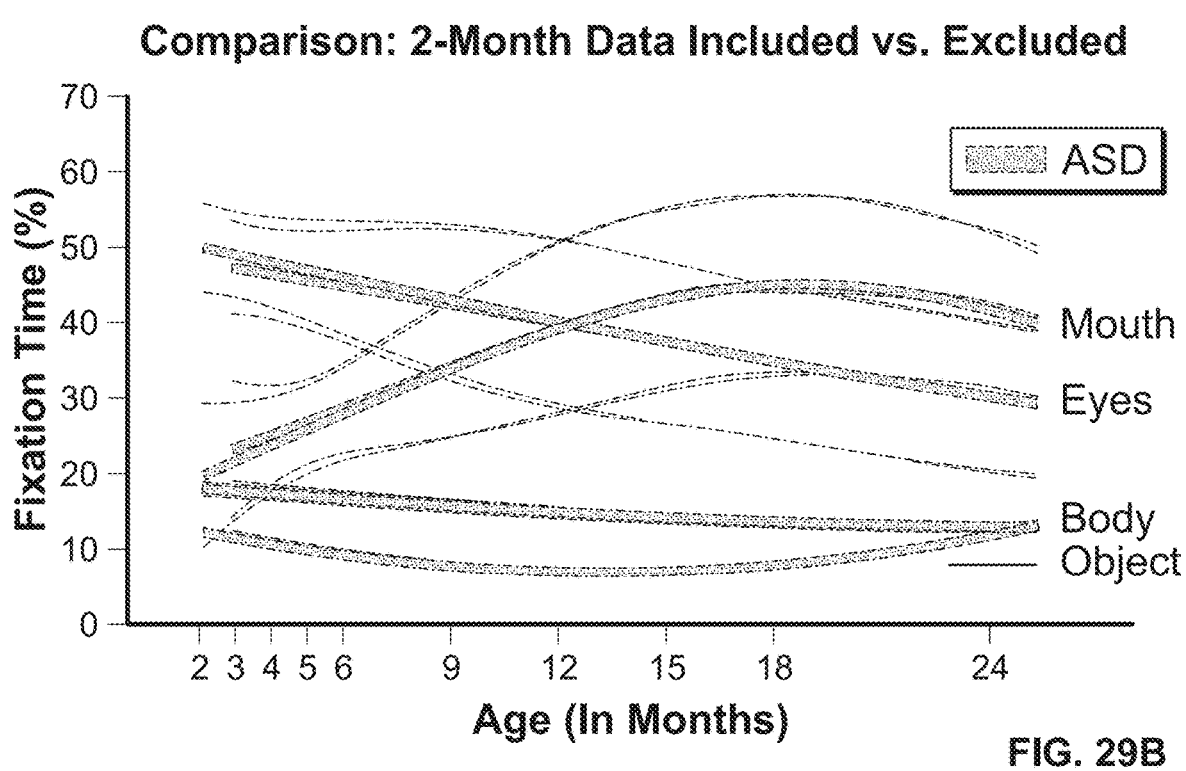
Figure 29C:
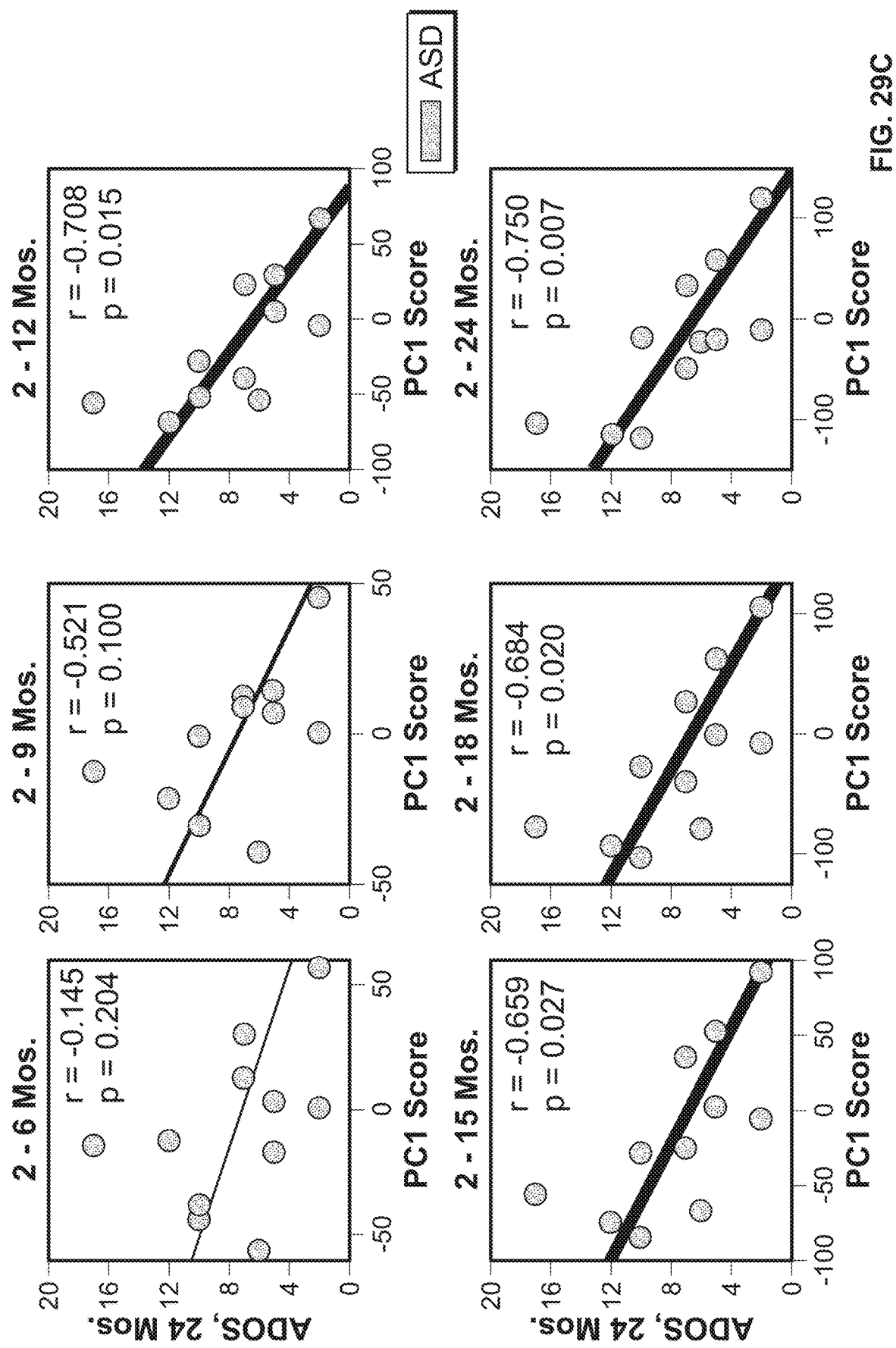
FIG. 29C show plots illustrating the influence of month-two data on the relationship between eye fixation and outcome levels of symptom severity within an ASD group, according to one embodiment of the present disclosure.
Figure 29D:
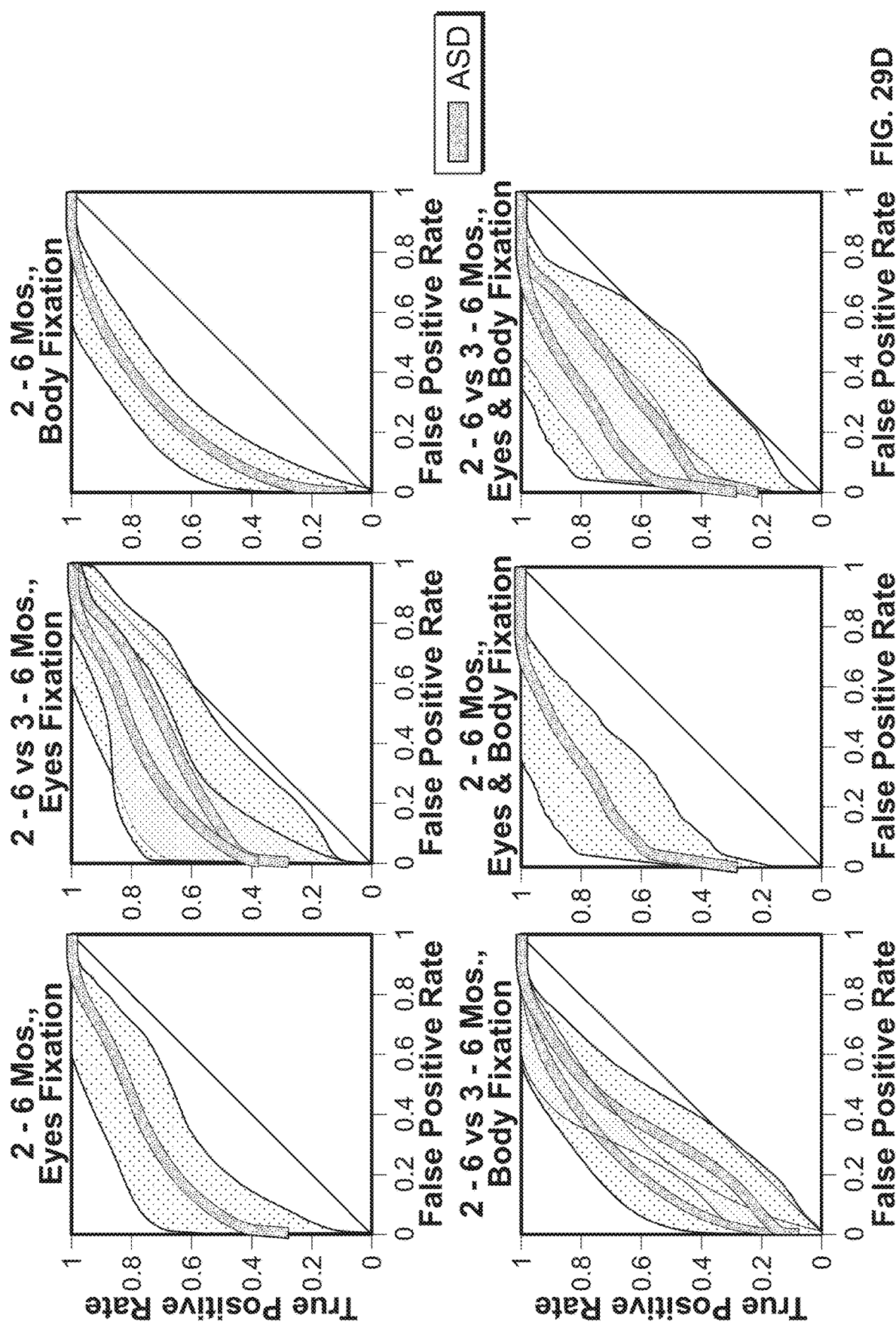
FIG. 29D shows graphs illustrating the levels of overlap between-groups remain significantly different from chance, and are not significantly different from the curves calculated when the 2-month data are included, according to one embodiment of the present disclosure.

Control comparisons tested for between-group differences in attention to task and completion of procedures. There were no between-group differences in duration of data collected per child (TD=71.25(27.66) min, ASD=64.16 (30.77) min, $t_{34}$=0.685, P=0.498); nor in the distribution of ages at which successful data collection occurred (k=0.0759, P=0.9556; 2-sample Kolmogorov-Smirnov). Calibration accuracy was not significantly different between groups, cross-sectionally, at any data collection session (all P>0.15, t<1.44; mean P=0.428), nor longitudinally, as a main effect of diagnosis ($F_{1,2968.336}$=0.202, P=0.65) or interaction of diagnosis by time ($F_{1,1300.551}$=0.027, P=0.87) (for more information regarding hierarchical linear modeling, see the Experimental Methods and Supplemental Experiment Information Sections of this disclosure). FIGS. 28A-C show graphical illustrations of calibration accuracy for the test group. In particular, in FIG. 28A the annulus marks the 95% confidence interval for calibration. In FIG. 28B, kernel density estimates plot the distribution of fixation locations relative to fixation targets to typically-developing children. In FIG. 28C, kernel density estimates plot the distribution of fixation locations relative to fixation targets to children with ASD. For the figures in FIGS. 28A-C, smoothing bandwidth for kernel density estimates was equal to 1°. The calibration processes were used as described earlier in this disclosure.

Next, the percentage of visual fixation time to eyes, mouth, body, and object regions was measured. FIG. 17C shows exemplary regions-of-interest 1706 corresponding to the exemplary screens of 1702, 1704. For each child, during each video, these measures served as the dependent variables for longitudinal analyses. Longitudinal analyses were conducted by Functional Data Analysis (FDA) and Principal Analysis by Conditional Expectation (PACE), and were repeated with traditional growth curve analysis using hierarchical linear modeling (HLM). FIGS. 17D and 17E show, respectively, graphical representations of experimental data with FDA curve fits plotting percentage of total fixation time for the test subjects on the "eye" regions-of-interest in the corresponding stimuli, from 2 until 24 months of age, for two representative children with ASD, and two representative typically-developing children.

Figure 18C:
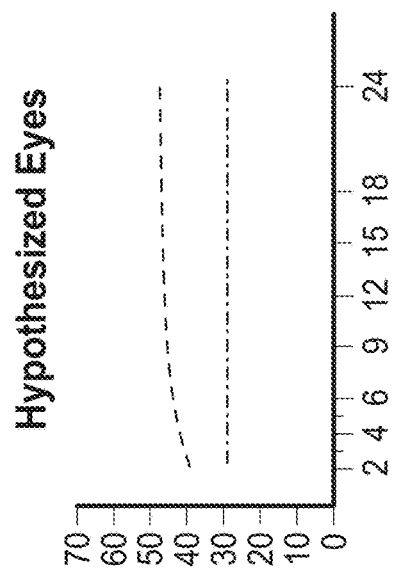
FIG. 18C shows a hypothesized growth curve representing congenital reduction in preferential attention to the eyes in individuals with ASD, according to one embodiment of the present disclosure.
Figure 18D:
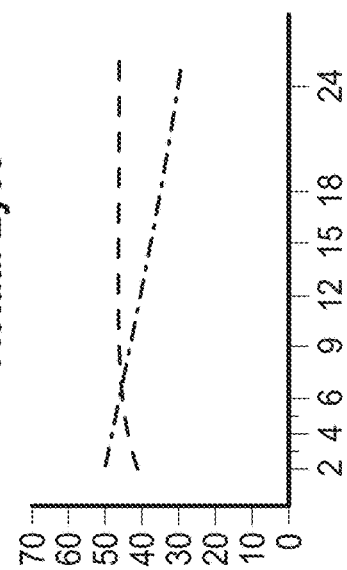
FIG. 18D shows a comparison growth curve representing actual reduction in preferential attention to the eyes in individuals with ASD, according to one embodiment of the present disclosure.
Figure 18A:
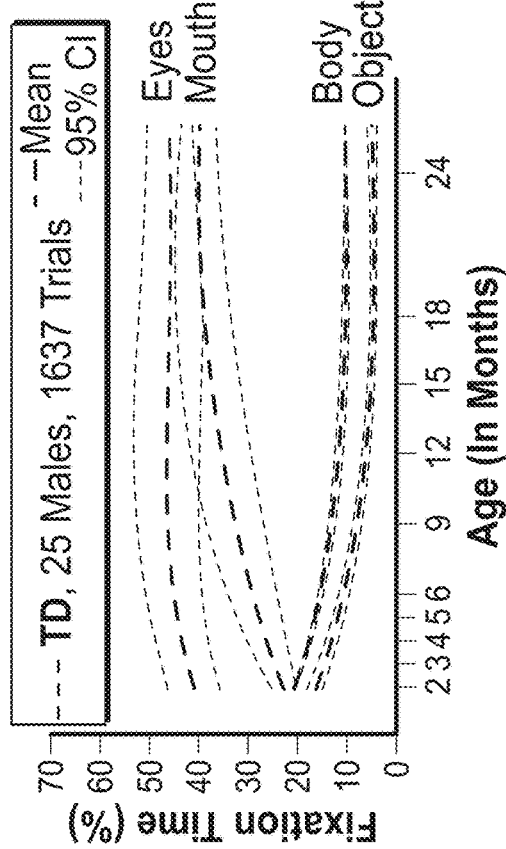
FIG. 18A shows exemplary growth curves representing social visual engagement with a stimuli (and certain regions-of-interest within the stimuli) for typically-developing children, according to one embodiment of the present disclosure.

FIG. 18A illustrates growth curves representing social visual engagement with a stimuli (and certain regions-of-interest within the stimuli) for typically-developing children. In particular, growth curves for normative social engagement show broad developmental change in typically-developing infants during the first two years of life. As shown, from 2-6 months, typically-developing infants look more at the eyes than at mouth, body, or object regions (all $F_{1,23}$>15.74, P<0.001, by functional ANOVA). FIGS. 18E, 18F, 18G, and 18H are graphical representations of longitudinal change in fixation to eyes, mouth, body, and object regions, respectively. Mouth fixation increases during the first year and peaks at approximately 18 months. Fixation on body and object regions declines sharply throughout the first year, reaching a plateau between 18 and 24 months, with greater fixation on body than on object regions at all time points ($F_{1,23}$=18.02, P<0.001). Additional experimental data relevant to this point is shown in FIGS. 22A-22L, 24A-24H, and 27A-27D.

In particular, FIGS. 22A-22L are data plots illustrating developmental differences in visual fixation between 2 and 6 months of age, with fixation relative to regions-of-interest of an actor's eyes (FIGS. 22A-22C), actor's mouth (FIGS. 22D-22F), actor's body (FIGS. 22G-22I), and objects (FIGS. 22J-22L). In these figures, darkly-shaded data markers indicate the interquartile range (spanning $25^{th}$ to $75^{th}$ percentiles). The data show significant associations with chronological age, but the slopes of the associations differ for ASD and typically-developing outcome groups.

Figure 24I:
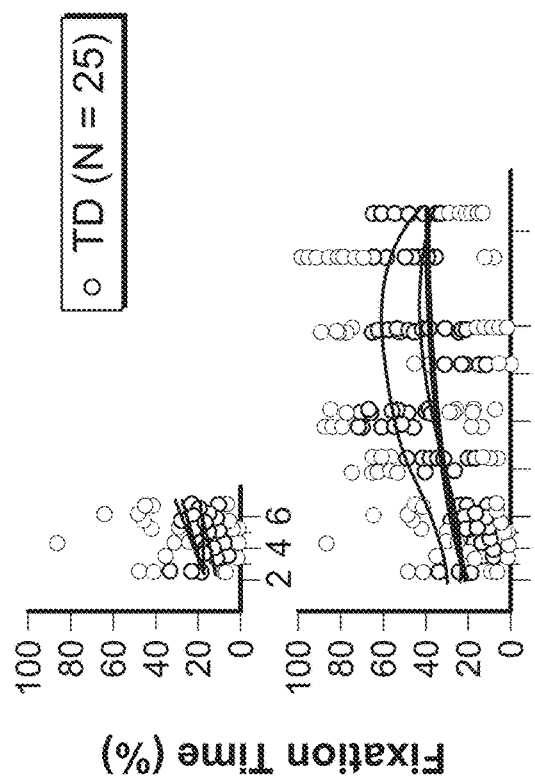
FIGS. 24I-L show data plots illustrating mean fixation curves with respect to an actor's eyes, mouth, body, or an object, respectively, between 2 and 24 months of age in typically developing children for one experimental test group, according to one embodiment of the present disclosure.
Figure 24J:
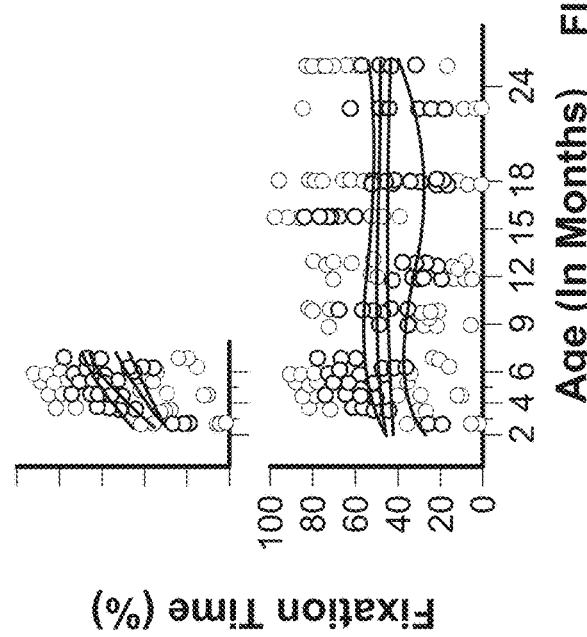
Figure 24K:
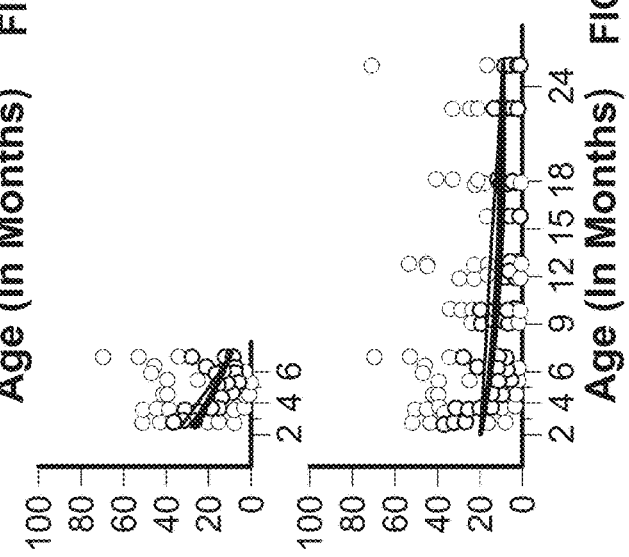
Figure 24L:
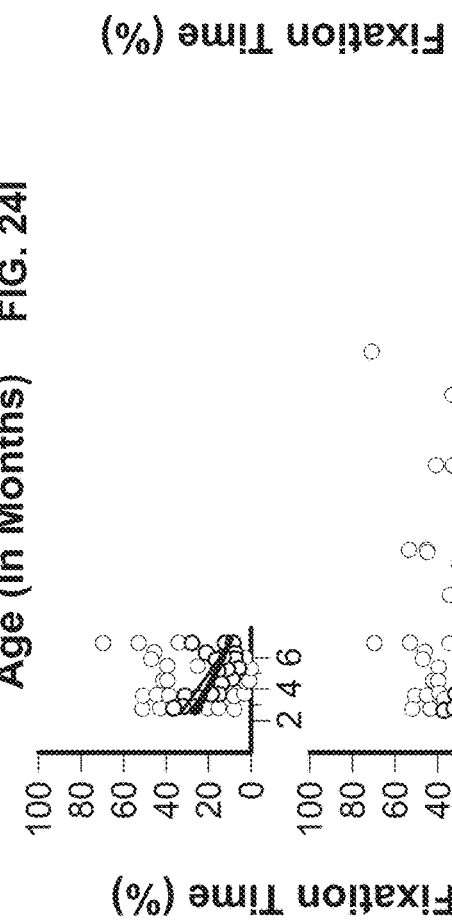

FIGS. 24A-24H are data plots illustrating developmental change in visual fixation between 2 and 24 months of age in typically-developing children. Raw eye tracking data plots are shown with respect to an actor's eyes (FIG. 24A), actor's mouth (FIG. 24C), actor's body (FIG. 24E), and an object (FIG. 24G). In these figures, darkly-shaded data markers indicate the interquartile range (spanning $25^{th}$ to $75^{th}$ percentiles). The black lines indicate mean growth curves via hierarchical linear modeling (HLM). Also shown are mean fixation curves with 95% confidence intervals for fixation with respect to an actor's eyes (FIG. 24B), an actor's mouth (FIG. 24D), an actor's body (FIG. 24F), and objects (FIG. 24H) between 2 and 24 months for typically-developing children.

FIGS. 27A-27D are graphs illustrating mean fixation curves by PACE/FDA with the effects of adding or subtracting each principal component function for eye fixation, mouth fixation, body fixation, and object fixation, respectively, relating to regions-of-interest in a stimuli. The graphs of FIGS. 27A-27D include data for bot typically-developing children and those with ASD. For each region and each test group, the number of plots is dictated by the number of PC functions.

Figure 18B:
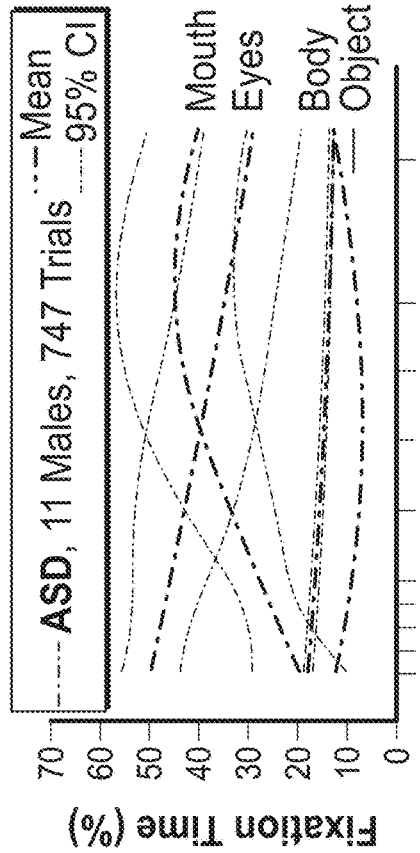
FIG. 18B shows exemplary growth curves representing social visual engagement with a stimuli (and certain regions-of-interest within the stimuli) for children later diagnosed with ASD, according to one embodiment of the present disclosure.
Figures 18E, 18F:
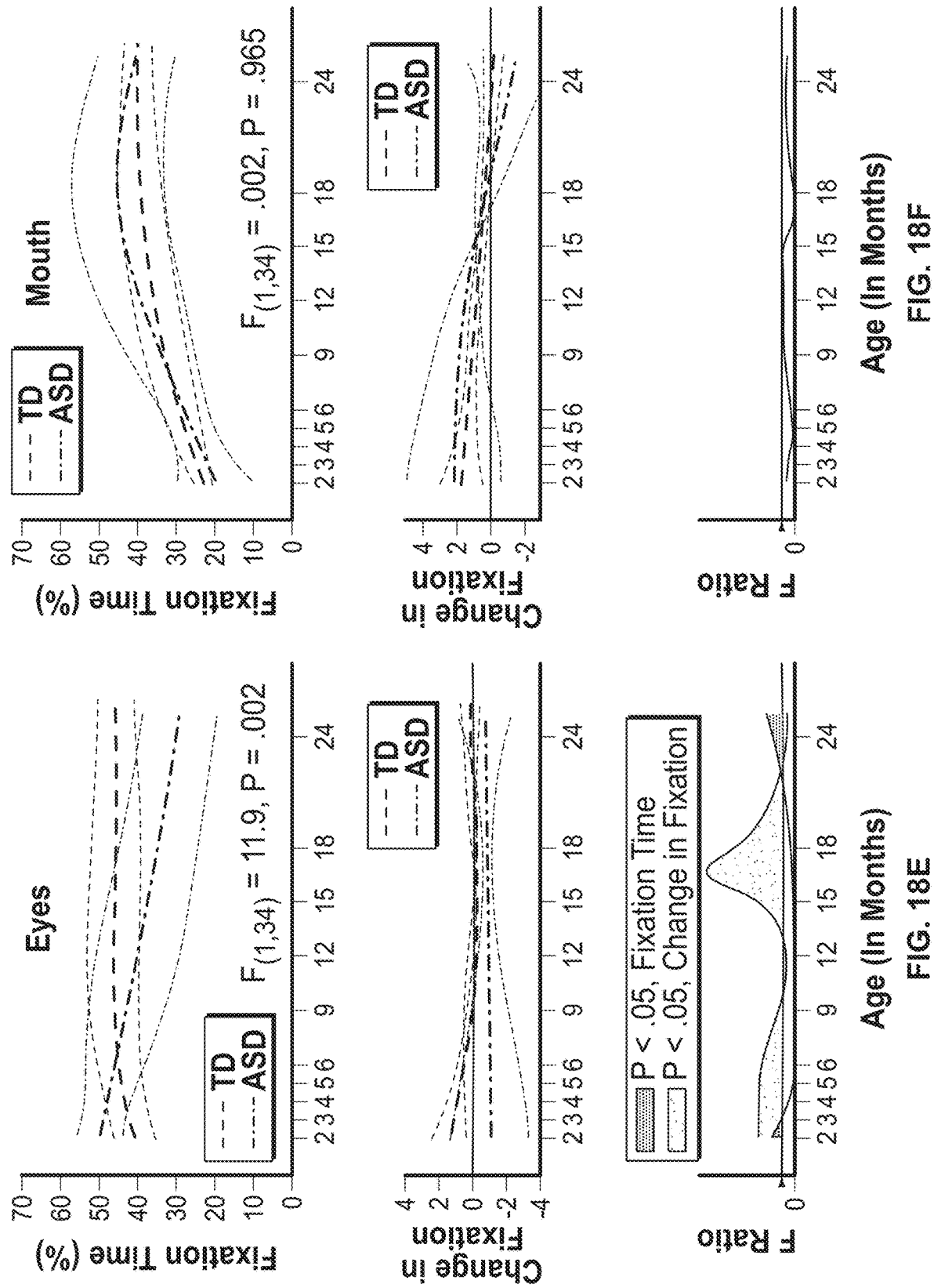
FIGS. 18E, 18F, 18G, and 18H show graphical representations of longitudinal change in fixation to eyes, mouth, body, and object regions, respectively, for certain test subjects, according to one embodiment of the present disclosure.
Figures 18G, 18H:
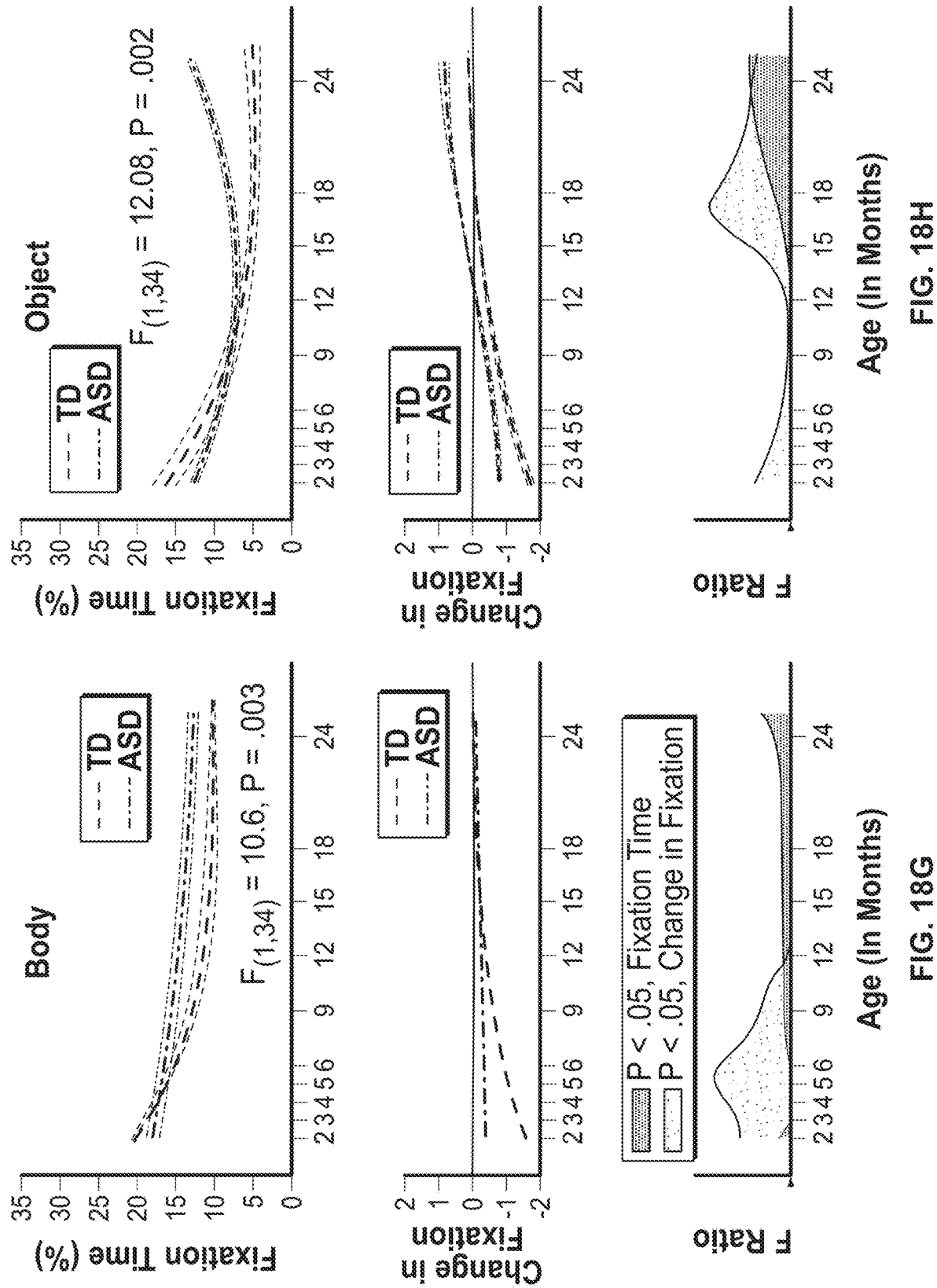

Referring again to FIG. 18, the graph in FIG. 18B illustrates growth curves representing social visual engagement with a stimuli (and certain regions-of-interest within the stimuli) for children later diagnosed with ASD. As shown, in infants later diagnosed with ASD, growth curves of social visual engagement follow a different developmental course than those of typically-developing children. From 2 until 24 months of age, eye fixation declines, arriving by 24 months at a level that is approximately ½ that of typically-developing children (see FIG. 18E). Fixation on others' mouths increases from month 2 until approximately month 18 (see FIG. 18F). Fixation on others' bodies declines in children with ASD, but at less than half the rate of TD children, stabilizing at a level 25% greater than typical (see FIG. 18G). Object fixation also declines more slowly in children with ASD, and increases during the $2^{nd}$ year (see FIG. 18H), rising by 24 months to twice the level of typical controls. Additional experimental data relevant to this point is shown in FIGS. 22A-22L, 25A-25H, and 27A-27D.

In particular, FIGS. 25A-25H are data plots illustrating developmental change in visual fixation between 2 and 24 months of age in children with ASD. Raw eye tracking data plots are shown with respect to an actor's eyes (FIG. 24A), actor's mouth (FIG. 24C), actor's body (FIG. 24E), and an object (FIG. 24G). In these figures, darkly-shaded data markers indicate the interquartile range (spanning $25^{th}$ to $75^{th}$ percentiles). The black lines indicate mean growth curves via hierarchical linear modeling (HLM). Also shown are mean fixation curves with 95% confidence intervals for fixation with respect to an actor's eyes (FIG. 24B), an actor's mouth (FIG. 24D), an actor's body (FIG. 24F), and objects (FIG. 24H) between 2 and 24 months for children with ASD.

Between-group comparison of entire 2- to 24-month growth curves by functional ANOVA reveals significant differences in eye fixation (see FIG. 18E, $F_{1,34}=11.90$, P=0.002); in body fixation (see FIG. 18G, $F_{1,34}=10.60$, P=0.003); and in object fixation (see FIG. 18H, $F_{1,34}=12.08$, P=0.002); but not in mouth fixation (see FIG. 18F, $F_{1,34}=0.002$, P=0.965) (Bonferroni corrections for multiple comparisons, $\alpha=0.0125$). Related analyses, including HLM, are provided in greater detail below in the Experimental Methods and Supplemental Experiment Information Sections of this disclosure, as well as in FIGS. 24A-24H, 25A-25H, 27A-27D, and 28A-28C, all of which have been discussed previously above.

Contrary to conventional belief, the data for children with ASD show developmental decline in eye fixation from 2 until 24 months of age, with average levels of ASD eye looking that appear to begin in the normative range. This represents an unexpected result that is inapposite to conventional wisdom in this area.

Figure 21A:
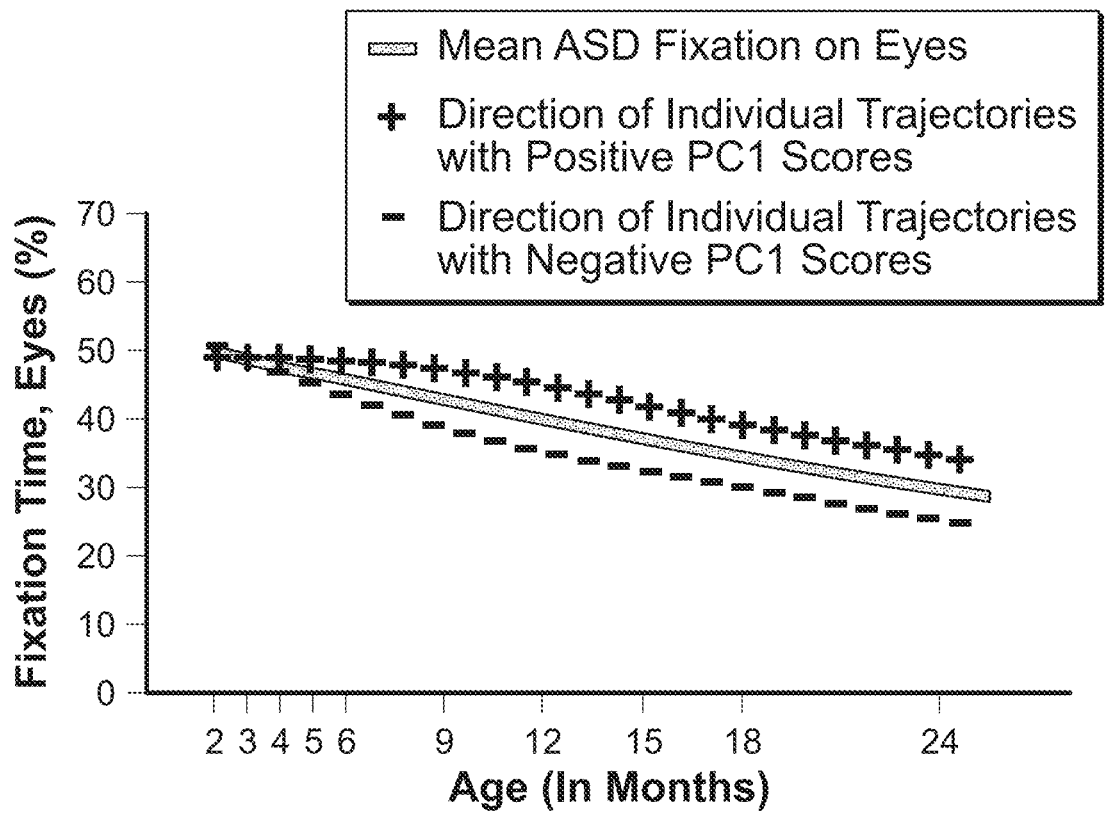
FIG. 21A shows a graph illustrating population mean for fixation to the eyes of an actor in a stimuli in children with ASD plotted with lines indicating direction of individual trajectories having positive principal component one (PC1) scores or negative PC1 scores, according to one embodiment of the present disclosure.
Figure 21B:
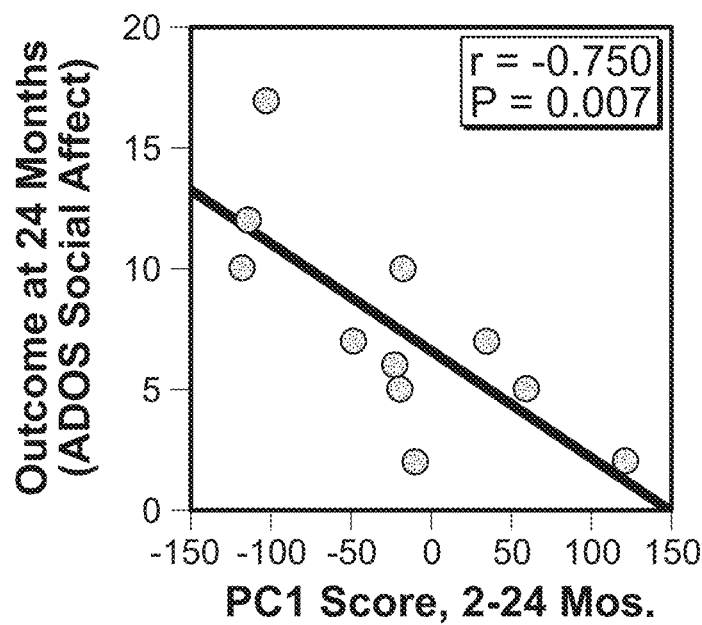
FIG. 21B shows a graph illustrating outcome levels of social disability (as measured by ADOS Social-Affect) as a function of decline in eye fixation (measured as eyes PC1 score), according to one embodiment of the present disclosure.
Figure 21C:
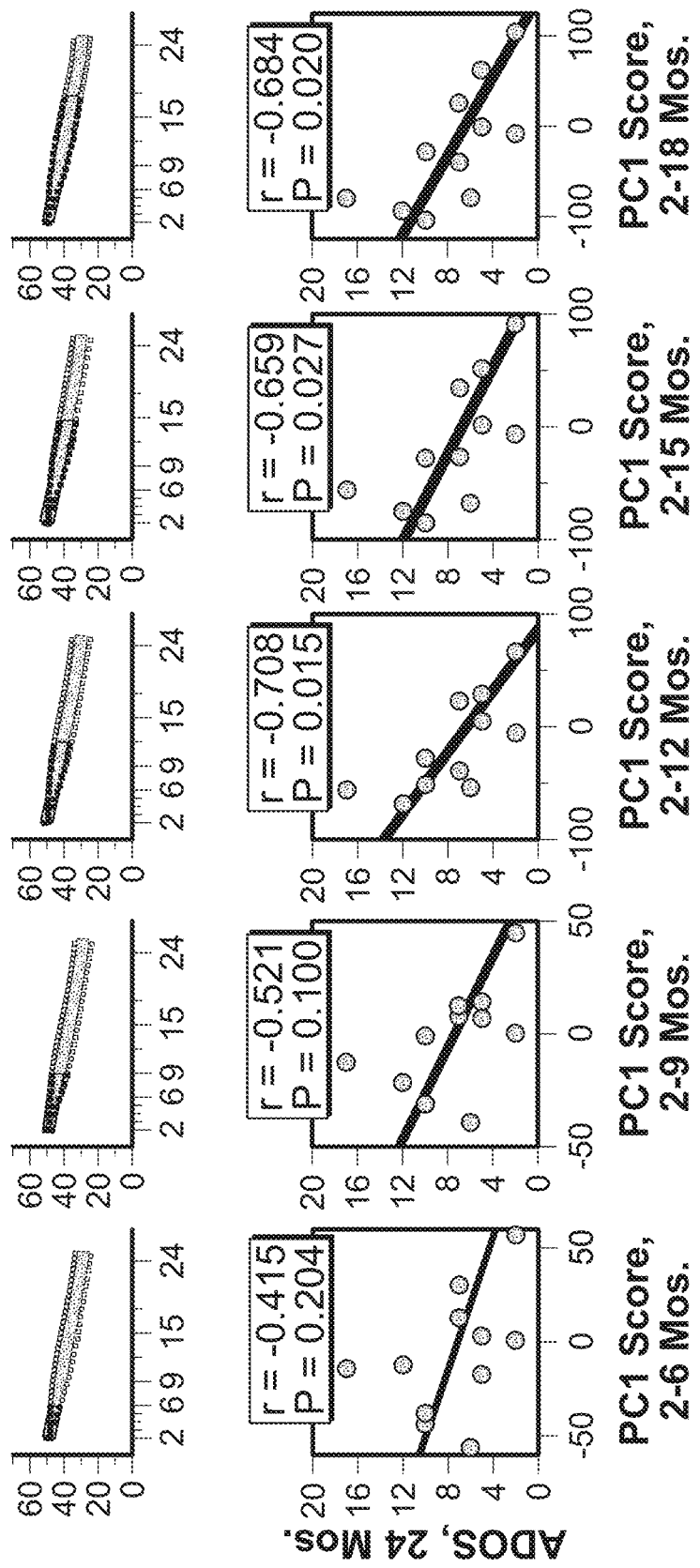
FIG. 21C shows a series of graphs illustrating outcome levels of social disability as a function of decline in eye fixation using subsets of the longitudinal data, according to one embodiment of the present disclosure.

The relationship between longitudinal eye fixation and dimensional level of social-communicative disability was tested via regression. As shown in FIGS. 21A-21C, steeper decline in eye fixation is strongly associated with more severe social disability: $r_{(9)}=-0.750$ [$-0.27--0.93$, 95% CI], P=0.007. Generally, FIG. 21A is a graph illustrating population mean for fixation to the eyes of an actor in a stimuli in children with ASD plotted with lines indicating direction of individual trajectories having positive principal component one (PC1) scores or negative PC1 scores. FIG. 21B is a graph illustrating outcome levels of social disability (as measured by ADOS Social-Affect) as a function of decline in eye fixation (measured as eyes PC1 score). FIG. 21C is a series of graphs illustrating outcome levels of social disability as a function of decline in eye fixation using subsets of the longitudinal data. In an exploratory analysis, sub-sets of the available data were also tested: that is, the experiment measured decline in eye fixation using only data collected between months 2 through 6, excluding data collected thereafter; then using only data collected between months 2-9; 2-12; etc.). The relationship between decline in eye fixation and outcome becomes a statistical trend by 2-9 months (P=0.100), and is statistically significant thereafter. Although these latter analyses were exploratory, they indicate the potential clinical significance of these early behaviors.

The present experimental design densely sampled the first 6 months of life in order to test the relationship between early looking behavior and later categorical outcome. FIGS. 22A-22C, referenced above, show raw eye fixation data collected in the first 6 months. Eye fixation data for both groups show significant associations with chronological age ($F_{1,114.237}=9.94$, P=0.002 for typically-developing eye fixation, $F_{1,41.609}=9.62$, P=0.003 for ASD eye fixation), but the slopes of the associations are in opposite directions: increasing at +3.6% per month for typically-developing children [1.3-5.9, 95% CI], and decreasing at -4.8% per month for ASD [-7.9--1.7, 95% CI]. A similar difference is observed for body fixation (see FIGS. 22G-22I): body fixation is declining in typically-developing children but is not declining in those later diagnosed with ASD (-4.3% per month [-5.4--3.1] for typically-developing, $F_{1,211.856}=54.83$, P<0.001; 0.3% per month for ASD [-1.2-1.7], $F_{1,241.320}=0.11$, P=0.739). For both regions, there are significant interactions of Diagnosis by Age: eyes, $F_{1,787.928}=9.27$, P=0.002; and body, $F_{1,25.557}=5.88$, P=0.023 (HLM).

As a control, the experiment tested whether there were between-group differences in levels of looking at the video stimuli, irrespective of content region. There were no between-group differences in levels of fixation or saccading, respectively, either as a main effect of diagnosis [$F_{(1,21.652)}=0.958$, P=0.339; $F_{(1,27.189)}=0.250$, P=0.621] or as an interaction of diagnosis by age [$F_{(1,20.026)}=0.880$, P=0.359; $F_{(1,260.430)}=0.561$, P=0.460], as shown in FIGS. 23A-23F. In particular, FIGS. 23A-23F show graphs illustrating data plots of percentage of total time spent fixating and saccading between 2 and 6 months of age. The raw eye tracking data is shown for percentage of total time spent fixating (see FIGS. 23A-23C) and time spent saccading (see FIGS. 23D-23F).

Figure 19B:
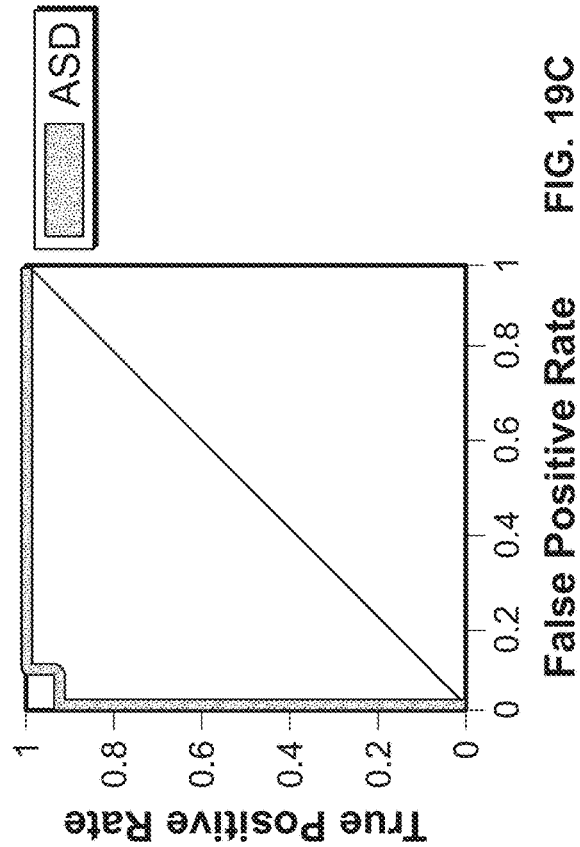
FIG. 19B shows a plot in change in eye fixation for an experimental group between ages 2 and 6 months, according to one embodiment of the present disclosure.
Figure 19C:
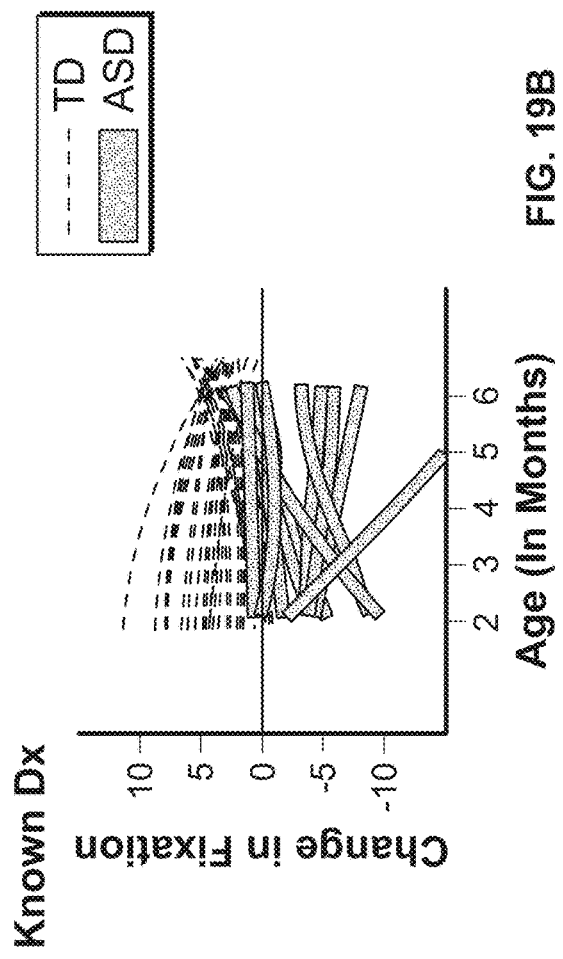
FIG. 19C shows a graph illustrating the extent of between-group overlap in distributions of change-in-fixation data, for one experimental test group according to one embodiment of the present disclosure.
Figure 19A:
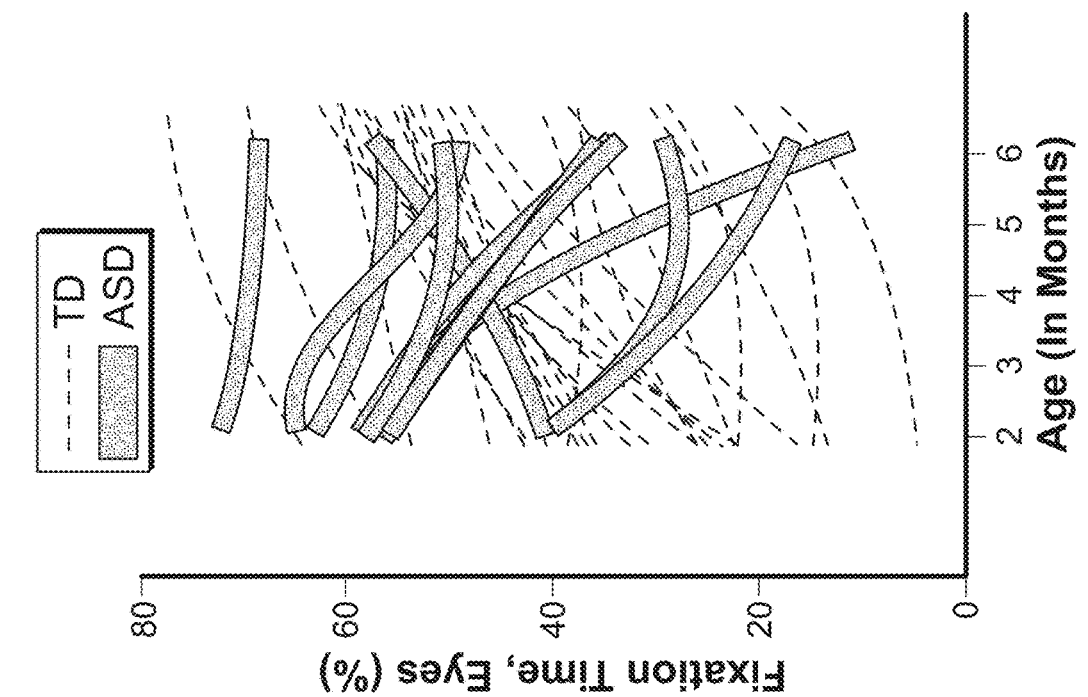
FIG. 19A shows a plot of individual growth curves for levels of eye fixation for an experimental group between ages 2 and 6 months, according to one embodiment of the present disclosure.

Given the variability in infant looking, the experiment measured the extent of overlap in distributions for measures of fixation in typically-developing infants relative to infants later diagnosed with ASD. FIG. 19A is a plot of individual growth curves for levels of eye fixation between ages 2 and 6 months, while FIG. 19B shows a plot in change in eye fixation over the same time span. Mean individual levels of change in fixation between 2 and 6 months show minimal overlap between groups (see FIG. 19C, which illustrates the extent of between-group overlap in distributions of change-in-fixation data). To validate the estimates shown in these figures and avoid potential bias, internal validation was performed.

Figure 19E:
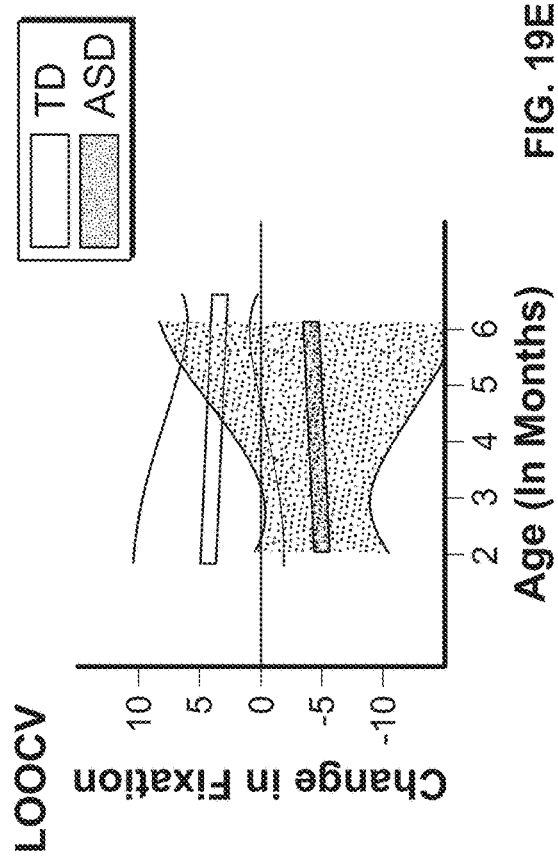
FIGS. 19D-19E show graphs illustrating LOOCV mean and 95% prediction intervals for individual trajectories of eye fixation and change-in-fixation data, respectively, for one experimental test group, according to one embodiment of the present disclosure.
Figure 19F:
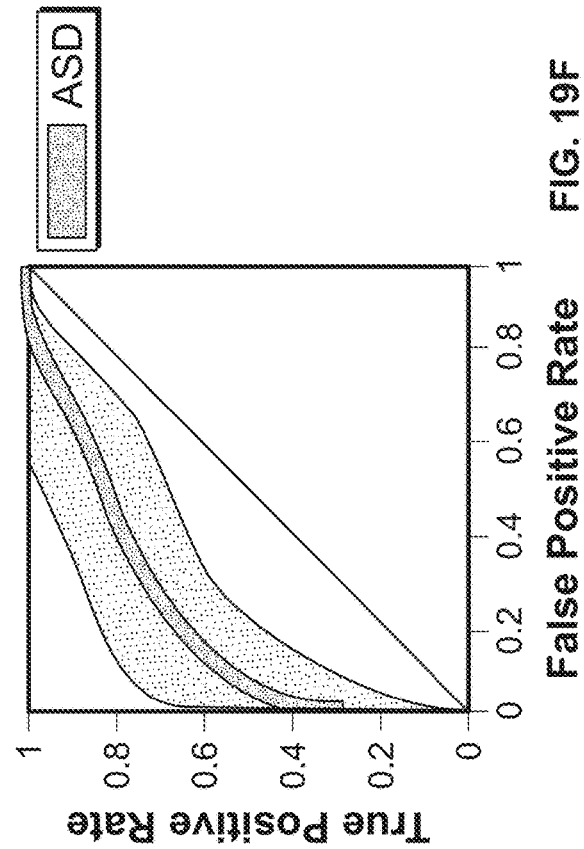
FIGS. 19F-19L show graphs illustrating the extent of between-group overlap in change-in-fixation data for one experimental test group, according to one embodiment of the present disclosure.
Figure 19D:
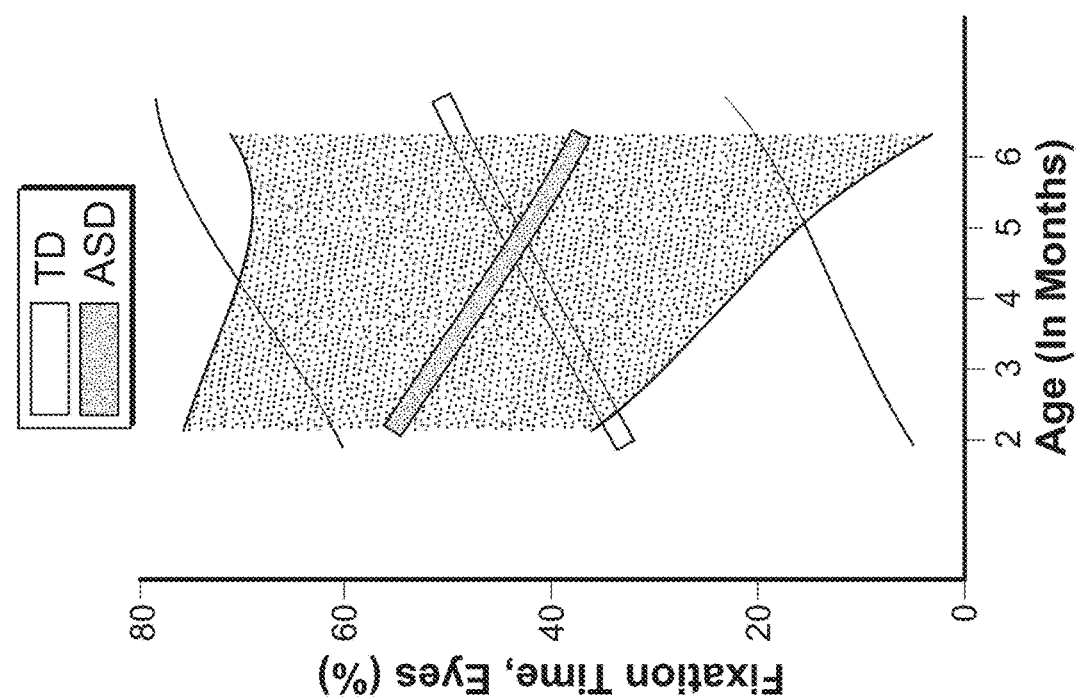
Figure 19H:
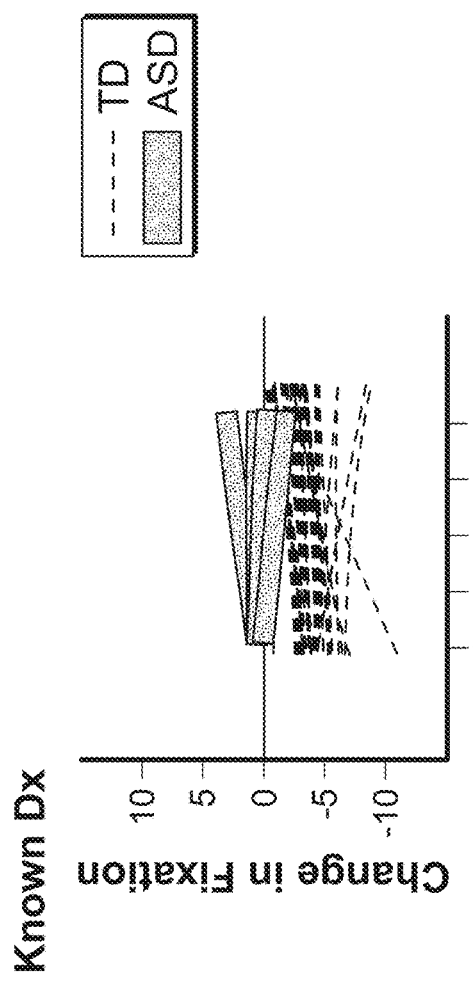

As an internal validation, the experiment used leave-one-out cross-validation (LOOCV), partitioning the data into subsamples so that each infant was tested as a validation case (i.e., presuming unknown diagnostic outcome) in relation to the remainder of the data set. FIGS. 19D-19E illustrate LOOCV mean and 95% prediction intervals for individual trajectories of eye fixation and change-in-fixation data, respectively. FIG. 19F is a graph illustrating the extent of between-group overlap in change-in-fixation data. The results indicate relatively low levels of overlap between groups (as illustrate in FIG. 19F). The same analyses were conducted for rates-of-change in body fixation (see FIGS. 19G-19I and 19J-19L, respectively). While the area under each receiver operating characteristic (ROC) curve is smaller (as expected) for the internal validations as compared with estimates based on known diagnostic outcomes, the 95% confidence intervals clearly indicate less overlap than expected by chance.

Figure 19I:
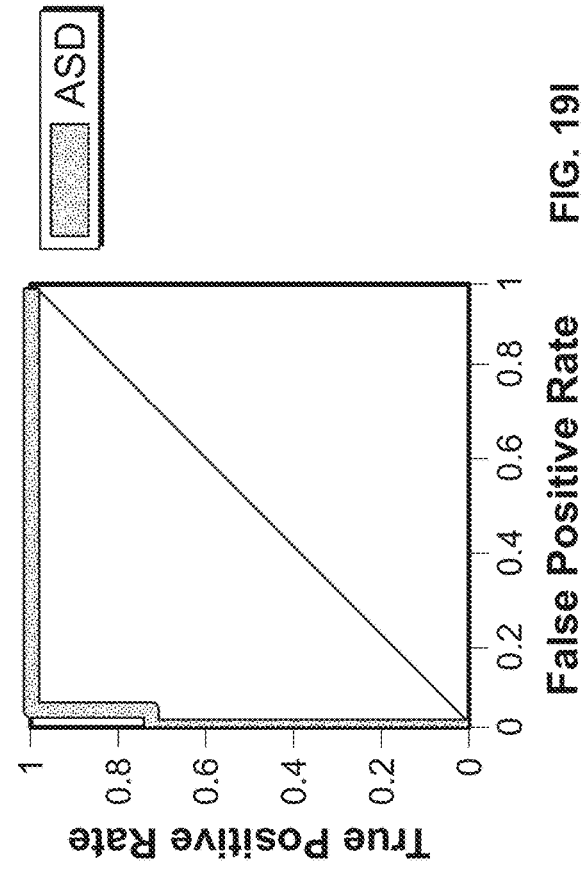
Figure 19G:
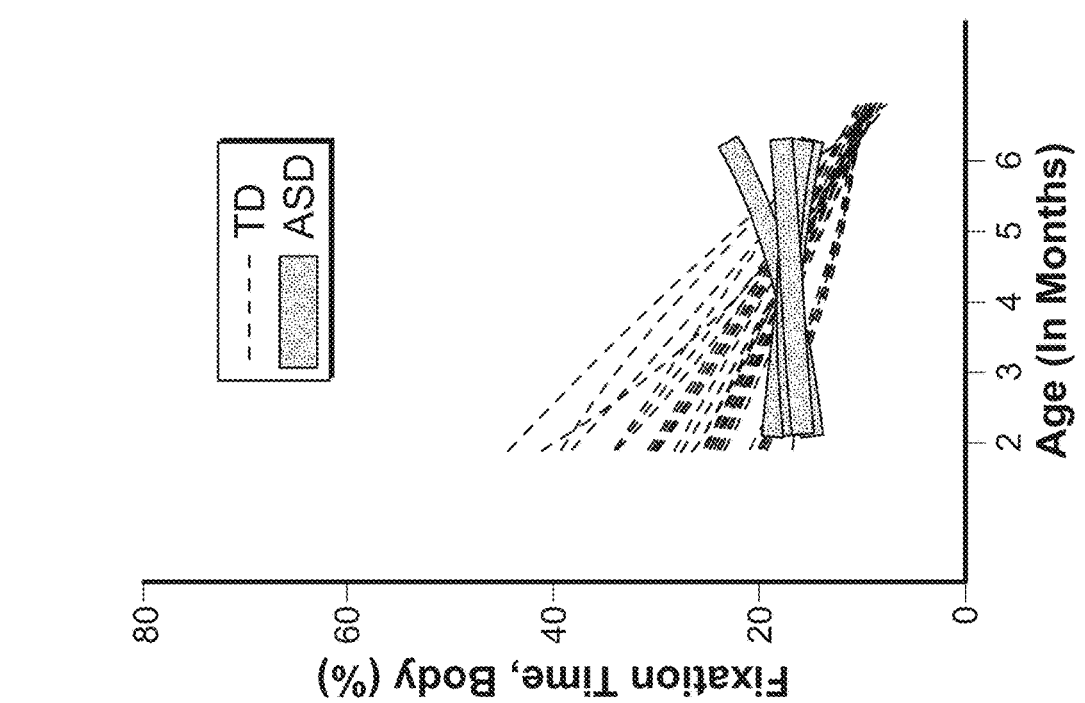
Figure 19K:
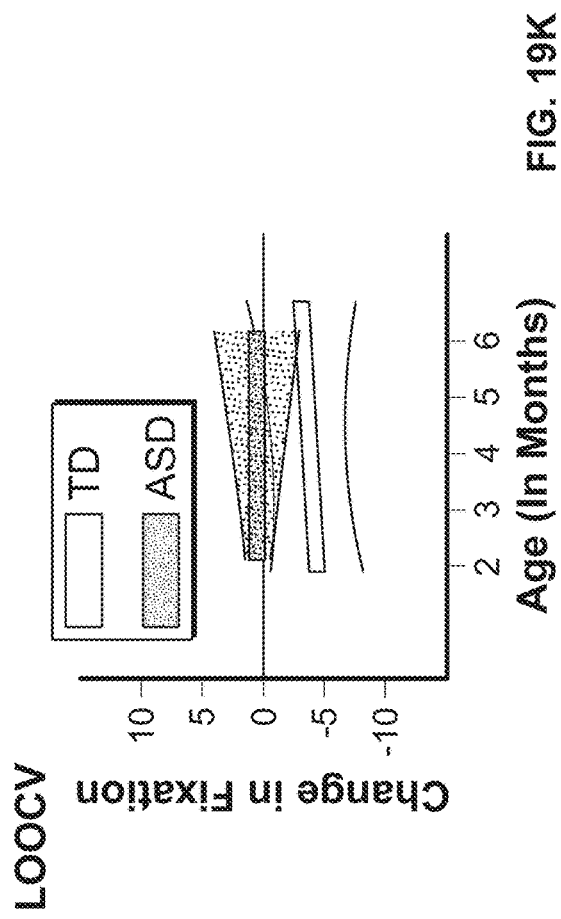
Figure 19L:
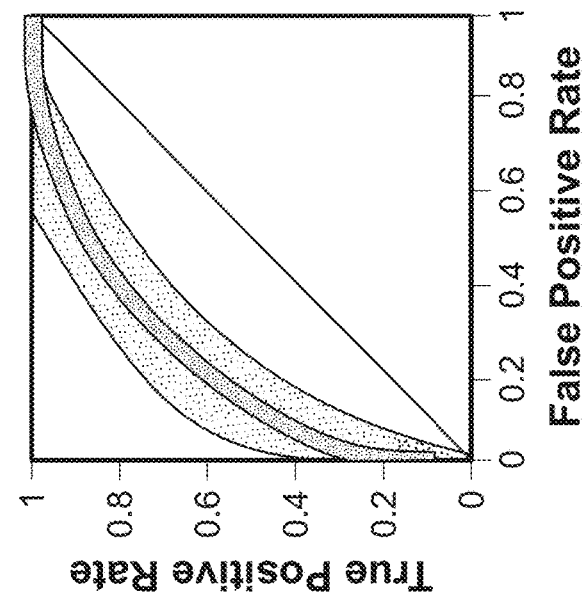
Figure 19J:
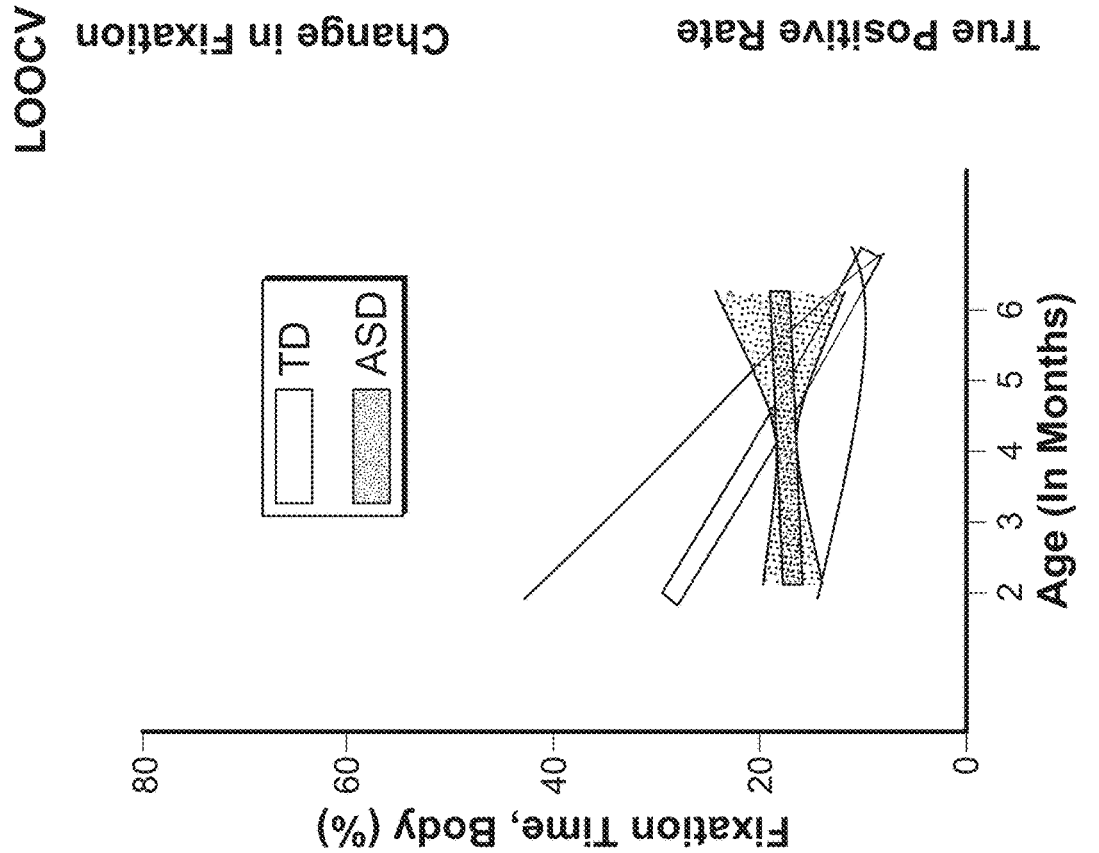
Figure 19M:
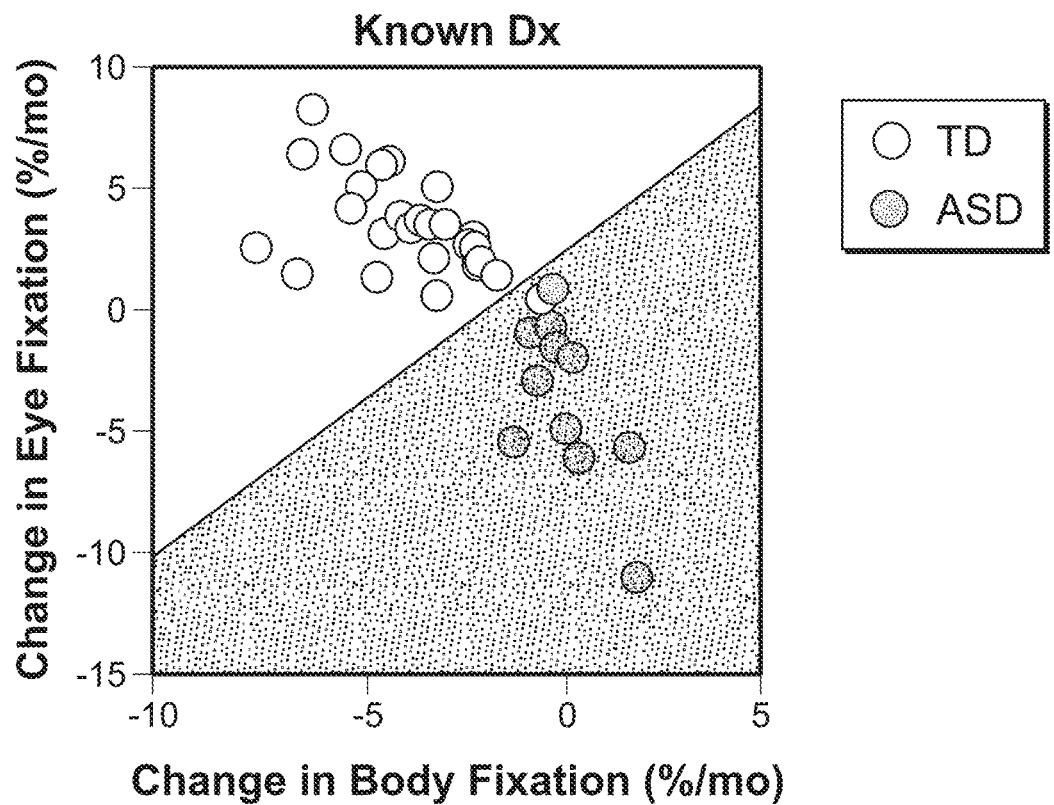
FIG. 19M shows a graph illustrating a joint distribution of the change in eye and body fixation for one experimental test group, according to one embodiment of the present disclosure.
Figure 19N:
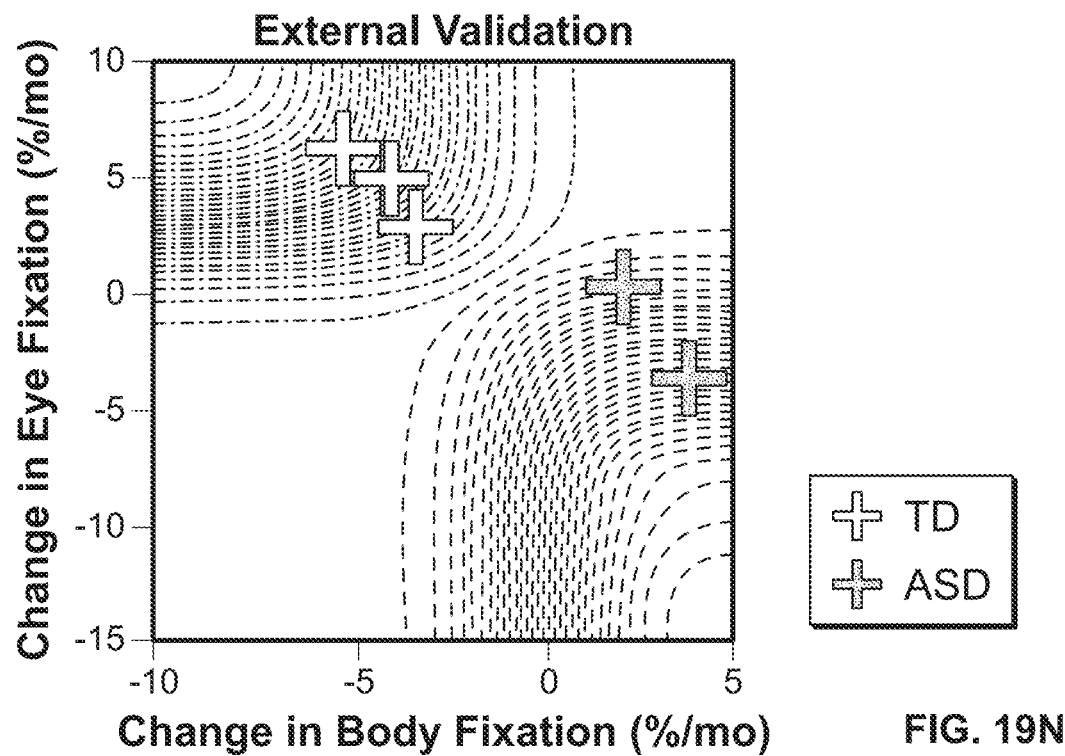
FIG. 19N shows a graph illustrating validation of the change in eye and body fixation for one experimental test group, according to one embodiment of the present disclosure.

As an external validation, the experiment used the same technique to test 6 male infants who were not part of the original sample. Two of the six children had reached the age of 36 months, with confirmed ASD diagnosis, while 4 of the children were low-risk recruits, at least 22 months of age at the time of the experiments, with no clinical concerns of ASD. In relation to the original sample's change in eye and body fixation (as shown in FIG. 19M), these 6 independent test cases show similar trajectories within the first 6 months (as shown in FIG. 19N). While this validation set is small, the probability of obtaining all 6 of these results in the predicted direction by chance alone is P=0.0156 (equal to the chance of correctly predicting the outcome, 0.5, on each of 6 occasions, $0.5^6$).

Having observed these differences between clearly-defined extremes of social functioning at outcome (ASD and TD), the data from the remaining high-risk males was then analyzed. These siblings were identified clinically as either unaffected at 36 months (HR-ASD_No-Dx) or as exhibiting subthreshold signs of ASD (also called the "Broader Autism Phenotype", or BAP, abbreviated here as HR-ASD_BAP). For change in eye fixation between 2 and 6 months of age, ROC curves in FIGS. 20A, 20B, and 20C quantify the overlap in measures relative to outcome (95% confidence intervals by LOOCV). The behaviour of unaffected siblings (HR-ASD_NoDx) is highly overlapping with that of TD children (as shown in the graph of FIG. 20C), while the behaviour of infants later diagnosed with ASD (as shown in the graph of FIG. 20A), and that of infants with subthreshold signs (as shown in the graph of FIG. 20B), clearly differs from typical controls.

Figures 20D, 20E:
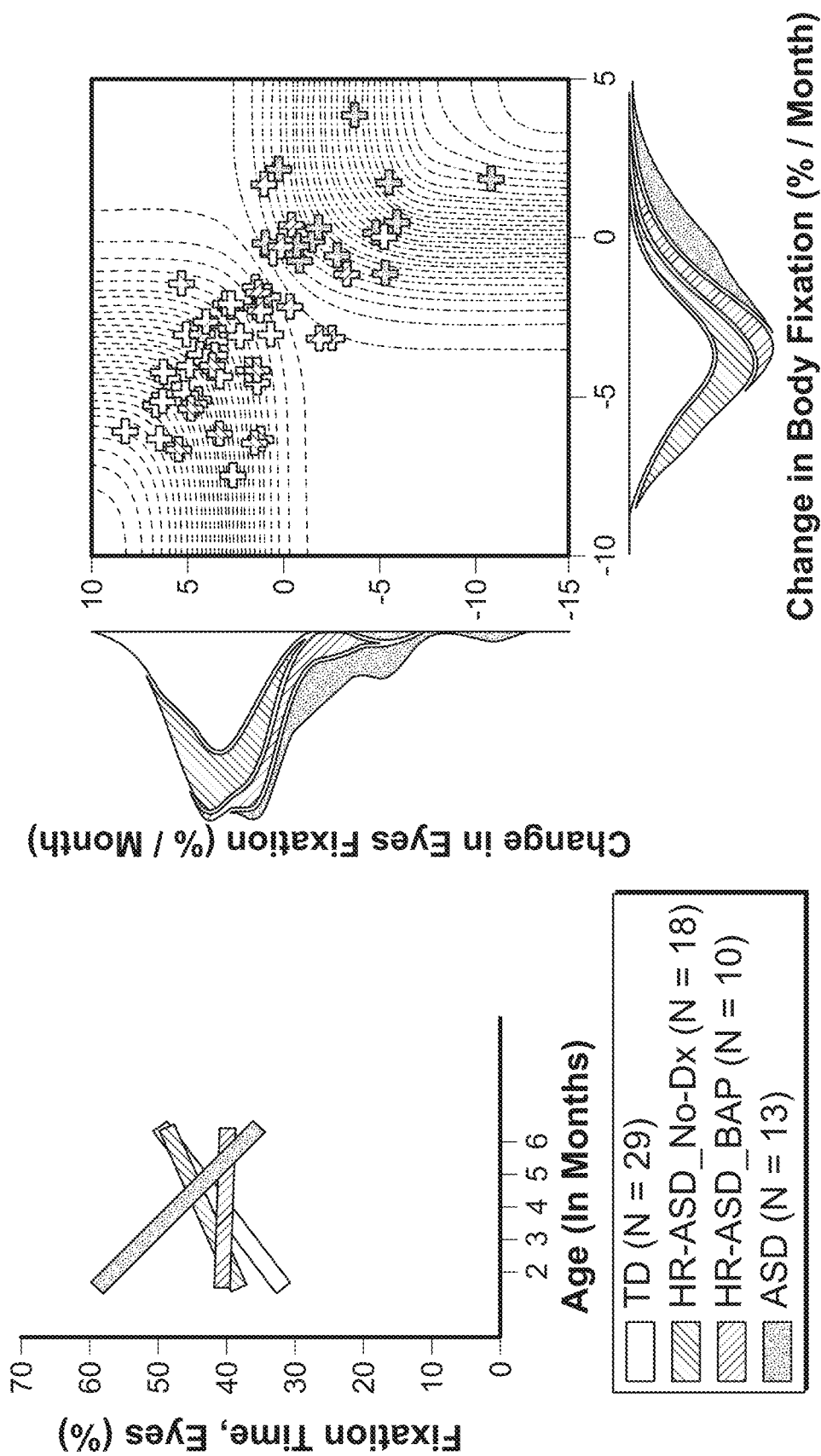
FIG. 20D shows a graph illustrating how eye fixation varies systematically across all outcome groups, with significant interaction of Outcome by Age (by HLM), for one experimental test group, according to one embodiment of the present disclosure.
FIG. 20E shows a dimensional plot, across the full spectrum of social ability to disability, of individual results for change in eye and body fixation (with respect to eye and body regions-of-interest of persons shown in a stimuli, according to one embodiment of the present disclosure.
Figure 26A:
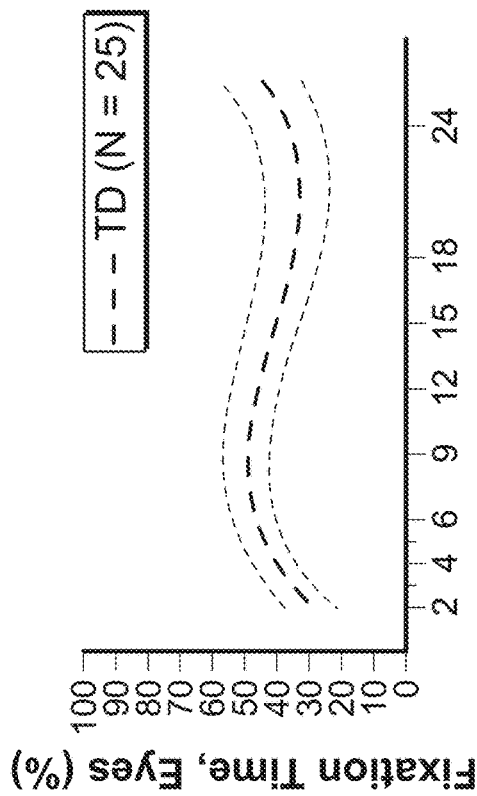
Figure 26B:
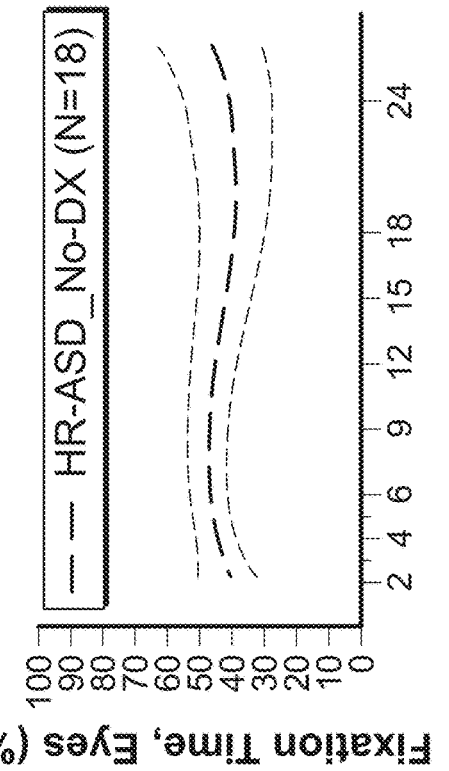
Figure 26C:
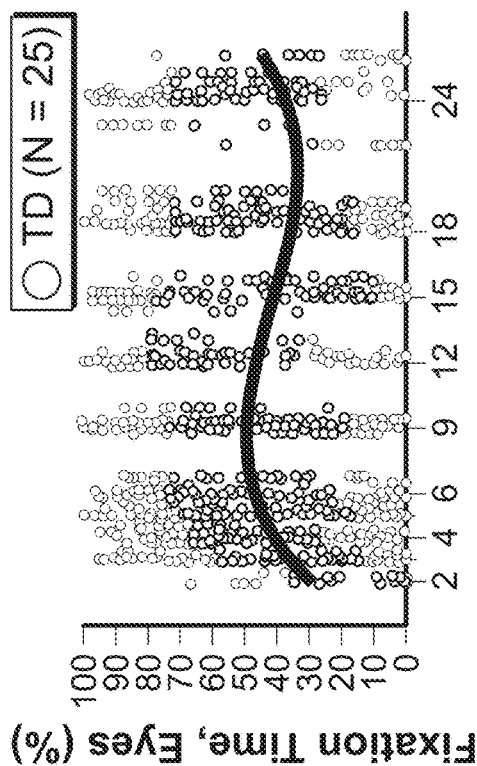
Figure 26D:
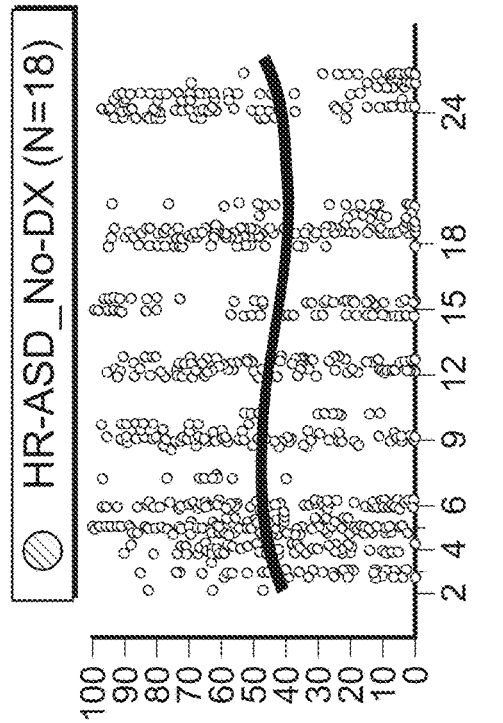
Figure 27A:
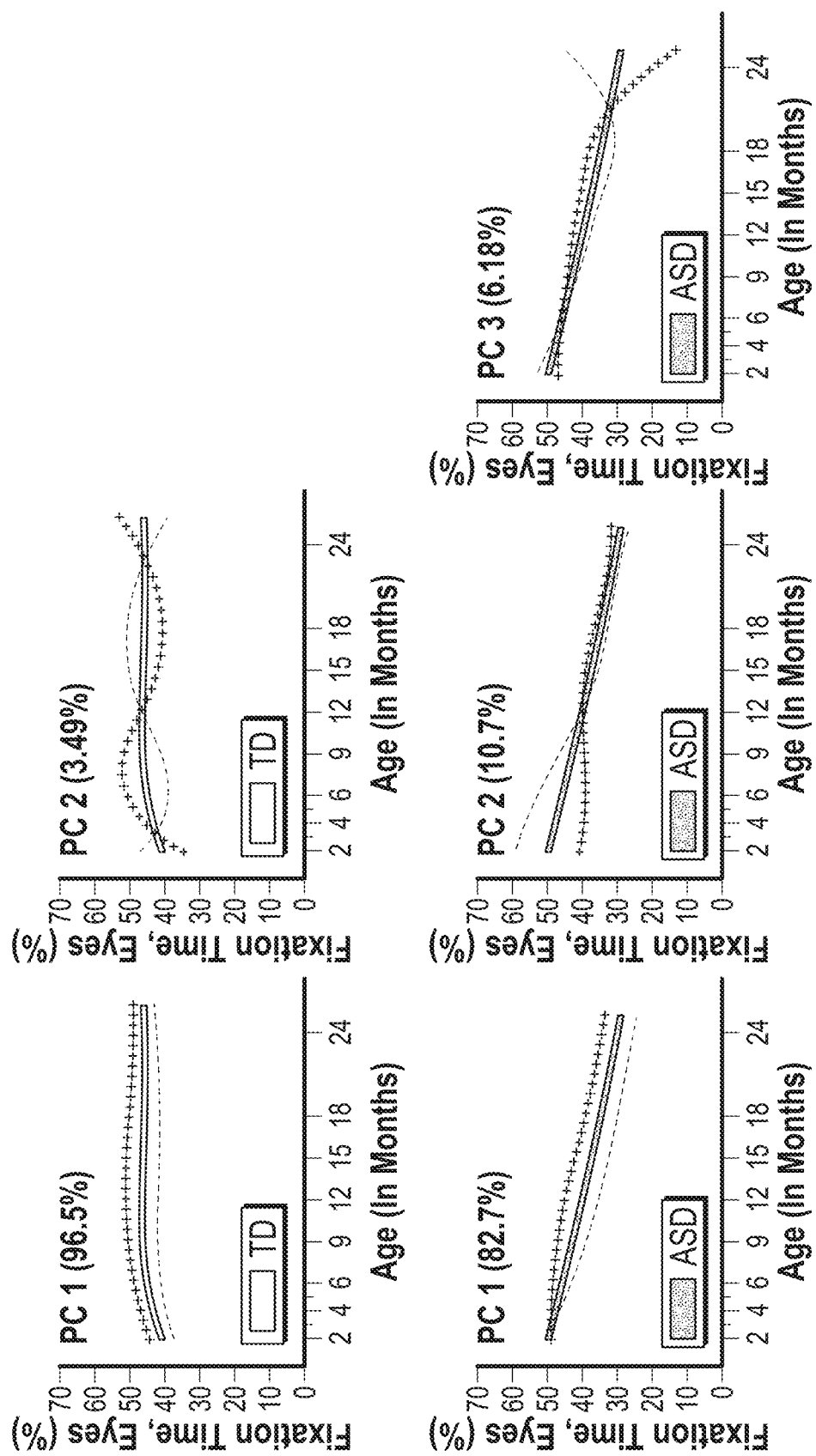
FIGS. 27A-27D show graphs illustrating mean fixation curves by PACE/FDA with the effects of adding or subtracting each principal component function for eye fixation, mouth fixation, body fixation, and object fixation, respectively, relating to regions-of-interest in a stimuli for one experimental test group, according to one embodiment of the present disclosure.
Figure 27B:
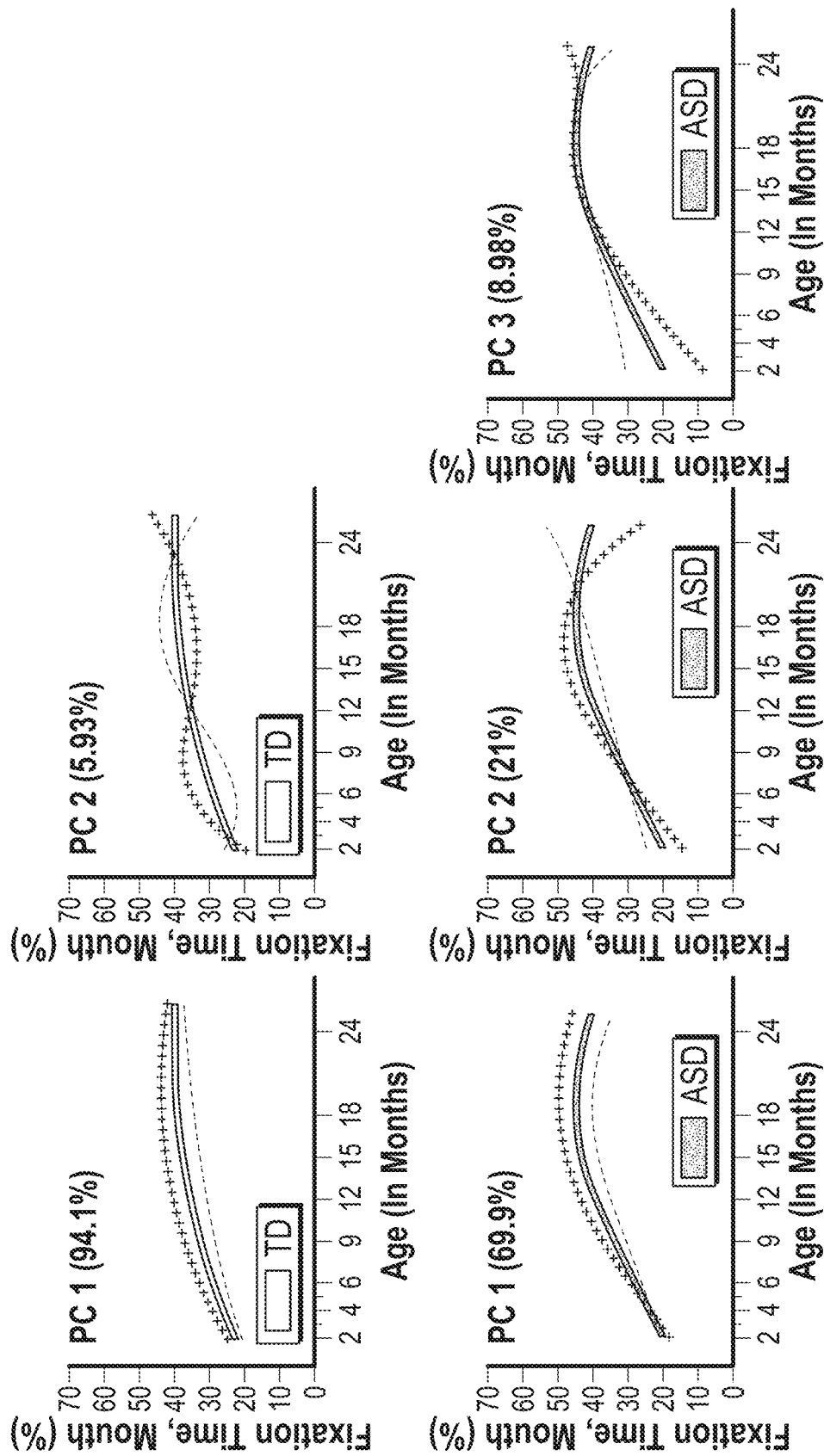
Figure 27C:
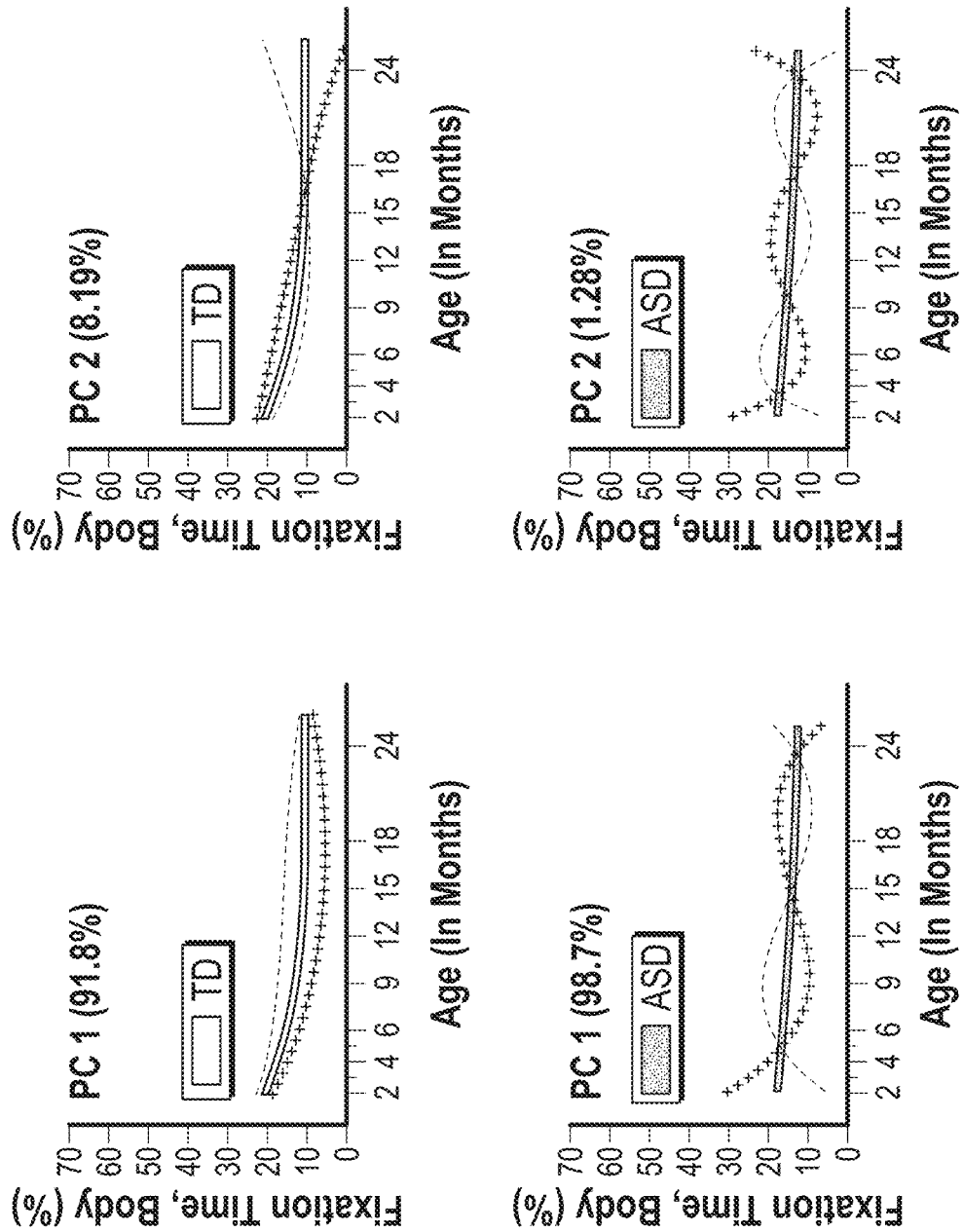
Figure 27D:
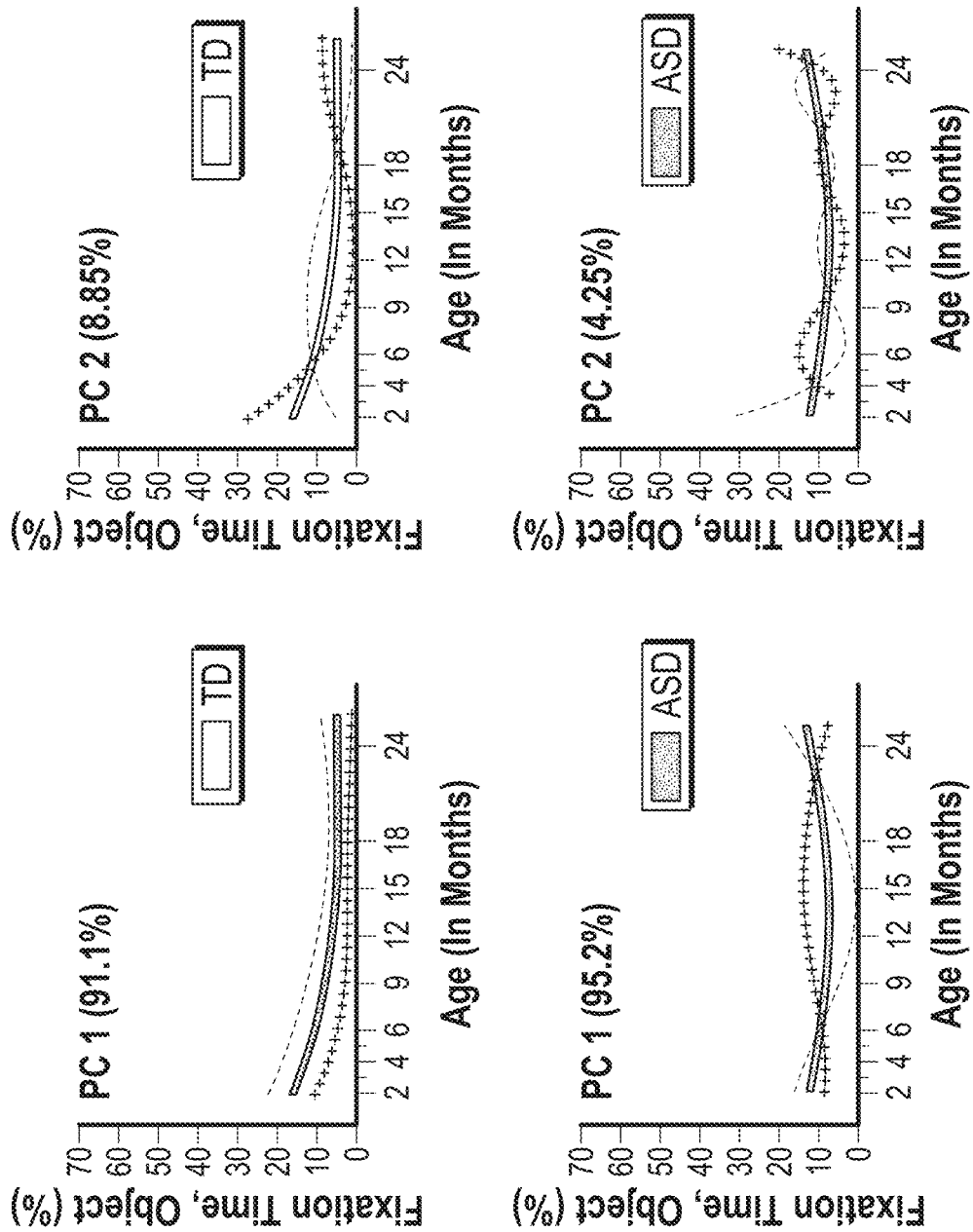

The present experiment also considered these data as part of a larger continuum. FIG. 20D is a graph illustrating that eye fixation varies systematically across all outcome groups, with significant interaction of Outcome by Age (by HLM). Graded developmental trajectories are evident in the significant interaction of Outcome [4 levels] by Age: $F_{3,133.006}=6.95$, P<0.001 (HLM). Typically-developing children show strongly increasing eye fixation. Unaffected siblings also show increasing eye fixation. Siblings with subthreshold symptoms show neither increasing nor decreasing eye fixation, and infants later diagnosed with ASD show declining eye fixation. Additional illustrations and experimental data relevant to this point are shown in FIGS. 26A-26M, which generally show developmental change in visual fixation on the eyes relative to outcome levels of affectedness. FIG. 26A is a graph showing percent fixation on eyes for typically-developing infants. FIG. 26C is a graph showing percent fixation on eyes for infants at high risk for ASD who showed no evidence of ASD at 36 months. FIG. 26E is a graph showing percent fixation on eyes for infants at high risk for ASD who showed some subthreshold signs of the Broader Autism Phenotype at 36 months but did not meet clinical best estimate diagnosis of ASD. FIG. 26G is a graph showing percent fixation on eyes for infants diagnose with ASD at 36 months. Similarly, the plots shown in FIGS. 26B, 26D, 26F, and 26H show mean fixation curves with 95% CI.

In FIG. 20E, individual results for change in eye and body fixation (with respect to eye and body regions-of-interest of persons shown in a stimuli) are plotted dimensionally, across the full spectrum of social ability to disability. The probability density functions on ordinate and abscissa indicate whole sample distributions for change in eye and body fixation. The data show gradations from typically-developing children to those diagnosed with ASD, with children with ASD showing the largest decline in eye fixation as well as the greatest increase in body fixation. Values for unaffected siblings are fully overlapping with those of typically-developing children, while children with BAP outcomes show intermediary behaviors.

Analysis

As shown by the above description and related figures, the results of the above experiment indicate that the development of infants later diagnosed with ASD differs from that of their typical peers by 2-6 months of age. These results, while still limited in sample size, document the derailment of skills that would otherwise guide typical socialization. Given the interdependence of individual experience with brain structure and function, and with gene expression and methylation, these results suggest how a single individual's outcome will be shaped not only by initial genotypic vulnerabilities, but also by the atypical experiences that arise as a consequence of those vulnerabilities, instantiating a wide spectrum of affectedness.

In children later diagnosed with ASD, eye looking (e.g., visual fixation) shows mean decline by at least 2 months of age. It is surprising and against conventional belief, however, that those early levels of eye looking appear to begin at normative levels. This contradicts prior hypotheses of a congenital absence of social adaptive orientation and suggests instead that some social-adaptive behaviors may initially be intact in newborns later diagnosed with ASD. The above-described systems and methods offer a remarkable opportunity for treatment: predispositions that are initially intact suggest a neural foundation that might be built upon, offering far more positive possibilities than if that foundation were absent from the outset.

Experimental Methods

The data collected in respect to the above-described experiment were used for research purposes only, with no relationship to clinical care. Families were free to withdraw from the study at any time. All aspects of the experimental protocol were performed by personnel blinded to diagnostic status of the children. All diagnostic measures were administered by trained clinicians blinded to results of experimental procedures. The children were shown, at each of 10 longitudinal testing points between 2 and 24 months of age, video scenes of naturalistic caregiver interaction. The experiment measured percentage of visual fixation time to eyes, mouth, body, and object regions-of-interest in dynamic stimuli, and these measures served as the dependent variables for longitudinal analyses. Planned confirmatory analyses measured longitudinal fixation trajectories relative to both categorical diagnostic outcome and dimensional level of social/communicative disability. Visual scanning was measured with eye-tracking equipment (as referenced earlier in this disclosure). Analysis of eye movements and coding of fixation data were performed with software written in MAT-LAB. As will be understood and appreciated, however, the visual scanning, analysis of data, and other processes described herein may be performed utilizing a variety of similar technologies, and no limitations of the present disclosure are intended by the specific references made herein.

Additional details on participants, clinical assessment procedures, assignment of group membership, are provided in Supplemental Experiment Information section of the present disclosure.

Experimental Stimuli

The children in the present experiment were shown video scenes of a female actor looking directly into the camera and playing the role of a caregiver: entreating the viewing toddler by engaging in childhood games (e.g., playing pat-a-cake) (see FIGS. 17A and 17B, and corresponding description, referenced above). The actors were filmed in naturalistic settings that emulated the real-world environment of a child's room, with pictures, shelves of toys, and stuffed animals. Naturalistic stimuli (e.g., dynamic rather than static stimuli, and realistic rather than abstracted or reductive scenes) were used in light of past research indicating that older children with ASD exhibit large discrepancies between their actual adaptive behavior skills in the real world relative to their cognitive potential in more structured situations; exhibit larger between-group effect sizes for face-processing deficits with dynamic relative to static stimuli; and exhibit marked difficulties when attempting to generalize skills from structured, rote environments (in which the skills were initially learned) to environments that are open-ended and rapidly-changing. At each data collection session, videos were drawn in pseudo-random order from a pool of 35 total. Both the "caregiver" video stimuli analyzed here (35 videos), as well as videos of infant and toddler interaction ("peer-play" videos) were presented. Video stimuli were presented in pseudo-random order. There were no between-group differences in duration of data collected per child, either in total ($t_{34}$=0.685, P=0.498) or specifically for the caregiver stimuli ($t_{34}$=0.205, P=0.839). Successful data collection was achieved in 80.2% of all testing sessions; failed data collection sessions occurred as the result of an infant falling asleep, crying, or becoming too fussy to watch the videos. Reasons for failure were recorded in data collection reports for each session and maintained in a database; no systematic difference in reasons for failure could be discerned between the two groups. At each data collection session, approximately 30% of the videos shown to a child were novel, while the remaining 70% were repeated from previous sessions (from both the immediately preceding session as well as from any prior session beginning at month 2 onwards). This balanced the need for repeated measures to the same stimulus video with the need for novelty. To test for learning effects of repeated presentations, end-stage results at 24 months in this longitudinal sample were compared with previous results in a cross-sectional sample at that age: tested by 2×2 between-subjects factorial ANOVA, there was no main effect of cohort, longitudinal vs. cross-sectional ($F_{1,57}$=0.052, P=0.820), but there was a significant main effect of diagnosis (ASD vs. TD, $F_{1,57}$=6.29, P=0.015).

Caregiver videos were presented as full-screen audiovisual stimuli on a 20-inch computer monitor (refresh rate of 60 Hz noninterlaced); in 32-bit color; at 640×480 pixels in resolution; at 30 frames per second; with mono channel audio sampled at 44.1 kHz. Stimuli were sound and luminosity equalized, and were piloted prior to the start of study in order to optimize engagement for typical infant and toddler viewers. Regions-of-Interest (Eye, Mouth, Body, & Object) were bitmapped in all frames of video (as represented in FIG. 17C, discussed above). Average sizes of the regions-of-interest are shown in more detail in Table 1 below.

TABLE 1

Size of Regions of Interest.

| | Eyes | Mouth | Body | Object |
|---|---|---|---|---|
| Horizontal[1] | 8.04° (0.46) | 7.71° (0.49) | 25.11° (2.70) | 31.99° (0.05)[2] |
| Vertical[1] | 6.91° (0.44) | 5.72° (0.59) | 21.71° (0.73) | 23.94 (0.49)[2] |

[1]Data are given as mean (SD) in degrees of visual angle.
[2]Object ROIs generally spanned the full horizontal and vertical extent of the background in all videos images, excepting cases of some body and hand gestures, as shown in FIG. 1 in the main text. The average minimum visual area subtended by any portion of the object ROI is equal to the difference between objects and body ROIs Experimental Setting and Equipment Two settings for eye-tracking data collection were utilized in the present study. One eye-tracking laboratory was optimized for infants between the ages of 2 and 6 months, and a second setting was optimized for infants and toddlers from 9 to 36 months. The primary distinction between the two settings was the use of a reclined bassinet (similar to the seats 101 shown in the embodiments of device 100 in FIGS. 3A, 3B, 3D, 3E, and 3F) for younger infants versus the use of a car seat (similar to the seats 101 shown in the embodiments of the device 100 in FIGS. 2 and 3C) for older infants and toddlers. The eye-tracking data collection hardware and software were identical in both settings, and all aspects of automated stimuli presentation, data collection, and analysis were also identical. To obtain optimal eye imaging with infants in the reclined bassinet, eye-tracking cameras and infrared light source were concealed within a teleprompter. In the toddler lab, eye-tracking cameras were mounted beneath a computer display monitor. The display monitor was mounted flush within a wall panel. In both labs, eye-tracking was accomplished by a video-based, dark pupil/corneal reflection technique with hardware and software created by ISCAN, Inc. (Woburn, MA, USA), with data collected at 60 Hz. In both labs, audio was played through a set of concealed speakers. Infants were placed in a modified travel bassinet, mounted on a table that was raised and lowered at the beginning of each session to standardize the positioning of the infant's eyes relative to the display monitor. In the toddler lab, children were seated in a car seat in front of the computer screen on which the videos were presented. As in the infant lab, the car seat was raised and lowered so as to standardize the position of each child's eyes relative to the display monitor.

Experimental Protocol

Infants and toddlers were accompanied at all times by a parent or primary caregiver. To begin the experimental session, the participant (infant or toddler) and caregiver entered the laboratory room while a children's video played on the display monitor. The child was buckled into the bassinet or car seat. Eye position relative to the display monitor was then standardized for each child by adjusting the seat or bassinet location. Viewers' eyes were approximately 28 inches (71.12 centimeters) from the display monitor, which subtended an approximately 24°×32° portion of each viewer's visual field. Lights in the room were dimmed so that only content presented on the display monitor could be easily seen. During testing, both experimenter and parent were out of view from the child but were able to monitor the child at all times by means of an eye-tracking camera and by a second video camera that filmed a full-body image of the child.

Visual fixation patterns were measured with eye-tracking hardware 104. To begin the process of data collection, after the child was comfortably watching the children's video, calibration targets were presented onscreen by the experimenter (as described above in connection with step 310 in FIG. 4, and FIGS. 5C-5I). This was done via software that paused the playing video and presented a calibration target on an otherwise blank background. A five-point calibration scheme was used, presenting spinning and/or flashing points of light as well as cartoon animations, ranging in size from 1° to 1.5° of visual angle, all with accompanying sounds. For the infants, calibration stimuli began as large targets, >=10° in horizontal and vertical dimensions, which then shrank via animation to their final size of 1° to 1.5° of visual angle. The calibration routine was followed by verification of calibration in which more animations were presented at five on-screen locations. Throughout the remainder of the testing session, animated targets (as used in the calibration process) were shown between experimental videos to measure drift in calibration accuracy. In this way, accuracy of the eye-tracking data was verified before beginning experimental trials and was then repeatedly checked between video segments as the testing continued. In the case that drift exceeded 30, data collection was stopped and the child was recalibrated before further videos were presented. For additional details and measures of calibration accuracy, please see the Supplemental Experiment Information section and FIGS. 28A-28C (discussed above).

Data Analysis of Eye Movements

For the particular described experiment, Analysis of eye movements and coding of fixation data were performed with software written in MATLAB (MathWorks). The first phase of analysis was an automated identification of non-fixation data, comprising blinks, saccades, and fixations directed away from the stimuli presentation screen. Saccades were identified by eye velocity using a threshold of 30°/second. The experiment tested the velocity threshold with the 60 Hz eye-tracking system described above and, separately, with an eye-tracking system collecting data at 500 Hz (Senso-Motoric Instruments GmbH, Teltow, Germany). In both cases saccades were identified with equivalent reliability as compared with both hand coding of the raw eye position data and with high-speed video of the child's eyes. Blinks were identified in the data. Off-screen fixations (when a participant looked away from the video) were identified by fixation coordinates beyond the stimuli presentation screen.

Eye movements identified as fixations were coded into 4 regions-of-interest that were defined within each frame of all video stimuli: eyes, mouth, body (neck, shoulders, and contours around eyes and mouth, such as hair), and object (surrounding inanimate stimuli) (see FIG. 17C). The regions-of-interest were hand traced for all frames of the video and were then stored as binary bitmaps (via software written in MATLAB; MathWorks, Inc, Natick, Massachusetts). Automated coding of fixation time to each region of interest then consisted of a numerical comparison of each child's coordinate fixation data with the bitmapped regions of interest.

Longitudinal Data Analysis

To examine the longitudinal development of social visual attention, for individual participants and across both ASD and TD groups, the experiment used Functional Data Analysis (FDA) and Principal Analysis by Conditional Expectation (PACE) (see FIGS. 17D and 17E for example individual fits, and FIG. 18 for group results; as well as FIG. 27). Although the experiment focused on FDA/PACE in order to overcome limitations inherent to cross-sectional analyses, as well as some limitations of traditional growth curve analyses, all analyses were repeated using hierarchical linear modeling (HLM) (as represented in FIGS. 24, 25, and 26, and in Table 2 below). Although the two methods yielded the same pattern of significant between-group differences (as described above), the FDA approach is generally preferable because traditional growth curve analyses can be confounded by individual differences in developmental timescale, and also because traditional growth curve analyses often require correct assumption of an underlying parametric or semi-parametric model (rather than allowing this to be determined in a data-driven fashion). In contrast, FDA methods determine curve shape empirically and model statistical variation in both time scale as well as amplitude. The PACE method of FDA is also designed specifically to overcome a common problem for longitudinal studies: non-uniform sampling particularly in the case of missing values. PACE characterizes statistical ensembles of irregularly-sampled longitudinal data in terms of entire curve shapes on the basis of conditional expectation. This maximizes the ability to detect patterns of correlation across trajectories and minimizes the impact of data sampled at discrete intervals with varying number of measurements per participant. This approach significantly improves the detection of common features in trajectory shape.

TABLE 2

Parameter Values for PACE/FDA Smoothing Bandwidths, Eigenfunctions, and FVE

| | Group | $w_\mu^1$ | $w_G^2$ | Eigenfunctions[3] | FVE |
|---|---|---|---|---|---|
| Eyes | TD | 5.7045 | [2.5422, 2.5422] | 2 | 96.48%, 3.49% |
| | ASD | 6.3868 | [2.2335, 2.2335] | 3 | 82.72%, 10.66%, 6.18% |
| Mouth | TD | 5.6800 | [2.5431, 2.5431] | 2 | 94.06%, 5.93% |
| | ASD | 6.3879 | [2.2339, 2.2339] | 3 | 69.89%, 20.95%, 8.98% |
| Body | TD | 5.6723 | [2.5415, 2.5415] | 2 | 9;1.75%, 8.19% |
| | ASD | 6.3894 | [2.2339, 2.2339] | 2 | 98.71%, 1.28% |
| Object | TD | 5.6935 | [2.5433, 2.5433] | 2 | 91.14%, 8.85% |
| | ASD | 6.3883 | [2.2331, 2.2331] | 2 | 95.25%, 4.25% |

[1]Bandwidth for mean function, $w_\mu$, selected by generalized cross-validation.
[2]Bandwidth for covariance surface, $w_G$ selected by generalized cross-validation.
[3]Numbed of eigenfuctions selected by Akaike Information Criterion (AIC).
FVE = Fraction of Variance Explained As noted above, as a methodological comparison to FDA, data was also analyzed using hierarchical linear modeling. The presence of linear and curvilinear (quadratic and cubic) patterns was assessed for Fixation relative to Age via the following model: $Fixation_{ij} = intercept_j + d_{ij} + B_{1j}(Age_{ij}) + B_{2j}(Age_{ij})^2 + B_{3j}(Age_{ij})^3 + e_{ij}$; where $d_{ij}$ represents the normally distributed random effect modeling within-subject dependence by group; $e_{ij}$ represents the normally distributed residual error; and the $B_1$, $B_2$, and $B_3$ coefficients indicate how fixation levels change with age and by group. Initial evaluation of the data indicated an inverse relationship between body fixation and age, and was therefore also assessed with the following model: $Body\ Fixation_{ij} = d_i + intercept_j + (B_{ij}/Age_{ij}) + e_{ij}$. In all cases, the intercept and B terms were modeled as fixed effects but were allowed to vary by group. Degrees of freedom were calculated by the Satterthwaite method (equal variances not assumed). Positively skewed data (eg, body and object fixation trials) were log-transformed; plots show untransformed data. F tests and log-likelihood ratios were used to determine whether a linear, quadratic, cubic, or inverse relationship best described the data. Growth curves from hierarchical linear modeling are plotted in FIGS. 24 and 25 (discussed above), and the regression parameters for Eyes, Mouth, Body, and Object regions-of-interest shown in Table 3 below.

TABLE 3

Parameter Values for Hierarchical Linear Modeling.

|  | Model | Group | Intercept (s.e.m.) | Age coefficient $B_1$ (s.e.m.) | Age coefficient $B_2$ (s.e.m.) | Age coefficient $B_3$ (s.e.m.) |
|---|---|---|---|---|---|---|
| Eyes | $3^{rd}$ order | TD | 13.410 (19.009) | 9.6878 (4.5920) | −0.7919 (0.3801) | 0.0179 (0.0092) |
|  | $3^{rd}$ order | ASD | 66.979 (8.665) | −3.5843 (2.0843) | 0.0817 9 (0.1726) | 0.0001 (0.0042) |
| Mouth | $2^{nd}$ order | TD | 11.411 (13.269) | 3.6110 (1.6954) | −0.0917 (0.0537) | n.a. |
|  | $2^{nd}$ order | ASD | −6.596 (6.081) | 6.7058 (0.7762) | −0.1977 (0.0244) | n.a. |
| Body | Inverse | TD | 6.872 (5.162) | 45.6250 (28.3084) | n.a. | n.a. |
|  | Inverse | ASD | 13.450 (2.358) | 12.8734 (12.9730) | n.a. | n.a. |
| Object | $3^{rd}$ order | TD | 32.772 (8.973) | −5.7665 (2.3918) | 0.3570 (0.1980) | −0.0068 (0.0048) |
|  | $3^{rd}$ order | ASD | 17.366 (4.100) | −1.4479 (1.0913) | 0.0201 (0.0904) | 0.0014 (0.0022) | s.e.m. = standard error measure

Throughout the analyses, PACE parameters were selected by generalized cross-validation. Mean fixation curves from FIG. 18, together with the effects of adding or subtracting principal component functions (following the convention of Ramsay & Silverman), smoothing kernel bandwidths, and fractions of variance explained per principal component can be found in FIG. 27 and Table 2). The Akaike Information Criterion, with likelihood of measurements conditional on estimated random coefficients, was applied for selecting the number of principal components. Derivatives were computed by the PACE-QUO method.

Supplemental Experiment Information

As stated above, the presently-described experiment was conducted as a mechanism to implement and test certain embodiments of the present disclosure. As will be understood and appreciated, however, the details, testing methodology, participant criteria, and other information relating to this experiment is intended to be illustrative only. Thus, no limitation of the present embodiments or disclosure is intended by the specific recitation of experimental details and methods described herein and particularly below.

Participant Details

Inclusionary and Exclusionary Criteria. Participating mothers and infants were included in this study after the mothers provided written informed consent for themselves, permission for their infants, as well as permission for their older children and/or permission to provide information on older children.

High Risk (HR-ASD) sample. High-risk status was ascertained by having an older sibling who met criteria for an ASD based on expert clinical diagnosis and at least one of two diagnostic instruments: the Autism Diagnostic Interview Revised and/or the Autism Diagnostic Observation Schedule. Potential participants were excluded from the study if they displayed any one of the following: gestational age below 36 weeks; hearing loss or visual impairment determined at birth; non-febrile seizures; known medical conditions associated with autistic-like behaviors (e.g., Fragile X Syndrome, Tuberous Sclerosis); or any other identified genetic disorder. Infants requiring tube feeding or ventilation post-discharge were also excluded from participation. Ascertainment of exclusionary and inclusionary criteria included review of the mother's clinical file, completion of a medical history questionnaire, interview with caregivers, and a clinical examination of the baby by a pediatrician. Additional exclusionary criteria related to the child's ability to complete experimental procedures were applied once the child began to participate; these criteria are described in further detail below.

Low Risk (LR-TDx) Sample. Children were enrolled in the Low Risk (LR-TDx) sample (as used herein, "TD" generally refers to "typically-developing") if there was no family history of ASD in first, second, or third degree relatives; nor developmental delays in first degree relatives; nor pre- or perinatal complications. As above, additional exclusionary criteria related to the child's ability to complete experimental procedures were applied once the child began to participate in procedures; these criteria are described in greater detail below.

Medical, Developmental, and Genetic Assessment of Child. An attending pediatrician completed a thorough baby check-up at 15 months, and well-child exams were reviewed for each child from birth throughout the first 2 years of life. The exam was used to assess the presence of identifiable medical conditions that might impact the child's development and to rule out sensorimotor difficulties that could compromise the child's participation in the experimental procedures. Otoacoustic emissions testing was used to assess hearing. The child's medical history was further reviewed regarding the course of birth and delivery. Attention was given to the course of delivery, presence of risk factors such as foetal brachycardia, low Apgar scores, newborn perinatal course, evidence of trauma, presence of dysmorphic features, skin findings, presence of seizures, primitive reflexes, motor abnormalities and asymmetries, as well as to prenatal exposure to harmful substances (e.g., valproic acid).

In addition, all infants at risk for ASD, contingent on parental consent, underwent pediatric and genetics assessments at 24 months, utilizing a template consistent with the format and content of the exam used by the Autism Genetic Resource Exchange (AGRE). The evaluation ruled out known genetic and developmental syndromes that might be confused with autism. In addition to eliciting medical history and constructing a three-generation pedigree, the Genetics Counsellor sought to obtain all available relevant medical records and test results on the child participant. Upon parental consent, a blood sample was also obtained for genetic analyses.

Gestational age at birth was not significantly different between groups, $t_{34}=0.08$, $P=0.938$, with ASD mean(SD)= 38.7(1.2) weeks and TD=38.7(1.7) weeks.

Direct Behavioral Assessment of Child. The Mullen Scales of Early Learning were administered at ages 6, 12, 18, 24, and 36 months to obtain standardized measures of cognitive functioning. The Autism Diagnostic Observation Schedule, modules T/1 and 2 (ADOS) were administered at ages 12, 18, 24 and 36 months (typically ADOS 1, or the Toddler Version, at ages 12, 18, and 24 months, and ADOS 1 and 2 at the age of 36 months).

Basic Visual Function. This study measured how infants and toddlers watch social stimuli, and how their patterns of preferential looking might relate to level of social functioning, autistic symptomatology, and diagnostic outcome. As noted above, gestational age was not significantly different between groups, an important consideration in light of recent findings that the development of binocular vision is experience-dependent, and varies in relation to postnatal experience. As a prerequisite for participation, prior to presentation of experimental stimuli, each child's ability to shift and stabilize gaze was tested. This procedure was included as a basic control against obvious symptoms of conditions affecting eye movement (e.g., conditions—such as nystagmus, Duane syndrome, or strabismus—that could adversely impact a child's ability to visually fixate video scenes of social content of the type used in this study). Children were shown a series of animated targets on an otherwise blank screen, and the elicited behaviors (saccading to the target and maintaining fixation) were measured with eye-tracking equipment as a minimal check of eye movement function. Children passed the screen if they were able to saccade to the target and maintain stable foveation, defined as less than 5°/sec of drift in visual fixation. The screen was conducted at each longitudinal visit, and with one exception (described below), all children passed.

These results confirmed prior research in ASD: while many studies in older children and adults have found differences in how individuals with ASD look at particular aspects of their surrounding environment, studies of eye movements in autism—that is, studies of the movements of the eyes themselves rather than of the content towards which the eyes are directed—have generally confirmed normal oculomotor function in children with autism in (a) maintaining steady fixation, as well as in velocity, duration, latency and accuracy of saccades; in (b) rates of intrusive saccades; in (c) vestibular-ocular reflex; and in (d) in foveopetal ocular drift. These studies suggest that the mechanics of oculomotor function appear to be generally intact in individuals with autism, and that differences in visual scanning are unlikely to arise from physiological aspects of eye movement; and are instead more likely to arise from the way in which eye movements are deployed to specific content and within specific contexts.

In the current study, one child in the HR-ASD sample failed the eye movement screen. That child was identified as having congenital nystagmus and was immediately referred to a pediatric neurologist and ophthalmologist for further evaluation and follow-up care. Although the nystagmus prevented collection of point-of-gaze data, this child remained in the study and was followed until 36 months. Sample recordings of his eye movements were collected (i.e., without point-of-gaze calibration) at each visit. At 24 months, and confirmed at 36 months, he was found to have no clinical ASD diagnosis.

Parent Interviews and Inventories. A comprehensive questionnaire and inventory was administered covering aspects of prenatal and perinatal history, general health history, and treatment and intervention history (if any). Items pertaining to the prenatal and perinatal history of the baby were obtained at the $1^{st}$ week and 3 month visits. Items pertaining to the overall health history of the baby were obtained at the 6, 12, 18, 24, and 36 month visits. Items pertaining to intervention history (if any) were obtained at 12, 18, 24, and 36 months. The Vineland Adaptive Behavior Scales—II were administered at 12, 18, 24, and 36 months to obtain standardized measures of adaptive function in the domains of communication, daily living skills, socialization, and motor skills. The Autism Diagnostic Interview—Revised (ADI-R) was administered to the parents by a trained and experienced interviewer with established reliability with the training site at the age of 36 months.

Reliability. All diagnostic measures were administered by trained clinicians who were blind to experimental procedures and results. In addition, supervising experienced clinicians, all with post-doctoral expertise in the clinical assessment of children with ASD and related developmental disorders, observed all diagnostic procedures and co-coded diagnostic instruments for reliability checks for every $5^{th}$ assessment throughout the protocol. Procedures were videotaped and archived for subsequent re-scoring, checking, and correction of possible drift during study duration.

Participants: Assignment of Group Membership & Best Estimate Diagnostic Procedures. Group membership of "ASD" or "non-ASD" for the N=59 HR-ASD children was carried out at the age of 24 months and was then confirmed at 36 months. No changes in group membership were observed between 24 and 36 months. As noted, one of the N=51 LR-TDx children was flagged by research staff as a child with ASD-like concerns at 12 months of age, and confirmed with ASD outcome at 24 and 36 months. All diagnostic measures were administered by trained clinicians who were blind to experimental procedures and results. Parents were informed that clinicians were blind to participants' risk status, with a request to refrain from any discussion of the older sibling (clinical questions and concerns regarding the older sibling or the child in question were addressed by clinicians not involved in the experimental or diagnostic ascertainment protocol of the project). As noted above, procedures involving direct contact with children and families that required reliability maintenance were videotaped and archived for subsequent re-scoring, checking, and correction of possible drift during study duration. At least two supervising clinicians independently assigned overall clinical diagnosis on the basis of a review of all available data (ADI-R and ADOS results and protocols, videotaped or direct observation of ADOS, cognitive and communication assessments, history, and any other clinically-relevant data).

Disagreements were discussed after data were entered for calculation of inter-rater reliability in order to obtain consensual clinician-assigned diagnosis. A third experienced clinician reviewed all of the materials for the N=11 male children with ASD included in the main study, and also for the N=2 males with ASD included in the external validation sample. Diagnostic ascertainment at the age of 36 months was completed in the same fashion.

Assignment of group membership of "ASD" or "non-ASD" was carried out at 24 months and then ascertained at 36 months with the involvement of at least one experienced clinician not involved in the 24-month diagnostic procedures. A best estimate diagnostic procedure was chosen as the gold standard for group membership (this choice was made in light of findings that indicate that experienced clinicians' judgment of children at the age of 24 months is a better predictor of later diagnosis than cut-off scores on the ADOS. While ADOS scores for individual children may vary during the first 2 to 3 years of life, best-estimate clinician-assigned diagnosis shows much more stability, and, in our group, approaches 100%. This is likely the result of the much broader frame of reference that is adopted during a best estimate diagnostic process, which includes the ADOS but also extends to other areas, specifically covering the following: historical developmental data; stability of traits in speech-language and communication symptoms (including communicative intent, voice and intonational quality of speech); results and profiles of standardized assessments and observations of speech-language-communication; and adequate weighting of low-frequency but highly-specific stereotypic behaviors (including repetitive behaviors, unusual attachments, and exceptionally restricted interests). Spurts in development and intensive intervention targeting speech-language and communication skills between 24 and 36 months of age can also impact the stability of specific scores, while the broader frame of reference taken by experienced clinicians will account for these factors.

For the analyses focused on phenotypic heterogeneity among the High Risk siblings, the study divided the high-risk male infants who were not diagnosed with ASD at outcome into (1) those for whom there was never any clinical concern and whose typical development was ascertained at 24 and 36 months (HR-ASD_No-Dx), N=18; and (2) those for whom there were clinical concerns documented at any one of the clinical assessments. These concerns represented transient or subthreshold symptoms that did not meet criteria for ASD at 24- or 36-month evaluations. Because there are no consensual criteria for the diagnostic assignment of this subthreshold category, also called "Broader Autism Phenotype" (BAP), we followed currently adopted conventions as defined above, and as ascertained through the best-estimate diagnostic procedure. N=10 male infant siblings met these criteria (HR-ASD_BAP).

Group membership of "TD" for the LR-TDx children was assigned at 24 months if there were no concerns of ASD and if children's developmental assessment scores on the Mullen did not show either two scores falling 1 SD below the mean or one score falling 1.5 SDs below the mean. At 33 months, the entire LR-TDx group also completed a Vineland in order to ascertain maintenance of TD status; any case for whom there was any developmental concern was then invited to complete a full clinical characterization protocol at the age of 36 months. All 25 males from the LR-TDx cohort were confirmed to have typical outcome.

ASD, HR-non-ASD, and TD Clinical Characterization Data: Group Comparisons. Clinical characterization data for the outcome comparisons between the N=11 ASD and N=28 HR-non-ASD male children, and between the N=11 ASD and the N=25 TD male children are provided here. As noted above, from the original N=59 HR-ASD children, N=12 converted to a diagnosis of ASD at 24 months, confirmed again at 36 months: 10 males and 2 females. Because of the small number of females, they were excluded from current data analyses. Of the remaining N=47 children in the HR-ASD group, N=28 were males and N=19 were females. One male child from N=51 LR-TDx group showed concerning behavior at 12 months and converted to a diagnosis of ASD by 24 months (and again confirmed at 36 months); that child was, therefore, included in the ASD group (N=11 in total). For comparison's sake, we also conducted analyses with that child excluded (described in greater detail below). As noted above, the typically-developing status of the remaining N=50 LR-TDx children was assessed at 24 and was then confirmed again at 33 (and, if necessary, 36) months. Of these, N=25 were males and N=25 were females. The male TD children's data provided the normative benchmarks for the typical growth charts of social visual attention used in data analyses.

As diagnostic group membership was first assigned at 24 months, we provide here diagnostic (ADOS) and developmental (Mullen and Vineland) summaries at that age for the ASD group (N=11), all males, and for the group of HR-non-ASD (N=28), all males, from the HR-ASD risk-based cohort. Data comparisons are provided below in Table 4.

TABLE 4

Data Comparison of Diagnostic and Developmental Summaries.

| | ASD Group [1] | HR-non-ASD Group [1] | $t_{37}$ values | p values |
|---|---|---|---|---|
| N | 11 | 28 | | |
| ADOS-SA [2] | 7.55 (4.46) | 3.93 (2.59) | 3.169 | 0.003 |
| ADOS-RRB [3] | 3.91 (1.7) | 1.96 (1.31) | 3.817 | <0.001 |
| ADOS-Total [4,5] | 11.45 (5.06) | 5.89 (2.92) | 4.306 | <0.001 |
| Mullen, NV AE [6] | 23.36 (6.20) | 25.46 (4.59) | −1.163 | 0.252 |
| Mullen, RL AE [7] | 22.45 (7.59) | 24.50 (6.66) | −0.829 | 0.412 |
| Mullen, ELV AE [8] | 22.18 (7.56) | 26.75 (6.26) | −1.932 | 0.061 |
| Vineland, CommAE [9] | 19.73 (5.85) | 25.14 (5.68) | −2.657 | 0.012 |
| Vineland, SocAE [10] | 16.18 (3.63) | 19.00 (2.19) | −2.978 | 0.005 |

[1] ASD Group = Autism Spectrum Disorders; HR-non-ASD = Non-Autism Spectrum Disorder Outcome from High Risk Group
[2] ADOS-SA: *Autism Diagnostic Observation Schedule*, Social Affect Cluster; higher scores on the ADOS indicate more severe autistic symptomatology;
[3] ADOS-RRB: *Autism Diagnostic Observation Schedule*, Restricted and Repetitive Behaviours Cluster; higher scores on the ADOS indicate more severe autistic symptomatology;
[4] ADOS-Total: *Autism Diagnostic Observation Schedule*, Sum of ADOS-SA + ADOS-RRB; higher scores on the ADOS indicate more severe autistic symptomatology.
[5] Autism Spectrum Cut-off = 8;
[6] Mullen, NV: *Mullen Early Scales of Learning*, Visual Reception (Nonverbal Function) Age Equivalent;
[7] Mullen, RL: *Mullen Early Scales of Learning*, Receptive Language Age Equivalent;
[8] Mullen, EL: *Mullen Early Scales of Learning*, Expressive Language Age Equivalent;
[9] Vineland, CommAE: *Vineland Adaptive Behaviour Scales*, Communication Domain Age Equivalent (in months);
[10] Vineland, SocAE: *Vineland Adaptive Behaviour Scales*, Socialization Domain Age Equivalent (in months).

The ASD and the HR-non-ASD groups differed significantly in levels of autistic symptomatology; as expected, the ASD group displayed higher levels of symptoms in the Social Affect (ADOS-SA) and Restricted & Repetitive Behaviors (ADOS-RRB) clusters as well as in the ADOS Total (ADOS-Total) scores. At 24 months, the ASD group had a mean ADOS-Total score of 11.45, exceeding by close to 3.5 points the ASD cut-off score of 8. The ASD and HR—non-ASD groups also differed significantly on levels of adaptive behaviors in the Communication and Socialization domains, with the ASD group displaying significantly lower levels of abilities in these areas. The ASD and HR-non-ASD groups exhibited comparable levels of nonverbal and verbal function (although levels of Expressive Language skills trended in the direction of higher levels obtained for the HR-non-ASD group). These results confirm that the ASD group displayed higher levels of autistic symptomatology and lower levels of social and communicative adaptive skills while being comparable on levels of cognitive and receptive language skills. These results are consistent with expected differences between ASD and HR-non-ASD groups from an initial HR-ASD cohort.

For regression analyses (see FIG. 21), the experiment used 24-month outcome data to maximize comparability with previous cross-sectional and longitudinal work. Correlation between decline in eye fixation and ADOS scores at either 24 or 36 months was not significantly different, $z=0.86$, $P=0.390$ (Fisher's r to z transform). Although the experiment used the ADOS-SA as the primary outcome measure, decline in eye fixation was also significantly associated with ADOS Total score, $r=-0.731$ [$-0.23$--$0.93$, 95% CI], $P=0.01$. The experiment also compared measures between the time of diagnostic membership assignment at 24 months and diagnostic confirmation at 36 months: a comparison of ADOS scores at each of the 2 testing times for the N=11 ASD children revealed no significant differences in group measures of ADOS-SA (mean=7.55, SD=4.45, and mean=7.27, SD=3.63, respectively, for 24 and 36 months); ADOS-RRB (mean=3.91, SD=1.70, and mean=3.27, SD=1.48, respectively, for 24 and 36 months); and ADOS-Total (mean=11.45, SD=5.06, and mean=10.55, SD=4.20, respectively, for 24 and 36 months). The comparison was between ADOS module 1 at 24 and at 36 months in order to ensure comparability of scores across the 2 ages. Although all but 3 children with ASD were able to complete the ADOS-2 (i.e., met the expressive language criteria for a meaningful administration of this module), they were scored on both ADOS-1 and ADOS-2 because, as a rule, scores on a higher module are typically higher (i.e., indicating greater disability) because demands upon the child are higher.

For the comparison between the N=11 ASD and the N=25 TD children, at 6 months of age, there were no between-group significant differences in either nonverbal/cognitive or (pre)verbal/language skills, measured as age-equivalent scores in months, with Mean (SD) for TD=5.8 (0.6) vs. ASD=5.6 (0.9) for nonverbal/cognitive skills; and TD=5.1 (0.6) vs. ASD=4.7 (1.1) for receptive/expressive (pre)verbal/language skills. At 12 and 24 months, the two groups did not differ in nonverbal/cognitive skills (P=0.118 and P=0.136, respectively), but did differ in receptive/expressive language skills (consistent with the expected communication deficit in toddlers with autism), with means of 10.5 (2.0) for TD vs. 8.8 (2.2) for ASD at 12 months (P=0.032); and 27.4 (4.4) for TD vs. 22.3 (7.3) for ASD at 24 months (P=0.036).

Finally, for the analyses focused on phenotypic heterogeneity among the High Risk infant siblings, the HR-ASD_BAP and the HR-ASD_No-Dx groups differed significantly in levels of autistic symptomatology; as expected, the HR-ASD_BAP group displayed higher levels of symptoms in the ADOS Total (ADOS-Total) scores relative to the HR-ASD_No-Dx, with means of 9.7 (3.1) and 4.8 (2.4), respectively (t(26)=4.65, P<0.001). These results are consistent with expected differences between these groups.

Sample Size. Sample size was selected according to power calculations based on earlier work in toddlers with ASD, in which the effect size of ASD vs. TD between-group differences in eye fixation was equal to d=1.56 (Cohen's d). Greater variability was expected in typical infant development and thus reduced expectations of effect sizes and increased the sample allocation ratio. In order to observe cross-sectional results with "large" expected effect sizes (0.8 or greater), with standard α-level of 0.05, power equal to 0.8, and with sample allocation ratio equal to 4 (increased from 2.4 TD:ASD), it was calculated that samples of N=12 children with ASD and N=50 TD children would be required. Sex rations were expected in ASD leading to at least 9 boys with ASD and 25 TD children, this sample size was also adequately powered to detect sex-specific differences (requiring slightly larger expected effect sizes, at d=1.0). With an expected 20% conversion rate (conversion from HR-ASD to ASD, consistent with other studies of infant siblings), confirmation of N=12 ASD children at outcome was expected to require an initial cohort of 60 HR-ASD infants.

In line with these estimates, analyses were conducted on the first consecutively enrolled cohort of N=59 HR-ASD siblings of children with ASD, and N=51 low-risk (LR-TDx) children. Analyses were conducted when 12 HR-ASD infants received confirmatory ASD diagnoses at 36 months. The total sample size of N=110 compares well with other prominent studies of infants at-risk for ASD. Statistical power was increased by repeated sampling: these 110 children completed more than 960 visits and more than 7,893 trials of experimental eye-tracking procedures. Sex ratios in the ASD outcome group were approximately as expected (10:2 male to female), and, in addition, one LR-TDx infant also received an ASD diagnosis at 36 months. In total, N=11 male ASD children were confirmed at 36 months. Although this sample is still relatively small in absolute terms, effect sizes for between-group comparisons of longitudinal eyes, body, and object fixation (plotted in FIG. 18), with Cohen's d values ranging from 1.18 to 1.26, indicate adequate power for detection of differences. In addition, this sample is the largest yet collected with data at the age of 2 months for children later diagnosed with ASD. Some other prominent studies have included data collection in the first year of life, but more often only at 6 and/or 12 months of age. The current study complements those approaches by using a smaller overall sample size but more frequent sampling, with more than 400 successful data collection sessions completed by the time these infants reached the age of 6 months.

Female Infants with ASD. Data was not included from females in the main analyses because of concerns about what conclusions could or should be drawn on the basis of 2 female participants. Given the almost 5:1 male:female ratio in autism spectrum disorders, the sample size problem for studying females with autism—especially when utilizing a risk-based infant siblings strategy—is daunting but not unexpected.

Experimental Procedures

Considerations in Selection of Experimental Design. The goal in this study was to test the extent to which performance-based measures of evolutionarily highly-conserved, and developmentally early-emerging mechanisms of typical social adaptation may be disrupted in autism spectrum disorders (ASD), at a point prior to the manifestation of overt symptoms of social disability. For this purpose, a design was adopted marked by 3 main features.

Focus on Foundational Social Skills. The experiment focused on disruptions of foundational social skills that are already online in typical babies from the first days and weeks of life. This choice was made because several research groups have conducted studies of the natural course of autistic symptoms using observational and experimental methods, with no clear indicators of overt ASD symptomatology in the first year of life. The experiment focused instead on whether normative mechanisms of social development were intact or disrupted in infants with ASD, and how those mechanisms were shaped in TD infants during early development. This approach follows the idea that between genetic liability and behavioral symptoms lies the disruption of highly conserved, normative mechanisms of socialization; the disruption of these mechanisms is not a symptom in and of itself, but rather a divergence in developmental course that will later give rise to symptoms.

Dense, Prospective Sampling of Early Infant Behavior. The dizzying pace of social and communicative development in the first year of life, together with the corresponding brain specialization in that same timeframe, suggests that measures of infancy must keep pace with the accomplishments of infancy. To that end, in order to quantify atypical deviations from normative developmental trajectories, a high-density sampling design was selected, with data collection occurring 5 times before the age of 6 months, a total of 7 times by the age of 12 months, and 10 times by the age of 24 months.

Longitudinal Growth Charts of Preferential Visual Attention to Conspecifics. The intensive data collection allowed the experiment to model, with sufficient statistical power in repeated measurements, "growth charts" of normative social visual attention with the hypothesis that deviations therefrom would indicate a marker of unfolding ASD. Like many other phenomena in nature, babies' deployment of social visual attention is highly variable; at single cross-sectional time points, or even at 2 or 3 time points, that variability will drastically weaken statistical power to detect meaningful developmental changes. However, dense repeated sampling can shed light on robust predictability of maturational patterns.

The experiment addressed variability in individual data by using Functional Data Analysis (FDA) to generate growth curves, as FDA explicitly models statistical variation in both time scale and amplitude. This approach greatly improved detection of common features in trajectory shape and individual deviations (in magnitude and timing) relative to normative data. The experiment also repeated all analyses with traditional growth curve analysis using hierarchical linear modeling (HLM).

Equipment. Eye-tracking in both infant and toddler labs (as described above) was accomplished by a video-based, dark pupil/corneal reflection technique with hardware and software created by ISCAN, Inc. (Woburn, MA, USA). The systems employ remotely mounted eye-tracking cameras with data collected at a rate of 60 Hz. The systems were benchmarked against another eye-tracker collecting data at 500 Hz (SensoMotoric Instruments GmbH, Teltow, Germany), in both infants and in toddlers, to ensure that the 60 Hz frequency was sufficient for reliably identifying on- and offset of saccades at a threshold velocity of 300 per second.

Calibration. A five-point calibration scheme was used, presenting spinning and/or flashing points of light as well as cartoon animations, ranging in size from 1° to 1.5° of visual angle, all with accompanying sounds. For the infants, calibration stimuli began as large targets (>=100 in horizontal and vertical dimensions) which then shrank (via animation) to their final size of 1° to 1.5° of visual angle. The calibration routine was followed by verification of calibration in which more animations were presented at five on-screen locations. Throughout the remainder of the testing session, animated targets (as used in the calibration process) were shown between experimental videos to measure drift in calibration accuracy. In this way, accuracy of the eye-tracking data was verified before beginning experimental trials and was then repeatedly checked between video segments as the testing continued. In the case that drift exceeded 30, data collection was stopped and the child was recalibrated before further videos were presented.

In this manner, data was included if the verification procedure indicated fixation locations no further than 3° from target center; in the majority of cases, as seen in FIG. 28, the accuracy was well within this limit. Further, FIG. 28 includes "worst case" fixations, because it includes fixations that initiated a halt of data collection and recalibration of the child; these measures are included to show the full range of accuracy testing.

The minimum allowable drift was set at 3.0° because the average eye region in the videos (stimuli) subtended 8.0° by 6.9° of participants' visual angle. By setting the minimum allowable drift to 3.0°, it was assured that population variance in calibration accuracy would fall within 6.0°. The actual accuracy, as shown in the kernel density estimates in FIG. 29, is better than the worst case of a uniform distribution across a 6.0° region. As shown in FIG. 29, the probability distribution of fixation locations relative to target was heavily weighted within the central 1-2° and the minimum discriminable ROI is smaller than the size of the target ROIs in all months. Even the mouth ROI, which subtends only 5.7° in the vertical direction, is discriminable with accuracy well above chance thresholds.

Performance of Task. Given the young ages at which data were collected, and as a control for between-group differences in attention to task and completion of procedures, the experiment tested for differences in duration of data collected per child (TD=71.25(27.66) min, ASD=64.16(30.77) min, $t_{34}$=0.685, P=0.498); and for differences in the distribution of ages at which successful data collection occurred (k=0.0759, P=0.9556; 2-sample Kolmogorov-Smirnov). Trials in which a child failed to fixate on the presentation screen for a minimum of 20% total trial duration were excluded from analyses. The experiment tested for between-group differences in percentage of time spent saccading, blinking, or looking off-screen. And given the interest in results for the first 6 months alone as well as for the entire 24-month trajectory, the analyses were performed for both time periods.

As seen in FIG. 23, between months 2 and 6, there were no significant between-group differences in overall fixation time (see FIGS. 23A-23C) (no main effect of diagnosis, $F_{(1,21.652)}$=0.958, P=0.339, nor interaction of diagnosis by age, $F_{(1,20.026)}$>0.880, P=0.359, by hierarchical linear modeling (HLM), described in greater detail below); nor in percentage of viewing time spent saccading (see FIGS. 23D-23F) (no main effect of diagnosis, $F_{(1,27.189)}$=0.250, P=0.621, nor interaction of diagnosis by age, $F_{(1,26.430)}$>=0.561, P=0.460, by hierarchical linear modeling). During the entire period of data collection (months 2, 3, 4, 5, 6, 9, 12, 15, 18, and 24), non-fixation data (saccades+blinks+off-screen fixations) were not significantly different between groups, with no main effect of diagnosis ($F_{(1,234.012)}$=2.701, P=0.102), and with no interaction of diagnosis by month ($F_{(1,1776.615)}$=3.447, P=0.064). In the latter analysis, a trend level difference was observed, driven by increased off-screen fixation at month 24 in the ASD group.

Accuracy of Calibration. Calibration accuracy was measured as the distance between a child's fixation location and the center of the target location (for each target presented). Average calibration accuracy was less than 0.5 degrees of visual angle in the majority of all months (see FIG. 28A), and in every month, the average calibration accuracy was less than 1.5 degrees of visual angle.

Calibration accuracy was not significantly different between groups cross-sectionally, at any data collection session (all P>0.15, t<1.44; mean P=0.428; with comparisons conducted as independent samples t tests, at each month of data collection, without correction for multiple comparisons, so as to reduce the possibility of Type II error and be conservative in identifying between-group differences), nor longitudinally, as either a main effect of diagnosis ($F_{1,2968.336}$=0.202, P=0.65) or as an interaction of diagnosis by time ($F_{1,130.551}$=0.027, P=0.87). Longitudinal analyses of calibration accuracy were conducted by hierarchical linear modeling, and the relationship between calibration accuracy and age was modeled as an inverse function. The intercept and B terms were modeled as fixed effects but were allowed to vary by group. Degrees of freedom were calculated by the Satterthwaite method (equal variances not assumed).

Longitudinal Data Analyses. As described above, to examine the longitudinal development of social visual attention, both for individual participants and across both ASD and TD groups, we used Functional Data Analysis (FDA) and Principal Analysis by Conditional Expectation (PACE) (see FIGS. 17D and 17E, for examples of individual results, FIG. 18 for group results, and FIG. 27). Although we focused on FDA/PACE in order to overcome limitations inherent to cross-sectional analyses, as well as some potential limitations of traditional growth curve analyses, we repeated all analyses using hierarchical linear modeling (see FIGS. 22-26, and Table 3 referenced above).

Following the convention of Ramsay and Silverman, the correlation surface functions for fixation data in each group were also plotted; these are continuous estimates of the month-to-month correlations in looking patterns (i.e., a measure of the correlation between fixation at month 2 with fixation at month 3, with fixation at month 4, etc.). For eye fixation, in infants later diagnosed with ASD, negative correlations are observed when comparing earliest months to later months, indicating transition from high to low eye fixation; a positive correlation surface emerges by months 5 and 6, indicating thereafter that levels of eye fixation remain low or decline further. In TD children, the correlation surface remains generally high and positive, with surface depressions coinciding with periods of behavioral transition (e.g., between 4-6 months as eye fixation increases, and again between 12-18 months as eye fixation declines to accommodate increasing mouth fixation). The between-group differences in these surfaces indicate differences in underlying developmental processes.

As a methodological comparison to Functional Data Analysis, the experiment also analyzed the data using hierarchical linear modeling. The presence of linear and curvilinear (quadratic and cubic) patterns was assessed for Fixation relative to Age via the following model: $Fixation_{ij}=intercept_j+d_{ij}+B_{1j}(Age_{ij})+B_{2j}(Age_{ij})^2+B_{3j}(Age_{ij})^3+e_{ij}$; where $d_{ij}$ represents the normally distributed random effect modeling within-subject dependence by group; $e_{ij}$ represents the normally distributed residual error; and the $B_1$, $B_2$, and $B_3$ coefficients indicate how fixation levels change with age and by group. Initial evaluation of the data indicated an inverse relationship between body fixation and age, and was therefore also assessed with the following model: Body $Fixation_{ij}=d_i+intercept_j+(B_{ij}/Age_{ij})+e_{ij}$. In all cases, the intercept and B terms were modeled as fixed effects but were allowed to vary by group. Degrees of freedom were calculated by the Satterthwaite method (equal variances not assumed). Positively skewed data (e.g., body and object fixation trials) were log-transformed; plots show untransformed data. F tests and log-likelihood ratios were used to determine whether a linear, quadratic, cubic, or inverse relationship best described the data.

Growth curves from hierarchical linear modeling (HLM) are plotted in FIGS. 24-26, and the regression parameters for Eyes, Mouth, Body, and Object are given in Table 3. Age-related changes in eye fixation were best characterized by a cubic relationship [F(1,1870.709)=12.576, P<0.001, with change in log likelihood (−2 LL) indicating significantly improved fit for cubic relative to quadratic, $X^2(2)$=41.14, P<0.01]. Age-related changes in Mouth Fixation, however, were best characterized by a quadratic relationship [F(1,1505.768)=97.592, P<0.001, with change in log likelihood (−2 LL) indicating significantly improved fit for quadratic relative to linear, $X^2(2)$=93.05, P<0.001, but no improvement for cubic relative to quadratic, $X^2(2)$=2.14 P>0.05]. Age-related changes in Body Fixation were best characterized by an inverse relationship [F(1,20.613)=14.551, P=0.001, with change in log likelihood (−2 LL) indicating significantly improved fit relative to both quadratic, $X^2(2)$=47.298, P<0.001, and cubic, $X^2(4)$=16.464 P<0.01, functions]. Finally, age-related changes in Object Fixation were best characterized by a cubic relationship [F(1,1790.273)=11.206, P=0.001, with change in log likelihood (−2 LL) indicating significantly improved fit relative to quadratic, $X^2(2)$=23.563, P<0.01].

Analyses revealed significant main effects of Diagnosis for Eyes, Mouth, Body, and Object Fixation [F(1,146.416)=28.82, P<0.001; F(1,51.794)=6.275, P=0.015; F(1,24.141)=5.50, P=0.028; and F(1,240.460)=10.84, P<0.001; respectively]; as well as significant Diagnosis x Age interactions for Eyes, Mouth; Body, and Object Fixation [F(1,1870.709)= 12.58, P<0.001; F(1,1505.768)=13.103, P<0.001; F(1,20.613)=4.56, P=0.045; and F(1,1790.273)= 11.21, P<0.001; respectively].

Early Looking Behavior Relative to Later Outcomes: In order to explore the extent to which early looking behaviors related to a spectrum of affectedness, the experiment measured looking behavior, from 2-6 months, in relation to diagnostic outcomes at 36 months (see FIG. 19). To do so, we measured individual levels of eye fixation (see FIG. 19A) and rates-of-change (FIG. 19B) in eye fixation. The mean change in eye fixation was calculated between 2 and 6 months, for each child, and a receiver operating characteristic (ROC) curve was created to measure the overlap in distributions for affected children (infants who were later diagnosed with ASD) vs. unaffected children (TD infants) on the basis of mean change or rate-of-change in eye fixation (see FIGS. 19A-19C) and body fixation (see FIGS. 19G-19I). Because the ROC curves in FIGS. 19C and 19I are (necessarily) based upon data used to construct the model (and will thus give optimistically biased results), an internal validation was also conducted.

To conduct the internal validation, the experiment used leave-one-out cross-validation (LOOCV), partitioning the data set so that each infant in the cohort was tested as a validation case in relation to the remainder of the data set. For each infant in turn, the diagnostic label (from outcome diagnosis) was removed, and then calculated the infant's eye fixation and rate of change in eye fixation through conditional expectation of each outcome possibility (explicitly testing the assumption of each child belonging to either the ASD or the TD groups as ascertained at outcome). This process yielded two probabilities per child (the likelihoods, given a child's change or rate-of-change in eye or body fixation, of belonging to either of the outcome groups), and from these probabilities, a single odds ratio was calculated. Bootstrap 95% confidence intervals for the fitted ROC curve were computed.

Tests for Influential Observations: Month-Two Data and Individual Children. As in conventional statistical diagnostics for regression analyses, a series of tests were conducted to assess the impact of observations that might be overly influential on the data as a whole (i.e., outliers or observations with greater than expected leverage). FIG. 29 compares longitudinal growth curves when month-two data are included or excluded. Exclusion of the month-two data does not significantly alter the trajectories for eyes, mouth, body, or object fixation (see FIGS. 29A and 29B); nor does it alter the between-group comparisons thereof. Tests were also conducted of the influence of month-two data on the relationship between eye fixation and outcome levels of symptom severity within the ASD group (see FIG. 29C). When month 2 data are excluded, decline in eye fixation continues to significantly predict future outcome; this relationship reaches trend level significance by 2-9 months (P=0.097), and is statistically significant thereafter (with r=−0.714 [−0.2−−0.92, 95% CI], P=0.014 for 2-12 months). Finally, we tested the influence of month-two data on results for individual children. While confidence intervals for the cross-validated ROC curves increase in size (as expected, in proportion to the reduction in data that arises by excluding month 2), the levels of overlap between-groups remain significantly different from chance, and are not significantly different from the curves calculated when the 2-month data are included (see FIG. 29D).

The experiment also assessed the impact of the one low-risk infant who received an ASD diagnosis at outcome. Inclusion or exclusion of that child's data did not significantly alter the trajectories for eyes, mouth, body, or object fixation; nor did it alter the clinical relationship to outcome levels of symptom severity; nor the extent of overlap in scores for children with ASD relative to TD outcomes on the basis of their looking patterns in the first 6 months of life.

The experiment also assessed the impact of the one infant who later received a diagnosis of ASD and who exhibited the steepest decline in early eye fixation. Inclusion or exclusion of that child's data did not significantly alter the trajectories for eyes, mouth, body, or object fixation; nor did it alter the clinical relationship to outcome levels of symptom severity; nor the extent of overlap in scores for children with ASD relative to TD outcomes on the basis of their looking patterns in the first 6 months of life.

On the basis of the foregoing discussions, it will be understood that systems, devices, and methods disclosed herein may be implemented in digital electronic circuitry, in computer hardware, firmware, software, or in combinations thereof. Apparatus of the disclosure can be implemented in a computer program product tangibly embodied in a non-transitory machine-readable or non-transitory computer-readable storage device for execution by a programmable processor. Method or process steps of the disclosure can be performed by a programmable processor executing a program of instructions to perform functions of the disclosure by operating based on input data, and by generating output data. The systems, devices, and methods may be implemented using one or several computer programs that are executable in a programmable system, which includes at least one programmable processor coupled to receive data from, and transmit data to, a storage system, at least one input device, and at least one output device, respectively. Computer programs may be implemented in a high-level or object-oriented programming language, and/or in assembly or machine code, or any other suitable language or code. The language or code can be a compiled or interpreted language or code. Processors may include general and special purpose microprocessors. A processor receives instructions and data from memories. Storage devices suitable for tangibly embodying computer program instructions and data include forms of non-volatile memory, including by way of example, semiconductor memory devices, such as EPROM, EEPROM, and flash memory devices; magnetic disks such as internal hard disks and removable disks; magneto-optical disks; and Compact Disk. Any of the foregoing can be supplemented by or incorporated in ASICs (application-specific integrated circuits).

The foregoing is merely illustrative of the principles of the disclosure, and the systems, devices, and methods can be practiced by other than the described embodiments, which are presented for purposes of illustration and not of limitation. Although the embodiments and features herein are specifically described for use in connection with collecting and analyzing eye tracking data from subjects for the assessment, screening, monitoring, or diagnosis of autism spectrum disorders (ASD), it will be understood that the systems, devices, and methods may also apply to other developmental, cognitive social or mental abilities or disabilities, as well as other conditions, including but not limited to language disorders, intellectual disabilities, developmental disabilities with or without the presence of known genetic disorders, as well as attention deficit hyperactivity disorder (ADHD), attention deficit disorder (ADD), post-traumatic stress disorder (PTSD), head trauma, concussion, sports injuries, and dementia. It will be understood that such data, if not indicating measures for a disorder, may provide a measure of the degree of typicality of normative development, providing an indication of variability in typical development. Further, all of the components and other features outlined below may be combined with one another in any suitable manner and may be adapted and applied to systems outside of medical diagnosis. For example, the interactive visual stimuli of the present disclosure may be used as a therapeutic tool. Further, the collected data may yield measures of certain types of visual stimuli that subjects attend to preferentially. Such measures of preference have applications both in and without the fields of medical diagnosis and therapy, including, for example advertising or other industries where data related to visual stimuli preference is of interest.

Variations and modifications will occur to those of skill in the art after reviewing this disclosure. The disclosed features may be implemented, in any combination and subcombination (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A method of using a movable device to screen an individual for autism spectrum disorder (ASD) based at least in part on detected eye gaze data of the individual, comprising:

during display of predetermined stimulus videos on a display screen of the movable device while both the display screen and an eye gaze sensor mounted together with the display screen are oriented toward the individual at a linear distance of about 40-80 cm, receiving eye gaze data collected from the eye gaze sensor indicative of the individual's visual fixation over time with respect to the predetermined stimulus videos displayed on the display screen of the movable device, wherein the predetermined stimulus videos displayed on the display screen include social regions-of-interest distinct from other onscreen regions;

calculating, via software executing on a processor and using the eye gaze data collected from the eye gaze sensor during said display of the predetermined stimulus videos on the display screen of the movable device, visual fixation values for the individual including at least a percentage of time of the individual's visual fixation on the social regions-of-interest of the predetermined stimulus videos displayed on the display screen and an onscreen fixation value based at least in part on a detected amount of onscreen fixation time or a detected amount of off-screen fixation time;

after said calculating, providing an onscreen individualized result that graphically depicts an ASD diagnostic score and includes data collection information regarding the eye gaze data collected from the eye gaze sensor indicative of the individual's visual fixation.

2. The method of claim 1, wherein said providing the onscreen individualized further comprises generating a graphical representation of the individual's visual fixation with respect to one or more of the social regions-of-interest of the predetermined stimulus videos.

3. The method of claim 2, wherein the graphical representation of the individual's visual fixation comprises one or more lines marking measures of variance with respect to a comparison group.

4. The method of claim 1, wherein the social regions-of-interest of the predetermined stimulus videos displayed on the display screen are spatially predefined.

5. The method of claim 4, wherein the social regions-of-interest of the predetermined stimulus videos displayed on the display screen comprise one or more discrete regions of visual space.

6. The method of claim 5, wherein the one or more discrete regions of visual space are measured in degrees of visual angle equal to at least twice the minimum resolvable accuracy of the eye gaze data collected from the eye gaze sensor with 95% statistical confidence.

7. The method of claim 1, further comprising comparing, via the software executing on the processor, the eye gaze data collected from the eye gaze sensor indicative of the individual's visual fixation to earlier eye gaze data collected from the eye gaze sensor indicative of the individual's previous visual fixation over time with respect to the predetermined stimulus videos.

8. The method of claim 7, wherein said comparing identifies a change in visual fixation over multiple session for the individual with respect to the displayed predetermined stimulus videos, wherein the change in visual fixation over multiple sessions is a marker of a developmental, cognitive, social, or mental disability or ability.

9. The method of claim 1, wherein each frame of the predetermined stimulus videos comprises one or more predefined regions-of-interest different from another onscreen region of the frame.

10. The method of claim 9, wherein the one or more predefined regions-of-interest of each frame of the predetermined stimulus videos comprises at least one of the social regions-of-interest including an actor or animation.

11. The method of claim 1, wherein the eye gaze sensor comprises a camera fixedly mounted with the display screen and oriented to detect eye-movement of the individual during said display of the predetermined stimulus videos on the display screen of the movable device.

12. The method of claim 11, wherein the eye gaze sensor comprises an infrared light source.

13. The method of claim 11, wherein the eye gaze sensor is configured to detect a pupil position of the individual during said display of the predetermined stimulus videos on the display screen of the movable device.

14. The method of claim 11, further comprising identifying, via the software executing on the processor and using the eye gaze data collected from the eye gaze sensor during said display of the predetermined stimulus videos on the display screen of the movable device, blink information of the individual.

* * * * *